United States Patent [19]

Hamashima et al.

[11] Patent Number: 4,578,378
[45] Date of Patent: Mar. 25, 1986

[54] (OXOHETEROCYCLIC CARBONAMIDO)CEPHEM CARBOXYLIC ACID DERIVATIVES

[75] Inventors: Yoshio Hamashima, Kyoto; Koji Ishikura, Nara; Tadatoshi Kubota, Osaka; Kyoji Minami, Nara, all of Japan

[73] Assignee: Shionogi & Co., Ltd., Dosho, Japan

[21] Appl. No.: 625,308

[22] Filed: Jun. 27, 1984

[30] Foreign Application Priority Data

Jul. 6, 1983 [JP] Japan ................... 58-123698

[51] Int. Cl.$^4$ ............... A61K 31/535; C07D 498/04
[52] U.S. Cl. ........................ 514/210; 544/21; 544/25; 544/27; 544/90
[58] Field of Search ........... 544/58.2, 58.4, 90; 260/243.3; 424/246, 248.51, 248.52, 248.53, 248.55; 514/210

[56] References Cited

U.S. PATENT DOCUMENTS 4,443,598  4/1984  Yoshioka et al. ................... 544/90

Primary Examiner—Richard L. Raymond
Attorney, Agent, or Firm—Wenderoth, Lind & Ponack

[57] ABSTRACT

Antibacterial 7$\beta$-(oxo-saturated heterocyclic carbonamido)-3-cephem-4-carboxylic acid derivatives of the formula:

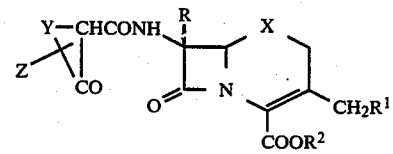

(wherein R is hydrogen or methoxy; $R^1$ is hydrogen or a nucleophilic group; $R^2$ is hydrogen, light metal, or a carboxy protecting group; X is oxygen, sulfur, sulfinyl, or sulfonyl; Y is alkylene containing one or more hetero atoms; and Z is hydrogen or a substituent).

14 Claims, No Drawings

(OXOHETEROCYCLIC CARBONAMIDO)CEPHEM CARBOXYLIC ACID DERIVATIVES

This invention relates to antibacterial 7β-(oxo saturated heterocyclic carbonamido)-3-cephem-4-carboxylic acid derivatives represented by the following formula (I):

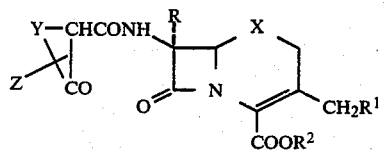

(wherein
R is hydrogen or methoxy;
$R^1$ is hydrogen or a nucleophilic group;
$R^2$ is hydrogen, light metal, or a carboxy protecting group;
X is oxygen, sulfur, sulfinyl, or sulfonyl;
Y is alkylene containing one or more hetero atoms; and
Z is hydrogen or substituent).

The nucleophilic group represented by $R^1$ has 1 to 8 carbon atoms excluding any protective group and is 4 to 6C heterocyclic ammonio and its counter ion (anion), 1 to 3C alkanoyloxy, optionally N-protected carbamoyloxy, halogen, 4 to 8C heterocyclic thio, or heterocyclic sulfoxido.

The heterocyclic ammonio can be pyridinium, carbamoylpyridinium, alkylpyridinium, or the like. Its counter ion is halogen, nitric, sulfuric, alkanoic, or the like anion or 4-carboxylate ion. Preferably alkanoyloxy is acetyloxy. The halogen can preferably be chlorine or bromine. The heterocyclic thio is thio substituted by mono- or di-cyclic, 5 to 6-membered aromatic heterocyclic groups containing 1 to 5 hetero atoms selected from nitrogen, oxygen, and sulfur, and optionally having various substituents. Among said heterocycles, the more preferable ones have 3 to 4 hetero atoms and a 5-membered ring system. Especially preferable ones are triazole, oxadiazole, thiadiazole, and tetrazole. Imidazole, triazine, and dihydrotriazine are also preferable. The substituent has 1 to 8 carbon atoms and can be, among others, alkyl, cyanoalkyl, carboxyalkyl, carbamoylalkyl, hydroxamoylalkyl, alkoxamoylalkyl, aminoalkyl, N-alkylated aminoalkyl, ureidoalkyl, haloalkyl, carbamoylhaloalkyl, arylthioalkyl, heterocyclic thioalkyl, sulfamoylalkyl, alkenyl, carboxy, amino, nitro, hydroxy, oxo, halogen, etc, linking through carbon, nitrogen, oxygen, halogen, or the like. Carboxy, carbamoyl, amino, hydroxy, oxo, etc., can conventionally be protected for reaction or use. More than two substituents can combine to form a ring. The most preferable heterocyclic thio for $R^1$ can be tetrazolylthio and thiadiazolylthio optionally substiuted by methyl, hydroxyethyl, carboxymethyl, carbamoylmethyl, amino, aminoethyl, dialkylaminoethyl, or cyanomethyl.

The carboxy-protecting group represented by $R^2$ has up to 15 carbon atoms and is known in the penicillin and cephalosporin fields and can be introduced or deprotected without adverse change on the other parts of molecule [aralkyl ester (benzyl, methylbenzyl, dimethylbenzyl, methoxybenzyl, ethoxybenzyl, nitrobenzyl, aminobenzyl, diphenylmethyl, phthalidyl, phenacyl, etc. ester), substituted alkyl ester (trichloroethyl, t-butyl, allyl, etc. ester), aryl ester (pentachlorophenyl, indanyl, etc. ester), N-hydroxyamino ester (ester with acetone oxime, acetophenone oxime, acetaldoxime, N-hydroxysuccinimide, N-hydroxyphthalimide, etc.), anhydride with carbonic or carboxylic acid, or the like. Reactive and substituted amide or hydrazide are equivalent and included in this carboxy-protecting group. These protecting groups may further be substituted as cited above. Especially useful carboxy protecting groups are those forming alkyl (alkanoyloxyalkyl, alkoxyalkyl, aminoalkoxyalkyl, etc.), aralkyl (benzyl, p-nitrobenzyl, phenacyl, phthalidyl, diphenylmethyl, etc.), and aryl (phenyl, halophenyl, etc.) esters. Especially useful carboxy derivatives among Compounds (I) are medically available, well known ones including light metal salts and pharmaceutically acceptable esters. The preferable light metal salts are those of a metal forming a physiologically acceptable ion and belongs to the 1st to 3rd group, 2nd to 4th series of the Periodical Table. Lithium, sodium, potassium, magnesium, calcium, aluminum and the like are preferable. The pharmacological esters have a potent antibacterial activity upon oral or parenteral administration including a well known 1 to 8C substituted alkyl ester (alkanoyloxyalkyl ester, alkoxycarbonyloxyalkyl ester, 2-oxo-1,3-dioxolenylmethyl ester, etc.), 7 to 10C substituted aralkyl ester (phenacyl ester, phthalidyl ester, etc.), and 6 to 10C substituted aryl ester (phenyl ester, xylyl ester, indanyl ester, etc.), all available in Compounds (I).

Divalent alkylene Y having hetero atoms in its chain has, preferably 3 to 7 atoms chain having no unsaturation in its chain, and the chain has 1 to 4 hetero atoms, i.e., nitrogen, oxygen, or sulfur. Sulfur can be —S—, —SO—, or —SO₂—. The most preferable Y groups are —NHCH₂CH₂CH₂—, —NHCH₂CH₂S—, and —NHCH₂S— forming a piperidine, thiomorpholine, or thiazolidine ring.

Substituents represented by Z may have up to 8 carbon atoms excluding a protective group and can be 1 to 4 substituents and can be a carbon function (1 to 3C alkyl, substituted alkyl, aralkyl, alkylidene, aryl, alkanoyl, nitrile, carbamoyl, carboxy, etc.), oxygen function (hydroxy, alkoxy, oxo, etc.), sulfur function (alkanesulfonyl, arylsulfenyl, etc.), halogen (Cl, Br, F, I, etc.), or the like which may further be substituted. The substituents on sulfur include oxo forming sulfoxide or sulfone. Especially useful substituents are alkyl, alkenyl, cyano, carboxy, protected carboxy, carboxyalkyl, hydroxyaminocarbonylalkyl, carbamoylalkyl, cyanoalkyl, aminoalkyl, ureidoalkyl, dialkylaminoalkyl, hyroxyalkyl, alkoxyalkyl, alkylthioalkyl, arylthioalkyl, haloalkyl, sulfamoylalkyl, alkoxysulfonylalkyl, alkylsulfonylalkyl, nitro, amino, hydroxy, alkoxy, acyloxy, aryloxy, oxo, halogen, or the like.

Among said definitions, the alkyl part is straight, branched, or cyclic alkyl. Acyl part is straight, branched, or cyclic alkanoyl, alkenoyl, carbalkoxy, carbamoyl, sulfo, alkylsulfonyl, sulfamoyl, monocyclic or dicyclic aroyl, aralkanoyl, arylalkenoyl, carbaralkoxy, arylsulfonyl, or the like, in which the aryl part can be a heterocyclic group having nitrogen, oxygen, sulfur, or the like hetero atom. The aryl part may be mono- or di-cyclic and 5- or 6-membered homo- or hetero-aryl having heteroatoms selected from nitrogen, oxygen, sulfur, etc. Representative heteroaromatic group include pyrrolyl, furyl, thienyl, pyrazolyl, imidazolyl, oxazolyl, thiazolyl, triazolyl, oxadiazolyl, thiadiazolyl, tetrazolyl, thiatriazolyl, oxatriazolyl, pyridyl, pyronyl, thiopyronyl, pyrimidyl, pyrazinyl, pyridazinyl, triazinyl, indolyl, benzofuryl, benzothienyl, tetrazolopyridazinyl, purinyl, quinolyl, isoquinolyl, pyridopyridyl, benzopyronyl, etc.

The said groups may further have an unsaturation, hetero atom, substituent, etc. The substituent can be a carbon function (alkyl, alkenyl, alkylidene, alkynyl, aralkyl, aryl, carboxy, protected carboxy, carbamoyl, alkanoyl, alkenoyl, aralkanoyl, aroyl, aminoalkyl, cyano, etc.), nitrogen function (amino, hydrazinyl, azido, diazo, alkylamino, arylamino, acylated amino, alkylideneamino, imino, nitroso, nitro, etc.), oxygen function (hydroxy, alkoxy, aralkoxy, aryloxy, acyloxy, oxo, etc.), sulfur group (mercapto, alkylthio, arylthio, acylthio, thioxo, sulfinyl, sulfonyl, sulfo, protected sulfo, etc.), phosphorus function (phospho, etc.), halogen atom (fluorine, chlorine, bromine, iodine, etc.), and the like, and may form a ring.

The protective groups can be those for protection from an adverse change during the reactions: hydrocarbon group, acyl, alkylated silyl, alkoxysilyl, alkylphosphinyl, etc., for hydroxy, amino, mercapto, or the like; ester, acid anhydride, amide, hydrazide, or the like for carboxy or sulfo; and other conventional protective groups, especially those introduced or removed without adverse effect on other parts of the molecule.

Representative compounds of this invention include 7β-(3-oxotetrahydro-1,4-thiazin-2-yl)carboxamido-7α-methoxy-3-(1-methyltetrazol-5-yl)thiomethyl-1-dethia-1-oxa-3-cephem-4-carboxylic acid, 7β-(3-oxotetrahydro-1,4-thiazin-2-yl)carboxamido-7α-methoxy-3-(1-(2-hydroxyethyl)tetrazol-5-yl)thiomethyl-1-dethia-1-oxa-3-cephem-4-carboxylic acid, 7β-(3-oxotetrahydro-1,4-thiazin-2-yl)carboxamido-7α-methoxy-3-(1-cyanoethyltetrazol-5-yl)thiomethyl-1-dethia-1-oxa-3-cephem-4-carboxylic acid, 7β-(3-oxotetrahydro-1,4-thiazin-2-yl)carboxamido-7α-methoxy-3-(1-carboxymethyltetrazol-5-yl)thiomethyl-1-dethia-1-oxa-3-cephem-4-carboxylic acid, 7β-(3-oxotetrahydro-1,4-thiazin-2-yl)carboxamido-7α-methoxy-3-(1-carbamoylmethyltetrazol-5-yl)thiomethyl-1-dethia-1-oxa-3-cephem-4-carboxylic acid, and their sodium salt.

Compound (I) is antibacterial against aerobic or anaerobic and Gram-positive (Staphylococci, etc.) or Gram-negative (*Escherichia coli*, etc.) bacteria and is useful as a bacteriocidal or bacteriostatic human or veterinary medicine for preventing or treating infection, disinfectant, preservative, or antiperishable.

The Compound (I) is stable, has less side effects, and is superior due to its activity against bacteria resistant to other drugs, and its pharmacological characters (absorption, distribution, metabolism, excretion, etc.), especially its high blood level for a longer time.

For medical use, it is administered externally, orally, topically or by injecting to prevent or treat an infection caused by sensitive bacteria at a daily dose of 10 micrograms to 1 milligram externally, 0.2 to 5 gram intravenously, or 1 to 2 gram orally of Compound (I), if required formulating with conventional additives.

Such pharmaceutical preparation can be an ampoule, vial, powder, pellet, granule, capsule, tablet, dry syrup, suspension, solution, emulsion, ointment, injection, oral drug, inhalant, pap, ocular solution, nasal preparation, ear solution, trouche, suppository, spray, or the like for enteral, parenteral, topical, local application, etc. The carboxylic acid or its light metal salt as Compound (I) can be used as an intravenous injection, drip, intramuscular or subcutaneous injection (vial, ampoule, etc.), if required in admixture with an excipient (stabilizer, solubilizer, etc.). A pharmacological ester can be used orally (powder, pellet, granule, capsule, dry syrup, solution, tablet, suspension, etc.), externally, or topically (solution, ointment, emulsion, suppository, spray, etc.).

Compound (I) can also be used as a raw material for assaying sensitivity of bacteria or a starting material for synthesizing other antibacterial within or without the scope of this invention.

Compound (I) can be synthesized, for example, by the following methods.

(1) Salt formation

Compound (I) having a 4-carboxy or cephem nucleus can form a corresponding light metal salt by reacting with a base or by exchange reaction with a light metal salt or other carboxylic acid. The procedure can be those conventional in the art, e.g., by neutralizing the free acid with light metal hydrogen carbonate, or by treating with alkali metal lower carboxylate in a polar organic solvent (alcohol, ketone, ester, etc.) and then adding sparingly soluble solvent to separate objective salt. The reaction ends usually in 1 to 10 minutes at lower than 50° C. The time may be longer, if no side reaction occurs. Antibacterial preparations can be made by formulating thus produced salts as solid (crystals, powders, etc.) or by lyophilizing.

(2) Deprotection of carboxy-protecting groups

The following conventional deprotection of protected carboxy in Compound (I) gives Carboxy compound (I):

(a) Highly reactive esters, amides, or anhydrides as carboxy protecting groups can be deprotected in an aqueous solvent with an acid, base, buffer solution, or ion exchange resin. When the reactivity is insufficient, one can increase it in a conventional manner to deprotect more easily (by treatment of trichloroethyl, p-nitrobenzyl, phenacyl ester with metal and acid, catalytic hydrogenation, dithionate, etc.).

(b) Aralkyl esters can be deprotected by catalytic reduction. The reaction can be done conventionally with hydrogen in the presence of a catalyst (palladium, nickel, etc.).

(c) Aralkyl, cyclopropylmethyl, sulfonylethyl, etc. esters can be deprotected by solvolyzing [with mineral acid, Lewis acid sulfonic acid, strong carboxylic acid, etc.], if required in the presence of a cation scavenger.

(d) Phenacyl, alkenyl, hydroxyaralkyl, etc. esters can be deprotected with a base or nucleophilic reagent. Photochemically active phenacyl esters are deprotected by irradiation.

(e) 2-Alkenyl ester is deprotected with an alkali metal alkanoate and palladium-triphenylphosphine complex giving an alkali metal salt.

(f) and other equivalent carboxy deprotections.

(3) Introduction of the 3-substituent

Compounds (I) having 3-methyl substituted by a leaving group or atom can be treated with heteroaromatic thiol, aromatic base or its reactive derivative giving the objective compound (I). Here the leaving group is preferably reactive halogen, sulfonyloxy, alkanoyloxy, etc. Preferable reactive derivatives of said thiol are alkali metal salts, ammonium salt, carboxylate thiol ester, etc. The reaction goes at 0° to 60° C. even in anhydrous or aqueous solvent. This reaction is accelerated with a dehydrating reagent, phosphoryl chlorides, rhodanates, etc.

Compounds (I) having carbamoyloxymethyl at position 3 can be produced by reacting the 4-carboxy protected 3-hydroxymethyl compound (I) with a reactive derivative of N-protected carbamic acid and the product is deprotected keeping the carbamoyloxy group.

(4) Amidation

A reaction of Amine (II) or its reactive derivative with Carboxylic acid (III) or its reactive derivative gives Amide

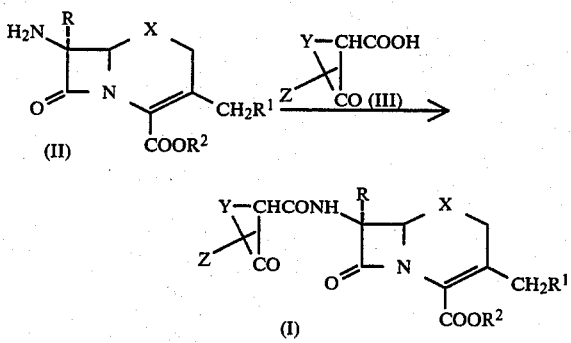

(I) or its derivatives.

The reactive derivative of Amine (II) is that having 7-amino activated by silyl (trimethylsilyl, methoxydimethylsilyl, t-butyldimethylsilyl, etc.), stannyl (trimethylstannyl, etc.), alkylene (as a part of enamino of the amino with aldehyde, acetone, acetylacetone, acetoacetate, acetoacetonitrile, acetoacetanilide, cyclopentanedione, acetylbutyrolactone, etc.), alkylidene (1-haloalkylidene, 1-haloaralkylidene, 1-alkoxyalkylidene, 1-aralkoxyalkylidene, 1-alkoxy-1-phenoxyalkylidene, alkylidene, aralkylidene, etc.), acid (mineral acid, carboxylic acid, sulfonic acid, etc. as a salt of the amino), etc.), or the like, or that protected at other functions of the molecule.

The reactive derivatives of Carboxylic acid (III) can be an acid anhydride, halide, reactive ester, reactive amide, azide, or the like conventional derivative for acylation.

Following are some reagents and procedures for said amidation.

(i) Free acid (III)—In the presence of a condensing reagent [carbodiimide (N,N'-diethylcarbodiimide, N,N'-dicyclohexylcarbodiimide, etc.), carbonyl compound (carbonyl diimidazole, etc.), isoxazolinium salt, acylamino compound (2-ethoxy-1-ethoxycarbonyl-1,2-dihydroquinoline, etc.), amidase, etc.], Amine (II) is treated with Carboxylic acid (III) preferably in an aprotic solvent (halohydrocarbon, nitrile, ether, amide, etc. solvent or the mixture), preferably 1 to 2 molar equivalents of Carboxylic acid (III) and 1 to 2 molar equivalents of the condensing reagent against Amine (II).

(ii) Acid anhydride—This includes a symmetric anhydride and mixed anhydride of Carboxylic acid (III) [with mineral acid (phosphoric acid, sulfuric acid, carbonic half ester, etc.), organic acid (alkanoic acid, aralkanoic acid, sulfonic acid, etc.), or hydrohalogenic acid (i.e., acid halide)] intramolecular anhydride (ketene, isocyanate, etc.), and of Carboxylic acid (III). Preferably, Amine (II) or its reactive derivative is amidated with 1 to 2 molar equivalents of the acid anhydride in the presence of 0 to 1 molar equivalent of an acid scavenger [inorganic base (oxide, hydroxide, carbonate, hydrogen carbonate, etc. of alkali metal or alkaline earth metal, etc.), organic base (tertiary amine, aromatic base, etc.); oxirane (alkylene oxide, aralkylene oxide, etc.); pyridinium salt (tripyridiniumtriazine trichloride, etc.); adsorbing agent (Celite, etc.); or the like], preferably in an aprotic solvent (halohydrocarbon, nitrile, ether, amide, etc., solvent or a mixture) thereof.

(iii) Acid halide—This is a mixed anhydride of Carboxylic acid (III) with hydrogen halide. Thus, 1 to 2 molar equivalents of this acid halide is preferably reacted with 1 molar equivalent of Amine (II) or its reactive derivative as given above item (ii) in the presence of 1 to 10 molar equivalents of the said acid scavenger in a solvent (halohydrocarbon, nitrile, ether, ester, ketone, dialkylamide, water, or the like solvent or a mixture thereof).

(iv) Reactive ester—This includes an enol ester (vinyl ester, isopropenyl ester, etc.), aryl ester (phenyl ester, halophenyl ester, nitrophenyl ester, etc.), heterocyclic ester (1-hydroxybenzotriazole ester, etc.), an ester with N-hydroxy compound, diacylhydroxylamine ester, thioester, or the like having conventional reactive ester group. This is used as described below. Enzymatically reactive esters (lower alkyl ester, etc.) can be used conventionally in an aqueous solvent in the presence of an amidase.

(v) Reactive amide—This includes an aromatic amide (amide with imidazole, triazole, 2-ethoxy-1,2-dihydroquinoline, etc.), diacylanilide, or the like of Acid (III) treated as given below and (vi) Formimino compond (N,N-dimethylformimino ester halide, etc.) of Acid (III).

The reactions from (iv) to (vi) are carried out by treating 1 molar equivalent of Amine (II) or its reactive derivative with 1 to 2 molar equivalents of Carboxylic acid (III) or its reactive derivative in an aprotic solvent (halohydrocarbon, ether, ketone, nitrile, amide, ester, etc. solvents or mixture) for 1 to 5 hours at $-20°$ C. to $40°$ C.

(5) Methoxylation

Compounds of the formula (I) but having 7-hydrogen are treated with an N-halogenating reagent, dehydrohalogenating reagent, and methanol to give the corresponding Compound (I) from either 7-alpha- or 7-beta-hydrogen compound.

The procedure is, for example, as follows:
(a) Reacting with alkyl hypochlorite (t-butyl hypochlorite, etc.) and alkali metal methoxide (lithium methylate, sodium methylat, etc.) in methanol.
(b) Reacting with molecular halogen and a base (metal alkoxide e.g. lithium methoxide, sodium methoxide, magnesium methoxide, DBU (1,5-diazabicyclo[5,4,0]-5-undecene), triethylamine, picoline, etc.) in methanol.
(c) Reacting with N-halogenating reagent (hypohalite salt, hypohalite ester, N-haloamide, N-haloimide, etc.) and dehydrohalogenating reagent (alkali metal alkoxide, aryl alkali metal, etc.), and then treating with methanol.

(6) Protection of carboxy or other reactive functions

When Compound (I) is subjected to a chemical reaction to make other Compounds (I), functional groups other than the objective group are sometimes protected by conventional methods in the art as given in various literature, etc.

Protection and deprotection of said functional groups are described in, e.g., J. F. W. McOmie Ed., "Protective Groups in Organic Chemistry", p. 183 (1973), Pleum Press, N.Y.; S. Patai, Ed. "The Chemistry of Functional Groups", p. 505 (1969), Interscience Publ., John Wiely & Sons Ltd., London; Flynn ed., "Cephalosporins and Penicillins", Academic Press, N.Y., (1972); and the like books or patent literature.

For example, hydroxy is protected by acylation, etherification, etc.; amino is protected by acylation, enamine formation, silyl introduction, etc.; carboxy is protected by esterification, amidation, acid anhydride formation, etc.; each in a conventional manner. Introduction of physiologically active ester to improve pharmacological character is also included in this reaction, e.g., by treating Carboxylic acid (I) with a base to form a salt and then with halide to give the objective ester (I).

(7) Reaction Conditions

The said reactions (1) to (6) can usually be carried out conventionally in an inert solvent at $-30°$ C. to $100°$ C., preferably at $-20°$ C. to $50°$ C. for 10 minutes to 5 hours in a solvent, if required in a dry condition. The reaction solvent can be a hydrocarbon, halohydrocarbon, ether, ketone, ester, nitrohydrocarbon, nitrile, amide, sulfoxide, carboxylic acid, organic base, alcohol, water, or the like industrial solvent or the mixture.

(8) Work up

The products can be obtained from the reaction mixture by removing contaminants (solvents, unreacted starting materials, by-products, etc.) by conventional extracting, evaporating, washing, drying, etc., and isolating the product by usual work up (adsorbing, eluting, distilling, precipitating, separating, chromatographing, etc.).

(9) Examples and Preparations

Following examples illustrate the embodiments of this invention.

Physicochemical constants of the products are summarized in the Tables. In the Tables, IR shows $cm^{-1}$ values, NMR shows δ-values and J values show coupling constants in Hz scale. In the Examples, "part" shows part by weight and "equivalent" shows molar equivalent each of the beta-lactam starting material.

Work-up procedure is usually as follows:

The reaction mixture is, if required after addition of solvent, (water, dichloromethane, etc.), washed with water, dried, and vacuum concentrated. Residue is crystallized, precipitated, or filtrated, if required after silica gel chromatography. Physical constants of the product are identified with those of authentic samples.

Abbreviations used are as follows:

BH is for benzhydryl, Me is for methyl, Et is for ethyl, PMB is for p-methoxybenzyl, Ftdyl is for phthalidyl, STet is for 5-sulfidotetrazol-1-yl, Ph is for phenyl, POM is for pivaloyloxymethyl, AOM is for acetoxymethyl, and BAK is for 1-(ethoxycarbonyloxy)ethyl.

Preparation 1

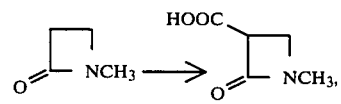

Into tetrahydrofuran (20 ml) containing diisopropylamine (1.82 ml) is added 15% n-butyllithium-hexane (7.5 ml), and the mixture is stirred for 25 minutes. To this solution are added 1-methyl-2-azetidinone dropwise at $-70°$ C. and after 20 minutes, diethyl carbonate (1.33 ml). After 2.5 hours stirring, reaction mixture is quenched with 10% hydrochloric acid (15 ml) and extracted with ethyl acetate. The solvent is evaporated to give 1-methyl-2-oxoazetidine-3-carboxylic acid ethyl ester (476 mg). Colorless oil.

IR (CHCl$_3$) ν: 1760, 1725 cm$^{-1}$.

This is hydrolyzed with 1N-sodium hydroxide in acetone (5 parts by weight). The acid part is taken to give the corresponding carboxylic acid. Colorless oil.

NMR (CDCl$_3$) δ: 2.88 (s, 3H), 3.33–3.65 (m, 2H), 4.6–4.25 (m, 1H).

Preparation 2

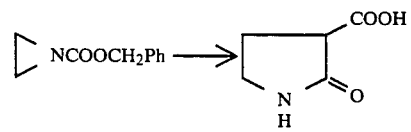

To a solution of sodiomalonic acid diethyl ester prepared from sodium hydride (704 mg), diethyl malonate (3 ml), and tetrahydrofuran (10 ml) is added aziridine-1-carboxylic acid benzyl ester (1.8 g). After 22 hours at room temperature, the mixture is neutralized with 10% phosphoric acid, washed with water, dried and concentrated to give 1-carbobenzoxy-2-oxopyrroidine-3-carboxylic acid ethyl ester (1.85 g). Oil. IR (CHCl$_3$) ν: 1785, 1730 cm$^{-1}$.

This product is hydrogenolyzed with 10% palladium charcoal in ethanol to give 2-oxopyrrolidin-3-carboxylic acid ethyl ester. mp. 74.5°–75.5° C. IR (CHCl$_3$) ν: 3440, 1735, 1710 cm$^{-1}$.

This is hydrolyzed with 1N-sodium hydroxide at room temperature for 30 minutes to give 2-oxopyrrolidine-3-carboxylic acid. mp 122°–127° C.

Preparation 3

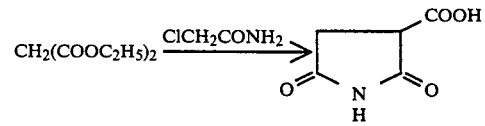

To a solution of diethyl malonate (6.1 ml) in N,N-dimethylformamide (30 ml) are added 60% sodium hydride (1.6 g) at 0° C. and, after 8 minutes, chloroacetamide (1.87 g). After stirring at room temperature for 3.5 hours, the mixture in neutralized with acetic acid and extracted with ethyl acetate. The extract is washed with water and concentrated to give 2,5-dioxopyrrolidine-3-carboxylic acid ethyl ester. Oil.

NMR (CDCl$_3$) δ: 1.33 (t, 3H, 7 Hz), 4.28 (q, 2H, 7 Hz), 9.03 (brs, 1H).

This is hydrolyzed with 1N-sodium hydroxide. The acid fraction is washed with water and concentrated to give 2,5-dioxopyrrolidine-3-carboxylic acid. mp. 120°-126° C. (decomp.).

Preparation 4

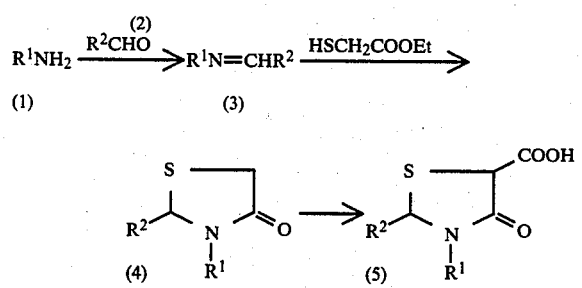

Amine (1) (1 equivalent) and Aldehyde (2) (1 equivalent) are reacted under cooling for 1 to 5 hours. Product Imine (3) in toluene is treated with thioglycolic acid (1 equivalent) and 1/100 parts by weight of p-toluenesulfonic acid monohydrate for 1 to 30 hours, washed with water, and concentrated to give thiazolidine (4). This is tetrahydrofuran (10 parts) is treated with ethyl chloroformate (1 equivalent) in the presence of lithium diisopropylamide (2 equivalents) at −70° C. to −20° C. for 0.1 to 1 hour to give thiazolinonecarboxylic acid ethyl ester (5-ethyl ester). This is hydrolyzed with 1N-sodium hydroxide in ethanol at 0° C. to 30° C. to give 2-oxothiazolidine-5-carboxylic acid (5).

IR absorption spectra of said products are listed in the next Table.

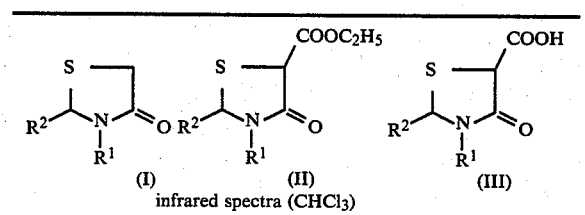

infrared spectra (CHCl3)

| a | R¹ | R² | I | II | III |
|---|---|---|---|---|---|
| a | CH3 | H | — | 1730, 1685 | NMR 3.03, s, 3H |
| b | CH3 | CH3 | 1665 | 1740, 1685 | 1765, 1730, 1680 |
| c | CH3 | C2H5 | 1675 | 1730, 1675 | NMR 1.00, t, 3H, 7 Hz; 2.97, s, 3H |
| d | C2H5 | H | — | 1740, 1690 | mp 114° C. |
| e | n-C3H7 | H | — | 1760, 1690 | NMR 0.93 (t, 3H, 7Hz), 3.40 (t, 2H, 7Hz) |
| f | n-C3H7 | CH3 | 1670 | 1740, 1680 | 1765, 1725, 1625 |
| g | —CH2CH2— \| \| H O | H | THP ether 3420, 1670 | THP ether 1675 | 1730, 1685 |
| i | —CH3 | Ph | 1680 | — | 1730, 1680 |

Preparation 5

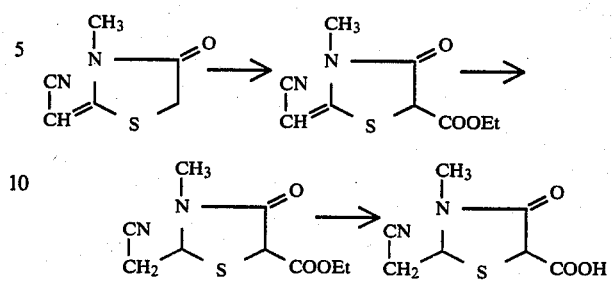

A solution of lithium diisopropylamide prepared from diisopropylamine (336 μl) and 16% n-butyllithium in hexane (1.5 ml) is diluted with tetrahydrofuran (20 ml). This solution is dropwise added to a solution of 3-methyl-2,2-cyanomethylenethiazolidin-4-one (308 mg) in tetrahydrofuran (4 ml) cooling at −70° C. After 5 minutes, ethyl chloroformate (228 μl) is added to the mixed solution. After 30 minutes, the reaction mixture is warmed to 0° C., neutralized with acetic acid, and concentrated. The residue is diluted with ethyl acetate, washed with water, and concentrated to give 3-methyl-2,2-cyanomethylene-4-oxothiazolidine-5-carboxylic acid ethyl ester (105 mg). NMR (CDCl3)δ: 1.30 (t, 3H, 7 Hz,), 3.17 (s, 3H), 4.28 (q, 2H, 7 Hz), 4.80 (s, 1H), 4.87 (s, 1H).

This (435 mg) in methanol (20 ml) is treated with trace amount of iodine and magnesium (1.1 g) at 0° C. for 30 minutes. After 3.5 hours' stirring at room temperature, the reaction mixture is acidified with hydrochloric acid and extrated with ethyl acetate. The extract is washed with water, dried, and concentrated to give 2-cyanomethyl-3-methyl-4-oxothiazolidine-5-carboxylic acid ethyl ester (282 mg).

IR (CHCl3) ν: 2960, 2240, 1730, 1685 cm⁻¹.

NMR (CDCl3) ν: 1.32 (t, 3H, 7 Hz), 3.07 (s, 3H), 3.13 (d, 2H, 9 Hz), 4.25 (q, 2H, 7 Hz), 4.35 (s, 1H), 4.7–5.0 (m, 1H).

This in ethanol (3 ml) is stirred with 1N-sodium hydroxide (3 ml) at 0° C. for 45 minutes. The mixture is neutralized with diluted hydrochloric acid and extracted with ethyl acetate. The extract is washed with water, dried, and concentrated to give 2-cyanomethyl-3-methyl-4-oxothiazolidine-4-carboxylic acid (197 mg).

Preparation 6

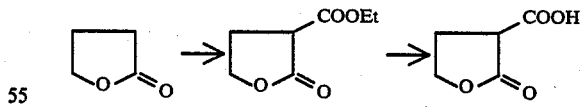

A solution of lithium diisopropylamide prepared from diisopropylamine (3.64 ml) and n-butyllithium (1.6M hexane solution) (16 ml) in tetrahydrofuran (40 ml) is mixed at −70° C. with gamma-butyrolactone (1.54 ml) over 45 minutes period and then ethyl chloroformate (1.8 ml). After 60 minutes' stirring, the reaction mixture is neutralized with hydrochloric acid, concentrated, and diluted with ethyl acetate, washed, and concentrated to give gamma-butyrolactone-α-carboxylic acid ethyl ester (1.355 g).

NMR (CDCl3) δ: 1.32 (t, 3H, 7 Hz), 3.57 (dd, 1H, 7 Hz, 10 Hz), 4.27 (q, 2H, 7 Hz).

This (316 mg) in 1N-sodium hydroxide (4 ml) is stirred at 0° C. for 80 minutes, neutralized with hydrochloric acid, concentrated, and extracted with ether. The extract is concentrated to give gamma-butyrolactone-α-carboxylic acid (260 mg).

Preparation 7

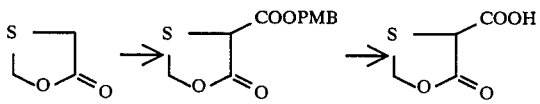

A mixture of thioglycolic acid (14 ml), paraformaldehyde (9.0 g), and p-toluenesulfonic acid monohydrate (0.4 g) is let stand overnight. The mixture is distilled to give 5-oxo-1,3-oxathiolane (3.14 g). bp (15 mmHg) 85° C.

NMR (CDCl$_3$) δ: 3.60 (s, 2H), 5.23 (s, 2H).

A solution of lithium diisopropylamide prepared from diisopropylamine (3.1 ml), n-butyllithium (14 ml as 1.6M hexane solution) and tetrahydrofuran (40 ml) is cooled at −70° C., mixed with 5-oxo-1,3-oxathiolane (1.04 g) and p-methoxybenzyl chloroformate. After 30 minutes, the mixture is acidified with hydrochloric acid, concentrated, and extracted with ethyl acetate. The extract is washed with water, dried, and concentrated to give 5-oxo-1,3-oxathiolane-4-carboxylic acid p-methoxybenzyl ester (265 mg).

NMR (CDCl$_3$) δ: 3.78 (s, 3H), 4.35 (s, 1H), 5.11 (s, 2H), 5.18; 5.35 (ABq, 2H, 6 Hz), 6.80; 7.25 (dd, 4H, 8 Hz).

This is dissolved in a mixture of dichloromethane (2 ml), anisole (0.5 ml), and trifluoroacetic acid (0.5 ml). After 90 minutes at 0° C., the mixture is concentrated, and triturated in n-hexane to give 5-oxo-1,3-oxathiolane-4-carboxylic acid (265 mg).

NMR (CDCl$_3$) δ: 4.47 (s, 1H), 5.27; 5.43 (ABq, 2H, 6 Hz).

Preparation 8

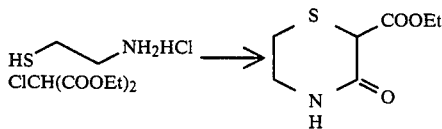

To a stirred mixture of thioethanolamine hydrochloride (1.14 g), ethyl chloromalonate (1.6 ml), and ethanol (20 ml) cooled at 0° C. is added dropwise 1N-sodium ethoxide in ethanol (20 ml). After 2 hours, the mixture is neutralized with ethanolic hydrochloric acid and concentrated. The residue is stirred in dichloromethane, filtered to remove solid, and concentrated. The residue is recrystallized from ethyl acetate to give 3-oxo-2H-3,4,5,6-tetrahydro-1,4-thiazine-2-carboxylic acid ethyl ester (970 mg). mp. 95°-97° C.

IR (CHCl$_3$) ν: 3390, 1730, 1670 cm$^{-1}$.

Preparation 9

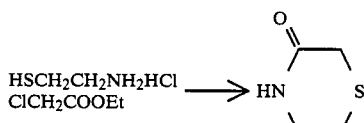

To a solution of thioethanolamine hydrochloride (4.54 g) and ethyl chloroacetate (3.52 ml) in ethanol (100 ml) is added triethylamine (12.3 ml) dropwise. After refluxing for 4 hours, the mixture is concentrated. The residue is stirred in ethyl acetate, filtered to remove solid, and concentrated to give thiomorpholine-3-one (3.48 g).

NMR (CDCl$_3$) δ: 3.27 (s, 2H).

Preparation 10

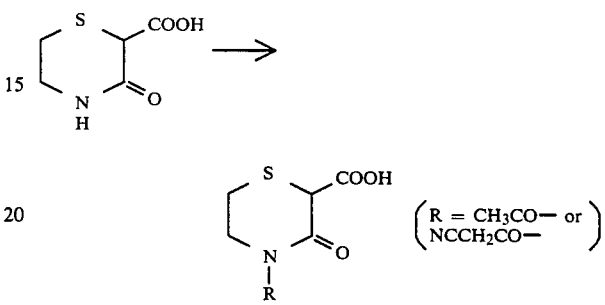

3-Oxomorpholine-2-carboxylic acid is esterified in dichloromethane with diphenyldiazomethane (1 equivalent) to give the corresponding diphenylmethyl ester.

This ester (327 mg) in dichloromethane (2 ml) is mixed with O,N-bistrimethylsilyltrifluoroacetamide (1.1 ml) and acetyl chloride (0.28 ml). After 2 hours' stirring at room temperature, the mixture is concentrated. The residue is dissolved in ethyl acetate, washed with water, dried, and concentrated to give 1-acetyl-3-oxothiomorpholine-2-carboxylic acid diphenylmethyl ester (302 mg).

IR (CHCl$_3$) ν: 1710 cm$^{-1}$.

This acetyl compound (302 mg) is mixed with dichloromethane (2 ml), anisole (0.5 ml), and trifluoroacetic acid (0.5 ml). After 1 hours's stirring, the mixture is concentrated, concentrated, and triturated in petroleum ether to give 4-acetyl-3-oxothiomorpholine-2-carboxylic acid. This can be used for amidating 7-amino-1-dethia-1-oxa-3-cephem 4-carboxylic acid ester without further purification.

Similarly, 4-cyanoacetyl-3-oxothiomorpholine-2-carboxylic acid benzhydryl ester (IR (CHCl$_3$) ν: 1710 cm$^{-1}$) is prepared and deprotected to give 4-cyanoacetyl-3-oxothiomorpholine-2-carboxylic acid.

Preparation 11

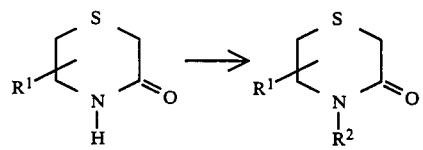

A solution of 3-oxothiomorpholine (1 equivalent) and sodium hydride (1 equivalent) in N,N-dimethylformamide or tetrahydrofuran (10 parts) is stirred at −10° C. for 1 hour, mixed with alkyl iodide or alkyl sulfate (1.0–1.4 equivalents), and stirred at −10° to 10° C. for 2 hours. The mixture is neutralized with 10% hydrochloric acid, concentrated, diluted with ethyl acetate, washed with water, dried, and concentrated to give 4-alkyl-1,4-thiomorpholin-3-one in 80 to 90% yield.

Physical constants of the products are listed in Table 1

TABLE 1

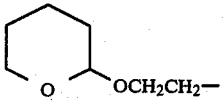

N—Alkylthio morpholin-3-one

| $R^1$ | $R^2$ | NMR: $\delta^{CDCl_3}$ ppm |
|---|---|---|
| H | $CH_3-$ | 2.70~2.97(m,2H), 2.98(s,3H),3.28 (s,2H). |
| H | $C_2H_5-$ | 1.13(t,3H,7Hz), 3.30(s,2H),3.47 (q,2H,7Hz). |
| H | $n-C_3H_7-$ | 0.93(t,3H,7Hz), 1.27~1.87(m,2H), 3.30(s,2H). |
| H | $i-C_3H_7-$ | 1.12(d,6H,7Hz), 3.27(s,2H),4.87 (septet,1H,7Hz). |
| H | (tetrahydropyranyl)-OCH$_2$CH$_2-$ | 1.28~2.08(m,6H), 2.78~3.05(m,2H), 3.30(s,2H). |
| H | $CH_3OCH_2$ | 3.33(s,2H),4.38~ 4.75(m,2H),4.87 (s,1H). |
| H | $t-C_4H_9O_2COCH_2-$ | 1.47(s,9H),3.37 (s,2H),4.08(s,2H). |
| H | $PhCH_2-$ | 3.47(s,2H),4.63 (s,2H),7.27(s,5H). |
| $5-CH_3-$ | $CH_3-$ | 1.30(t,3H,7Hz),2.43 (s,3H),3.23(s,2H), 4.20(q,2H,7Hz). |
| $6-CH_3$ | $CH_3-$ | 1.30(d,3H,6Hz), 3.00(s,3H),3.30 (s,2H),3.13~3.77 (m,3H). |
| 6-Ph | $CH_3-$ | 2.98(s,3H),3.45 (s,2H),3.75(d,2H, 7Hz),4.35(t,1H, 7Hz),7.38(s,5H). |
| 5-NC\|H$_2$C— | $CH_3-$ | 3.03(s,3H),2.7~ 3.7(m,6H),3.83~ 4.18(m,1H). mp. 71~72° C. |
| 5-O= | $CH_3-$ | 3.20(s,3H),3.55 (s,4H) mp. 55~56° C. |

Preparation 12 (Part 1)

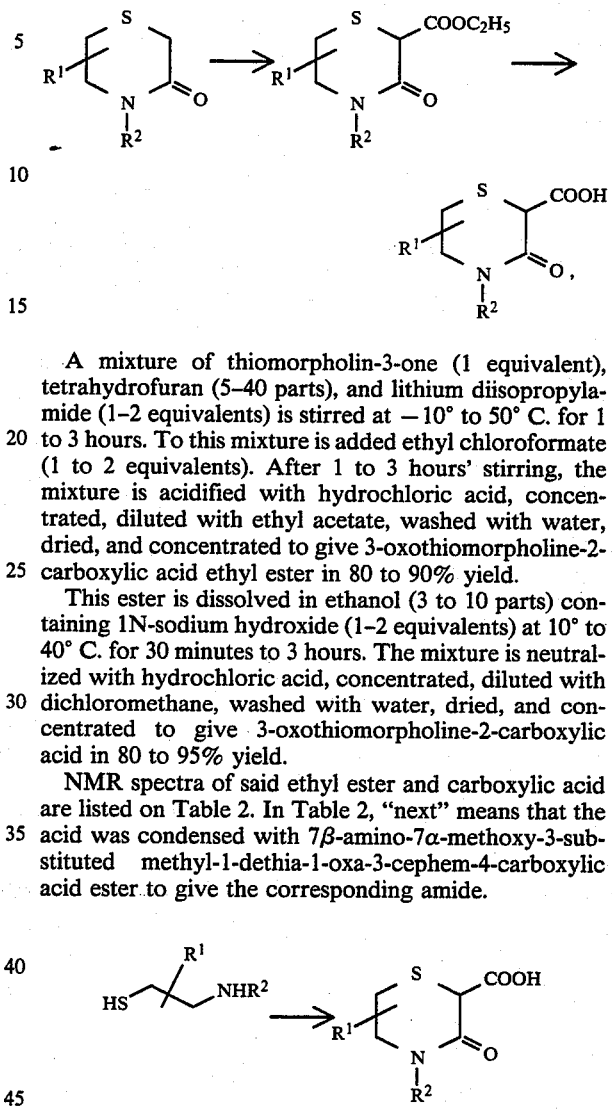

A mixture of thiomorpholin-3-one (1 equivalent), tetrahydrofuran (5-40 parts), and lithium diisopropylamide (1-2 equivalents) is stirred at −10° to 50° C. for 1 to 3 hours. To this mixture is added ethyl chloroformate (1 to 2 equivalents). After 1 to 3 hours' stirring, the mixture is acidified with hydrochloric acid, concentrated, diluted with ethyl acetate, washed with water, dried, and concentrated to give 3-oxothiomorpholine-2-carboxylic acid ethyl ester in 80 to 90% yield.

This ester is dissolved in ethanol (3 to 10 parts) containing 1N-sodium hydroxide (1-2 equivalents) at 10° to 40° C. for 30 minutes to 3 hours. The mixture is neutralized with hydrochloric acid, concentrated, diluted with dichloromethane, washed with water, dried, and concentrated to give 3-oxothiomorpholine-2-carboxylic acid in 80 to 95% yield.

NMR spectra of said ethyl ester and carboxylic acid are listed on Table 2. In Table 2, "next" means that the acid was condensed with 7β-amino-7α-methoxy-3-substituted methyl-1-dethia-1-oxa-3-cephem-4-carboxylic acid ester to give the corresponding amide.

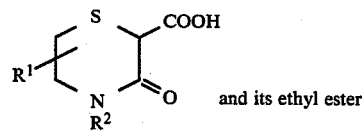

The same compounds can also be produced by reaction of N-alkylcysteamine with chloromalonic acid ester and hydrolysis.

TABLE 2 and its ethyl ester

| | | NMR: $\delta^{CDCl_3}_{ppm}$ | |
|---|---|---|---|
| $R^1$ | $R^2$ | ethyl ester | acid |
| H | H— | 1.33(t, 3H, 7Hz), 4.08(s, 1H), 4.28(q, 2H, 7Hz) | |
| H | $CH_3-$ | 3.05(s, 3H), 1.30(t, 3H, 7Hz) | 3.05 (s, 3H) |
| H | $C_2H_5-$ | 1.20(t, 3H, 8Hz), 1.30(t, 3H, 7Hz) | next |
| H | $n-C_3H_7-$ | 0.93(t, 3H, 7Hz), 1.30(t, 3H, 7Hz) | next |

TABLE 2-continued

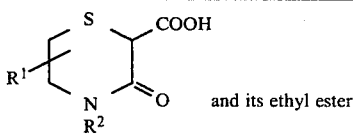

and its ethyl ester

NMR: $\delta^{CDCl_3}_{ppm}$

| R¹ | R² | ethyl ester | acid |
|---|---|---|---|
| H | i-C₃H₇— | 1.15(d, 6H, 7Hz), 1.30(t, 3H, 7Hz) | next |
| H |  | 1.30(t, 3H, 7Hz) | next |
| H | CH₃OCH₂— | 1.32(t, 3H, 7Hz), 3.37(s, 3H) | next |
| H | t-C₄H₉<br>\|<br>OCOCH₂— | 1.30(t, 3H, 8Hz), 1.47(s, 9H) | next |
| H | PhCH₂— | 4.37; 5.00(ABq, 2H, 15Hz) | next |
| 5-CH₃— | H | 1.30(t, 3H, 7Hz), 1.30(d, 3H, 7Hz), 4.25(q, 2H, 7Hz) | |
| 5-CH₃— | CH₃— | 1.30(t, 3H, 7Hz), 4.23(q, 2H, 7Hz) | 1.47 (d, 3H, 6Hz), 4.07(s, 1H) |
| 6-CH₃ | CH₃— | 1.32(t, 3H, 7Hz), 1.28(d, 3H, 6Hz) | 2.82(s, 3H), 1.23(bs, 3H) |
| 6-Ph | CH₃— | 1.32(t, 3H, 7Hz), 3.03(s, 3H), 4.22(s, 1H) | 3.03(s, 3H), 7.38(s, 5H) |
| CN<br>\|<br>5-CH₂— | CH₃— | 1.32(t,3H,7Hz),4.27(q, 2H,7Hz) | 3.00(s,3H), 4.65(s,2H) |
| H | —CH₂CONH₂ | IR: $\nu^{CHCl_3}_{max}$ 3480, 3360, 1710, 1690, 1655 cm⁻¹ | next |
| H | —CH₂CN | 1.30(t, 3H, 7Hz), 2.65∼2.93(m, 1H), 3.15∼3.51(m, 1H), 3.71∼3.93(m, 2H), 4.26 (q, 2H, 7Hz), 4.15(s, 1H), 4.26 ∼4.55(2H, ABq, 17Hz) | next |

Preparation 12 (Part 2)

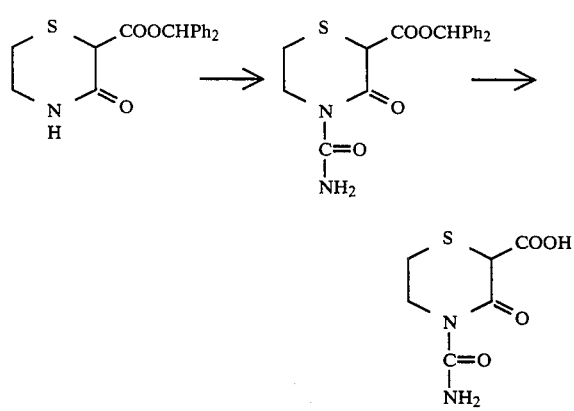

To a mixture of 2-diphenylmethoxycarbonyl-3-oxo-thiomorpholine (327 mg, 1 mM), dichloromethane (8 ml), and bistrimethylsilyltrifluoroacetamide (0.53 ml). After 30 minutes' stirring from addition of trichloroacetyl isocyanate (0.18 ml), another trichloroacetyl isocyanate (0.06 ml) is added. After another 30 minutes' stirring, the mixture is concentrated and subjected to silica gel chromatography. Fractions eluted with dichloromethane and a mixture of dichloromethane and ethyl acetate (9:1) are combined and concentrated to give 2-diphenylmethoxycarbonyl-4-carbamoyl-3-oxothiomorpholine (332 mg). Yield 89.6%.

IR (CHCl₃) ν: 3490, 3400, 1730 cm⁻¹.

NMR (CDCl₃) δ: 2.71–3.20 (m, 2H), 3.32–4.72 (m, 2H), 4.48 (s, 1H), 6.90 (s, 1H), 7.03–7.63 (m, 10H).

This diphenylmethyl ester is mixed with dichloromethane (3 ml), anisole (1 ml), and trifluoroacetic acid (1.5 ml) under ice cooling. After 1 hour's stirring, the reaction mixture is concentrated and washed with n-hexane. Resulting carboxylic acid is condensed with 7β-amino-7α-methoxy-3-substituted methyl-1-dethia-1-oxa-3-cephem-4-carboxylic acid ester without measuring physical constants.

Preparation 13

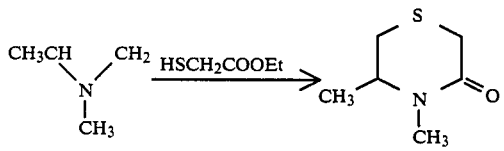

Mixing of N-methylpropyleneimine (1.2 g) and ethyl thioglycolate (1.52 ml) affords 2-(2-methylaminopropyl)thioacetic acid ethyl ester immediately.

IR (film) ν: 1730, 1630 cm$^{-1}$.

This is dissolved in 1M sodium ethylate ethanol solution (14 ml) and refluxed for 15 minutes. The mixture is acidified with hydrochloric acid and extracted with ethyl acetate. The extract is washed with water, dried, and concentrated to give 4,5-dimethyl-3-oxothiomorpholine (1.55 g).

NMR (CDCl$_3$) δ: 1.42 (d, 3H, 7 Hz), 2.52–3.15 (m, 2H), 2.97 (s, 3H), 3.17; 3.43 (ABq, 2H, 16 Hz).

Preparation 14

PhCH=CHNO$_2$ ⟶ PhCHCH$_2$NO$_2$ ⟶
       |
       SCH$_2$CO$_2$Et

[Ph-substituted 3-oxothiomorpholine structure]

To a solution of beta-nitrostyrene (447 mg) in ether (10 ml) are added triethylamine (42 l) and ethyl thioglycolate (0.33 ml). After 30 minutes' stirring, the mixture is concentrated to give (1-phenyl-2-nitroethyl)thioacetic acid ethyl ester (718 mg).

NMR (CDCl$_3$) δ: 1.27 (t, 3H, 7 Hz), 3.08 (s, 2H), 4.15 (q, 2H, 7 Hz), 4.82 (s, 3H), 7.35 (s, 5H).

The product (1.08 g) is reduced with iron powder (1.15 g) in acetic acid to give 6-phenyl-3-oxothiomorpholine (246 mg).

NMR (CDCl$_3$) δ: 3.40 (s, 2H), 4.28 (t, 1H, 7 Hz), 7.33 (s, 5H).

Preparation 15

CH$_3$NO$_2$ + CH$_3$CHO ⟶ CH$_3$CHOH ⟶ CH$_3$CHOCOCH$_3$
                              |                    |
                              CH$_2$NO$_2$         CH$_2$NO$_2$
                                                        ↓
[6-methyl-3-oxothiomorpholine structure]  ⟵  CH$_3$CHSCH$_2$COOEt
                                                |
                                                CH$_2$NO$_2$ A solution of nitromethane (10.8 ml) in ethanol (10 ml) is mixed with 10N-sodium hydroxide (0.8 ml), water (1.5 ml), and acetaldehyde (11.2 ml). After one day, the mixture is distilled to give 1-nitro-2-propanol (9.70 g).

bp. (3 mmHg): 67°–70° C.

This is refluxed with acetyl chloride (15 ml) for 3 hours, concentrated, and then distilled to give 2-acetoxynitropropane (8.74 g).

bp (7 mmHg): 70° C.

To a mixture of methanol (40 ml), sodium (2.25 g), ethyl thioglycolate (9.8 ml), and methanol (20 ml) is added dropwise a solution of 2-acetoxynitropropane (8.74 g) in methanol (20 ml). After 2 days, the mixture is concentrated, diluted with ether, washed with water, dried, and distilled to give (1-nitro-2-propyl)thioacetic acid ethyl ester (5.69 g).

bp (1–2 mmHg): 105°–111° C.

Iron powder (7.35 g) is activated by refluxing in water containing acetic acid (0.64 g) for 1 hour. To this solution is added (1-nitro-2-propyl)thioacetic acid ethyl ester (4.92 g) and ethanol (6 ml). After refluxing overnight, the mixture is filtered to remove solid, concentrated, diluted with ethyl acetate, washed with water, dried, and concentrated to give 6-methyl-3-oxothiomorpholine (1.37 g).

NMR (CDCl$_3$) δ: 1.30 (d, 3H, 6 Hz), 3.30 (s, 2H).

Preparation 16

NCCH=CHCH$_2$Br + CH$_3$NHCOCH$_2$SH ⟶

NCCH=CHCH$_2$
      |
      CH$_3$NHCOCH$_2$S  ⟶

[5-cyanomethyl-4-methyl-3-oxothiomorpholine structure]

To a solution of omega-cyano-allyl bromide (9.07 g) in tetrahydrofurane (60 ml) cooled at −65° C. is added a mixture of triethylamine (9.5 ml) and thioglycolic methylamide (6.13 ml). After 15 minutes, cooling is stopped and the mixture is warmed to 0° C. The mixture is diluted with water and extracted with ethyl acetate. The extract is washed with water, dried, and concentrated to give 5-cyanomethyl-4-methyl-3-oxothiomorpholine (6.86 g).

IR (CHCl$_3$) ν: 3400, 2230, 1670 cm$^{-1}$.

Preparation 17

EtOOC
      \
       ⟩—CONH$_2$ ⟶ [2,6-dioxopiperidine-3-carboxylic acid structure]
      /
EtOOC To a solution of diethyl malonate (2.3 ml) in tetrahydrofuran (2.3 ml) cooled at 0° C. is added sodium hydride (400 mg). After stirring for 10 minutes, the mixture is mixed with acrylamide (710 mg) and let react at 0° C. for 70 minutes and at room temperature for 3.5 hours. The mixture is mixed with acetic acid (0.7 ml), stirred for 20 minutes, diluted with ethyl acetate, filtered to remove solid, concentrated, and triturated in n-hexane to afford 2,6-dioxo-piperidine-3-carboxylic acid ethyl ester (1.18 g). m.p. 69°–74° C.

The product (555 mg) is dissolved in aqueous 1N-sodium hydroxide (6.6 ml). After stirring at 0° C. for 35 minutes, the mixture is mixed with 10% hydrochloric acid, concentrated in vacuum, dissolved in dichloromethane, filtered, and recrystallized from benzene to give 2,6-dioxopiperidine-3-carboxylic acid (99 mg). m.p. 116°–118° C.

Preparation 18

[3-oxomorpholine] —CH$_3$J/ClCOOEt→ —NaOH→ [N-methyl-3-oxomorpholine-COOH structure]

To a cold (0° C.) mixture stirred for 90 minutes of 3-oxomorpholine (1.01 g) and 60% sodium hydride is added methyl iodide (1.25 ml). After 60 minutes, the mixture is acidified with hydrochloric acid, concentrated, diluted with ethyl acetate, washed with water, dried, and concentrated to give 4-methylmorpholin-3-one (458 mg).

NMR (CDCl₃) δ: 3.00 (s, 3H), 4.13 (s, 2H).

A solution of said product (458 mg) in tetrahydrofuran (2 ml) is added to a cold (−60° C.) mixture of diisopropylamine (1.4 ml), n-butyllithium (6.3 ml), and tetrahydrofuran (20 ml). After 30 minutes' stirring, ethyl chloroformate (1.2 ml) is added to the mixture. After 30 minutes' stirring, the mixture is neutralized with hydrochloric acid, concentrated, diluted with ethyl acetate, washed with water, dried, and concentrated to give 4-methyl-3-oxo-morpholine-2-carboxylic acid ethyl ester (368 mg).

NMR (CDCl₃) δ:1.30 (t, 3H, 7 Hz), 3.00 (s, 3H), 4.23 (q, 2H, 7 Hz), 4.65 (s, 1H).

This product (308 mg) in aqueous 1N-sodium hydroxide (4 ml) is stirred for 60 minutes, acidified with hydrochloric acid, and extracted with dichloromethane-methanol. The extract is concentrated to give 4-methyl-3-oxomorpholine-2-carboxylic acid (172 mg). The product is used to acylate 7-amino-1-oxacephalosporin nucleus to give the objective amide without measuring physical constants.

Preparation 19

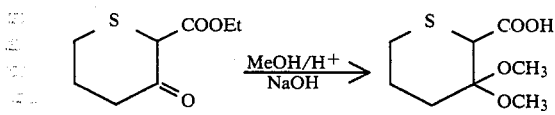

To a mixture of 3-oxothiane-2-carboxylic acid ethyl ester (2.0 g), methanol (8 ml), and methyl orthoformate (20 ml) is added p-toluenesulfonic acid monohydrate (120 mg). After refluxing overnight, the mixture is concentrated, diluted with ethyl acetate, washed with water, dried, and concentrated to give 3,3-dimethoxy-thiane-2-carboxylic acid ethyl ester (1.32 g).

NMR (CDCl₃) δ:1.33 (t, 3H, 7 Hz), 3.26 (s, 6H), 3.57 (s, 1H), 4.26 (q, 2H, 7 Hz).

IR (CHCl₃) ν:1730 cm⁻¹.

This product (1.04 g) is stirred in methanol (20 ml) with aqueous 1N-sodium hydroxide (18 ml) at 60° C. for 18 hours. The mixture is acidified with hydrochloric acid, and extracted with ethyl acetate. The extract is washed with water, dried, and concentrated. Crystallizing the residue from benzene gives 3,3-dimethoxy-thiane-2-carboxylic acid (675 mg).

IR (CHCl₃) ν:1715 cm⁻¹.

NMR (CDCl₃) δ:3.23 (s, 3H), 3.27 (s, 3H), 3.57 (s, 1H).

Preparation 20

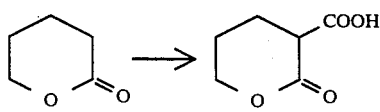

To a cold (−70° C.) solution of diisopropylamine (3.6 ml), 17% butyllithium in hexane (16 ml), and tetrahydrofuran (4 ml) is added dropwise a solution of valerolactone (1.86 ml) in tetrahydrofuran (10 ml). After 60 minutes' stirring, dry ice is added to the mixture. After 30 minutes, the reaction mixture is acidified with hydrochloric acid, concentrated, and extracted with ethyl acetate. The extract is washed with water and extracted with aqueous 5% sodium hydroxide. The extract is acidified with hydrochloric acid and reextracted with ethyl acetate. This is washed with water, dried, and concentrated to give the 3-carboxy-gamma-lactone (890 mg).

Preparation 21

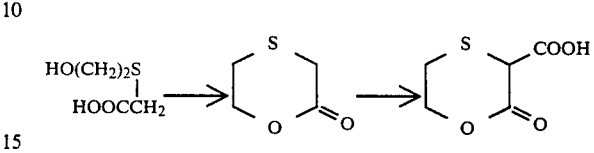

To a solution of 2-(2-hydroxyethylthio)acetic acid (3.38 g) in ethyl acetate (50 ml) are added 4-dimethylaminopyridine (0.1 ml) and N,N'-dicyclohexylcarbodiimide (6.15 g). After standing overnight at room temperature, this mixture is filtered to remove solid, concentrated, and distilled to give 2-oxo-1,4-oxathiane (0.90 g). bp (25 mmHg): 125° C.

This product is added dropwise to a cold (−70° C.) mixture of diisopropylamine (3.5 ml), 17% butyllithium in hexane (15.6 ml), and tetrahydrofuran (40 ml). After 60 minutes, this is mixed with dry ice, stirred for 1 hour, acidified with hydrochloric acid, concentrated, and extracted with ethyl acetate. The extract is extracted again with aqueous 5% sodium hydrogen carbonate. This aqueous extract is acidified with hydrochloric acid and reextracted with ethyl acetate. The extract is washed with water, dried, concentrated, and distilled to give 2-oxo-1,4-oxathiane-3-carboxylic acid (0.9 g).

NMR (CDCl₃)δ: 4.40 (s, 1H).

Preparation 22

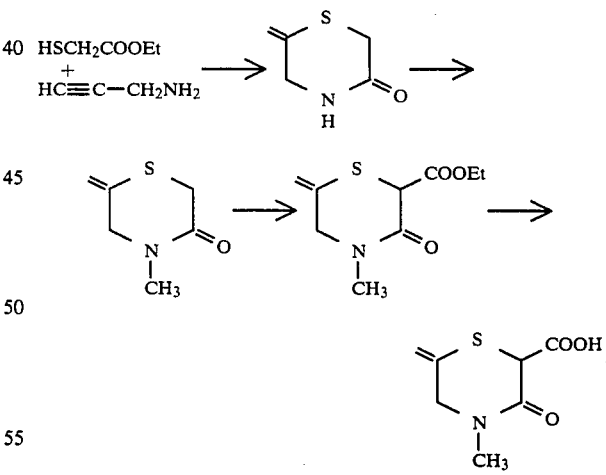

To a mixture of ethyl thioglycolate (11 ml), ethanol (60 ml), and propargylamine (6.9 ml) is added sodium borohydride (1.5 g). After 5 hours' refluxing, the mixture is neutralized with alcoholic hydrochloric acid, concentrated, diluted with dichloromethane, washed with water, dried, concentrated, and crystallized from ethyl acetate to give 3-oxo-6-methylene-2,3,5,6-tetrahydro-4H-1,4-thiazine (6.65 g). m.p. 80°–82° C.

IR (CHCl₃)ν: 3430, 1695 cm⁻¹.

NMR (CD₃COCD₃-CD₃OD)δ: 3.38 (s, 2H), 4.07 (bs, 2H), 4.90 (bs, 1H), 5.07 (bs, 1H).

This product (525 mg), tetrahydrofuran, (40 ml), and 50% sodium hydride (234 mg) are mixed at 0° C. and stirred at room temperature for 30 minutes. To this mixture is added methyl iodide (0.38 ml). After 2 hours' stirring, the mixture is acidified with acetic acid, concentrated, diluted with ethyl acetate, washed with water, dried, concentrated, and chromatographed to give 3-oxo-4-methyl-6-methylene-2,3,5,6-tetrahydro-1,4-thiazine (516 mg).

NMR (CDCl$_3$)δ: 3.03 (s, 3H), 3.38 (s, 2H), 4.03 (bs, 2H), 4.98 (bs, 1H), 5.08 (bs, 1H).

A solution of this product (516 mg) in tetrahydrofuran (5 ml) is added to a cold (below −60° C.) solution of lithium diisopropylamide in tetrahydrofuran. To this mixture is added ethyl chloroformate (0.69 ml). After 20 minutes' stirring, the mixture is acidified with acetic acid, concentrated, diluted with ethyl acetate, washed with water, dried, concentrated, and chromatographed to give the ethoxycarbonyl compound (756 mg).

NMR (CDCl$_3$) δ: 1.32 (t, 3H, 7 Hz), 3.08 (s, 3H), 3.85–4.55 (m, 2H+1H), 4.30 (q, 2H, 7 Hz), 5.12–5.25 (m, 2H).

This product is hydrolyzed with 1N-sodium hydroxide in ethanol to give free acid. This is condensed with 7β-amino-7α-methoxy-3-substituted methyl-1-dethia-1-oxa-3-cephem-4-carboxylic acid ester.

Preparation 23

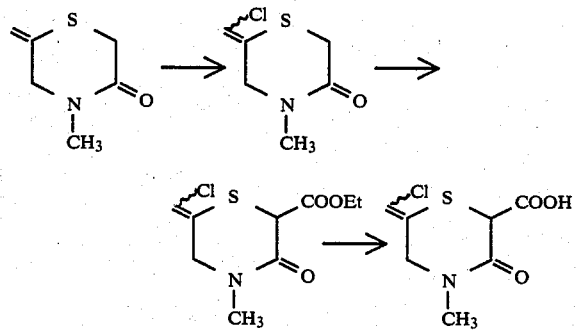

To a solution of 3-oxo-4-methyl-6-methylene-2,3,5,6-tetrahydro-1,4-thiazine (1.30 g) in dichloromethane (20 ml) cooling at −60° C. is added a 1.2M solution of chlorine in carbon tetrachloride (8.4 ml). After 20 minutes' stirring, the mixture is concentrated, diluted with dimethylformamide (4 ml), mixed with lithium chloride (1.30 g), stirred for 1.5 hours, concentrated, diluted with ethyl acetate, washed with water, dried, concentrated, and chromatographed to give chloromethylene compound (0.46 g).

NMR (CDCl$_3$)δ: 3.05 (s, 3H), 3.47 (s, 2H), 4.10 (m, 2H), 6.13 (m, 1H).

A solution of this product (0.50 g) in tetrahydrofuran (5 ml) is added to a cold (below −70° C.) solution of lithium diisopropylamide in tetrahydrofuran prepared from diisopropylamine (0.51 ml) and a 1.6M solution (2.3 ml) of n-butyllithium in hexane. After 20 minutes' stirring, ethyl chloroformate (0.4 ml) is added to the mixture. After 10 minutes' stirring, the reaction mixture is acidified with acetic acid, concentrated, diluted with ethyl acetate, washed with water, dried, concentrated, and chromatographed to give ethoxycarbonyl compound (0.11 g).

NMR (CDCl$_3$)δ: 1.32 (t, 3H, 7 Hz), 3.05 (s, 3H), 4.25 (q, 2H, 7 Hz), 3.83–4.50 (m, 2H), 4.43 (s, 1H), 6.12 (m, 1H).

The product is hydrolyzed with aqueous 1N-sodium hydroxide in ethanol at 0° C. to give objective carboxylic acid. This is condensed with 7β-amino-7α-methoxy-3-substituted methyl-1-dethia-1-oxa-3-cephem-4-carboxylic acid ester.

Preparation 24

ClCH(COOEt)$_2$
+
HCl.NH$_2$CH$_2$CH$_2$CH$_2$SH $\longrightarrow$

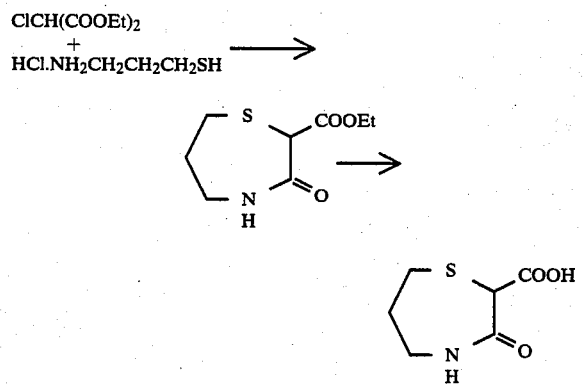

To a cold (0° C.) mixture of ethyl chloromalonate (1.62 ml), ethanol (30 ml), and thiopropanolamine hydrochloride (1.27 g) is added dropwise 1N solution of sodium ethoxide in ethanol (20 ml) with stirring. After refluxing for 5 hours, the mixture is concentrated, diluted with dichloromethane, filtered to remove solid, concentrated, chromatographed over silica gel, and crystallized from ethyl acetate to give 3-oxo-2H-tetrahydro-1,4-thiazepine-2-carboxylic acid ethyl ester (309 mg). m.p. 145°–146° C.

IR (CHCl$_3$)ν: 3420, 1740, 1680 cm$^{-1}$.

NMR (CDCl$_3$)δ: 1.30 (t, 3H, 7 Hz), 1.76–2.27 (m, 2H), 2.95 (t, 2H, 5 Hz), 3.2–3.47 (m, 2H), 4.28 (q, 2H, 7 Hz), 4.35 (s, 1H), 6.93 (brs, 1H).

This product is hydrolyzed with aqueous 1N-sodium hydroxide at 0° C. for 40 minutes to give the 3-oxo-2H-tetrahydro-1,4-thiazepine-2-carboxylic acid.

NMR (CDCl$_3$-CD$_3$OD)δ: 1.7–2.2 (m, 2H), 2.97 (t, 2H, 5 Hz), 4.33 (s, 1H).

Preparation 25

ClCH$_2$COOCH$_3$
+
HCl.NH$_2$CH$_2$CH$_2$CH$_2$SH $\longrightarrow$

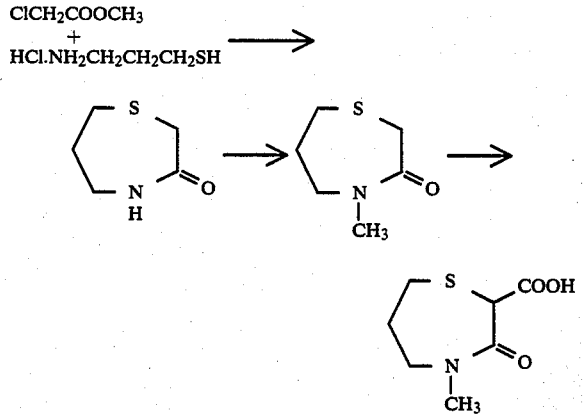

To a cold (0° C.) mixture of methyl chloroacetate (1.09 g), ethanol (60 ml), and thiopropanolamine hydrochloride (1.28 g) is added dropwise a 1N-solution of sodium ethoxide in ethanol (20 ml). After stirring at 55° C. for 4 hours, the mixture is mixed with sodium ethoxide solution (1 ml), stirred for 3 hours, let stand for 3 days at room temperature, concentrated, diluted with dichloromethane, filtered to remove solid, concentrated, and chromatographed over silica gel to give 3-oxo-2H-tetrahydro-1,4-thiazepine (1.06 g). m.p. 145°–146° C.

IR (CHCl₃)ν: 3420, 1680 cm⁻¹.

NMR (CDCl₃)δ: 1.8–2.2 (m, 2H), 2.8–3.0 (m, 2H), 3.2–3.45 (m, 2H), 3.28 (s, 2H), 6.6 (brs, 1H).

To a cold (0° C.) suspension of this product (655 mg) in tetrahydrofuran (30 ml) is added 50% sodium hydride (260 mg). After 20 minutes' stirring, methyl iodide (0.40 ml) is added to the mixture at 0° C. After 80 minutes' stirring, the reaction mixture is diluted with water and extracted twice with dichloromethane. The extract is dried, concentrated, and chromatographed over silica gel to give 4-methyl-3-oxo-2H-tetrahydro-1,4-thiazepine (697 mg).

m.p. 109°–110° C.

IR (CHCl₃)ν: 1650 cm⁻¹.

NMR (CDCl₃)δ: 1.8–2.2 (m, 2H), 2.8–3.0 (m, 2H), 3.00 (s, 3H), 3.38 (s, 2H), 3.4–3.55 (m, 2H).

A solution of this product (580 mg) in tetrahydrofuran (12 ml) is added dropwise to a cold (−70° C.) solution (15 ml) of lithium diisopropylamide (2.5 equivalents) in tetrahydrofuran. After 1 hour's stirring, a solution of ethyl chloroformate (1.2 ml) in tetrahydrofuran (3 ml) is added dropwise to the mixture. After 10 minutes' stirring, the reaction mixture is acidified with 10% hydrochloric acid (8 ml) and extracted with dichloromethane. The extract is washed with water, dried, concentrated, and chromatographed over silica gel to give 4-methyl-3-oxo-tetrahydro-2H-1,4-thiazepine-2-carboxylic acid ethyl ester (847 mg) as syrup.

IR (CHCl₃)ν: 1740, 1660 cm⁻¹.

NMR (CDCl₃)δ: 1.32 (t, 3H, 7 Hz), 1.8–2.2 (m, 2H), 2.83–3.02 (m, 2H), 3.02 (s, 3H), 3.38–3.63 (m, 2H), 4.28 (q, 2H, 7 Hz), 4.55 (s, 1H).

This product (787 mg) is hydrolyzed with 1N-sodium hydroxide at 0° C. for 1 hour to give 4-methyl-3-oxotetrahydro-2H-1,4-thiazepine-2-carboxylic acid (756 mg) as crystals.

IR (Nujol)ν: 1740, 1605 cm⁻¹.

NMR (CDCl₃-CD₃OD)δ: 1.7–2.2 (m, 2H), 2.8–3.1 (m, 2H), 3.03 (s, 3H), 3.3–3.7 (m, 2H), 4.53 (s, 1H).

Preparation 26

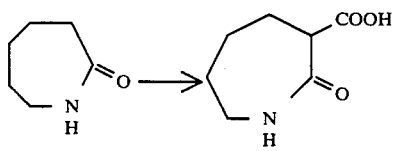

To a cold (−50° C.) mixture of a 0.10M solution (63 ml) of butyllithium in hexane and tetrahydrofuran (100 ml) is added 0.10M-diisopropylamine (14 ml). After 20 minutes' stirring at −5° to −7° C., the mixture is mixed with a 0.1M-solution of caprolactam (11.3 ml) in tetrahydrofuran (30 ml), stirred at −20° to −15° C. for 10 minutes, cooled to −70° C., mixed with 0.1M solution (63 ml) of butyllithium in hexane, stirred at −10° to −5° C. for 10 minutes, cooled to −70° C., mixed with dry ice, warmed to 0° C. during 2 hours period, and diluted with aqueous sodium hydrogen carbonate and ethyl acetate. The aqueous layer is taken, neutralized with hydrochloric acid, saturated with saline, and extracted with methyl ethyl ketone. The extract is washed with saturated saline, dried over magnesium sulfate, and concentrated to leave oil. This is crystallized from ethyl acetate to give the objective compound (810 mg).

m.p. 127°—128° C.

NMR (CD₃OD)δ: 1.4–2.1 (m, 6H), 3.29 (brs, 2H), 3.62 (t, 1H, 5 Hz).

Preparation 27

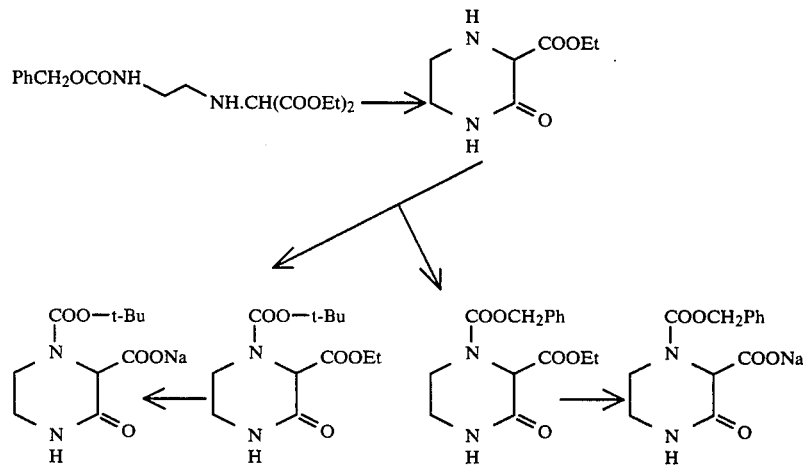

The starting diester (1.4 g) in ethanol (10 ml) is hydrogenolyzed with palladium charcoal. After calculated amount of hydrogen is consumed, the mixture is filtered to remove solid and concentrated to give 2-oxopiperazine-3-carboxylic acid ethyl ester (0.68 g).

To a suspension of this product (140 mg) in ethyl acetate (2 ml) is added 2-t-butoxycarbonylthio-4,6-dimethylpyrimidine (195 mg). After standing at room temperature overnight, the mixture is chromatographed to give 2-oxo-t-butoxycarbonylpiperazine-3-carboxylic acid ethyl ester (90 mg) as colorless crystals, m.p. 86°–87° C.

IR (CHCl₃)ν: 3400, 1741, 1692 cm⁻¹.

NMR (CDCl₃)δ: 1.30 (t, 3H, 8.0 Hz), 1.43 (s, 9H), 3.28–4.06 (m, 4H), 4.25 (q, 2H, 8.0 Hz), 4.98 (s, 1H), 7.53 (bs, 1H).

To a solution of this product (400 mg) in ethanol (4 ml) is added 1N-sodium hydroxide (2 ml) at 0° C. After stirring at room temperature for 50 minutes, separated crystals are collected by filtration and washed with a mixture of ethanol and ether to give 2-oxo-N-t-butoxycarbonylpiperazine-3-carboxylic acid sodium salt as plates.

Anal. (for $C_{10}H_{15}N_2O_5Na$): Calcd (%): C, 45.12; H, 5.68; N, 10.52. Found (%): C, 45.38: H, 5.75; N, 10.48.

To a cold (−20° C.) solution of above 2-oxopiperazine-3-carboxylic acid ethyl ester (0.34 g) in tetrahydrofuran are dropwise added benzyl chloroformate (340 mg) and triethylamine (202 mg). After standing for 30 minutes the reaction mixture is concentrated in vacuum, diluted with ethyl acetate, and chromatographed to give oily 2-oxo-4-benzyloxycarbonylpiperazine-3-carboxylic acid ethyl ester (320 mg) as oil.

IR $(CHCl_3)\nu$: 3390, 1740, 1689 cm$^{-1}$.

NMR $(CDCl_3)\delta$: 1.10-1.40 (m, 3H), 3.37-4.30 (m, 6H), 5.03 (s, 1H), 5.10 (s, 2H), 7.22 (s, 5H), 7.48 (bs, 1H).

To a solution of this product (425 mg) in ethanol (3 ml) is added 1N-sodium hydroxide (1.75 ml). After 90 minutes stirring, separating crystals are collected by filtration and washed with ethanol to give 2-oxo-4-benzyloxycarbonylpiperazine-3-carboxylic acid sodium salt as colorless needles. NMR $(D_2O)\delta$: 3.32-3.80 (m, 4H), 4.83 (s, 1H), 5.15 (s, 2H), 7.37 (s, 5H).

EXAMPLE 1 (Amidation)

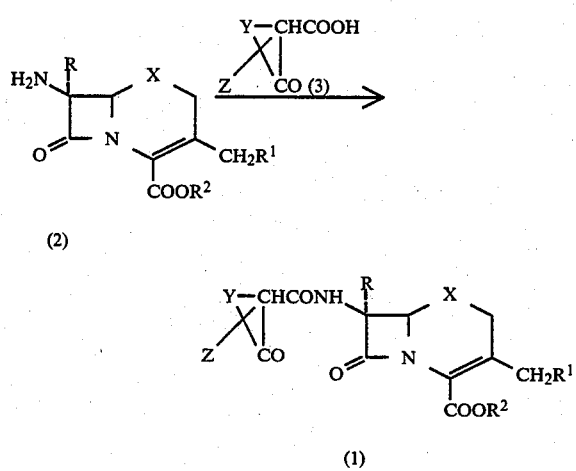

7-beta-Amino compound (2) (1 equivalent) is treated with Carboxylic acid corresponding to the 7-beta-side chain (3) or its reactive derivative to give Amide (1), for example, by a method as exemplified below:

(1) In a mixture of dichloromethane (10 volumes), 2-ethoxy-1-ethoxycarbonyl-1,2-dihydroquinoline (1.1 equivalents), N,N'-dicyclohexylcarbodiimide (1.1 equivalents), pyridine (1.5 equivalents), and Carboxylic acid (3) (1.1 equivalents), stirred for 1 to 6 hours at 0° C. to room temperature.

(2) In a mixture of ethyl acetate (10 volumes), di-2-pyridyl disulfide (1.1 equivalents), triphenylphosphine (1.1 equivalents), and Carboxylic acid (3) (1.1 equivalents), stirred for 2 to 6 hours at 10° to 50° C.

(3) In a mixture of dichloromethane (3 volumes), 1,3,5-tripyridiniumtriazine trichloride (4 equivalents), and Carboxylic acid (3) (1.1 equivalents), stirred for 1 to 5 hours at −10° to 10° C.

(4) In a mixture of carbon tetrachloride (30 volumes), 4-methylmorpholine (1.5 equivalents), trisdiethylaminophosphine (1.1 equivalents) and Carboxylic acid (3) (1.1 equivalents), kept for 1 to 5 hours at −20° to 10° C.

(5) In a mixture of chloroform (10 volumes) and dimethoxyethane (10 volumes), pyridine (1.5 moles), and a mixed anhydride of Carboxylic acid (3) and isobutoxyformic acid, stirred at a temperature between −5° to 10° C. over a 30 minutes and 6 hours time.

(6) In a mixture of ethyl acetate (10 volumes), 1,2-dichloroethane (10 volumes), 4-methylmorpholine (1.5 equivalents), and the symmetric anhydride of Carboxylic acid (3) (1.1 equivalents), refluxed for 10 minutes to 2 hours.

(7) In a mixture of dichloromethane (10 volumes), pyridine (1.5 equivalents), and mixed anhydride of Carboxylic acid (3) and methanesulfonic acid (1.1 equivalents), kept at 0° C. to room temperature over 1 to 3 hours.

(8) In a mixture of ethyl acetate (10 volumes), pyridine (1.5 equivalents) and a mixed anhydride of diethyl hydrogen phosphate and Carboxylic acid (3) (1.5 equivalents), stirred at 0° C. to 10° C. for 1 to 5 hours.

(9) In a mixture of ethyl acetate (7 volumes), dichloromethane (10 volumes), pyridine (1 equivalent), and mixed anhydride of Carboxylic acid (3) and dichlorophosphoric acid (1.1 equivalents), stirred for 1 to 3 hours at 0° C. to room temperature.

(10) In a mixture of lutidine (1.5 equivalents), dichloromethane (10 volumes), and the mixed anhydride (1.1 to 2 equivalents) of Carboxylic acid (3) and monochlorophosphoric acid dimethylamide, stirred for 1 to 4 hours at 0° to 30° C.

(11) In a mixture of dichloromethane (5 volumes), trifluoroacetic anhydride (1.5 equivalents), pyridine (3 equivalents), and Carboxylic acid (3) (1.5 equivalents), stirred for 1 to 5 hours at 0° C. to room temperature.

(12) In a mixture of dichloromethane (10 volumes), bromide of diethyl hydrogen phosphate (1.2 equivalents), 4-methylmorpholine (2.5 equivalents), and Carboxylic acid (3) (1.2 equivalents), stirred for 1 to 3 hours at 0° C. to room temperature.

(13) Amine (2) having carboxy at position 4 is dissolved in aqueous (10 volumes) sodium hydrogen carbonate (2.5 equivalents). Carboxylic acid (3) chloride (1.1 equivalents) is dropwise added thereto. The mixture is kept at −5° C. to room temperature for 30 minutes to 2 hours.

(14) Amine (2) having carboxy at position 4 is treated with trimethylsilyl chloride and triethylamine (1.2 equivalents each) to O-silylate, and then treated with pyridine (4 equivalents) and Carboxylic acid (3) chloride (1.1 equivalents) at −30° C. for between 30 minutes and 2 hours, and then the obtained silyl ester is hydrolyzed with acid.

(15) In a solution of picoline (4 equivalents) and Carboxylic acid (3) chloride (1.2 equivalents) in dichloromethane (20 volumes) at 0° C. to −30° C. over 30 minutes and 2 hours.

(16) In a mixture of dimethylformamide (2 volumes) and ethyl acetate (10 volumes), stirred with triethylamine (1.1 quivalents) and Carboxylic acid (3) chloride (1.1 equivalents) at 0° C. to −20° C. for between 30 minutes and 3 hours.

(17) In a mixture of dichloromethane (30 volumes), cyanuric chloride (1.1 equivalents), pyridine (4 equivalents), and Carboxylic acid (3) (1.1 equivalents), stirred for 30 minutes to 2 hours at −30° C. to 10° C.

(18) In a mixture of dichloromethane (3 volumes), phosphorus oxychloride (1.1 equivalents), pyridine (1.5 equivalents), and Carboxylic acid (3) (1.1 equivalents), stirred for 20 minutes to 2 hours at −10° C. to 10° C.

(19) Amine (2) is treated with trimethylsilyl chloride to obtain the corresponding N-trimethylsilyl compound, and this is treated with phosphorus oxychloride (1.5 equivalents), Carboxylic acid (3) (1.2 equivalents), and pyridine (4 equivalents) in dichloromethane (5 parts) for 30 minutes to 2 hours at 0° C. to room temperature.

(20) In a mixture of dichloromethane (8 volumes), thionyl chloride (1.5 equivalents), pyridine (2.5 equivalents), and Carboxylic acid (3) (1.1 equivalents), stirred for 1 to 5 hours at −30° to 0° C.

(21) In a mixture of chloroform (3 volumes), toluene (1 volume), picoline (2 equivalents), oxalyl chloride (1 equivalent), and Carboxylic acid (3) (1.1 equivalents), stirred for 10 minutes to 2 hours at −50° C. to 10° C.

(22) In a mixture of dichloromethane (20 volumes), pyridine (3 equivalents), and 1-oxabenzotriazolyl ester of Carboxylic acid (3) (3 equivalents), stirred for 5 to 30 hours at 10° to 50° C.

(23) In a mixture of dichloromethane (20 volumes), 1-hydroxybenzotriazole (2.1 equivalents), N,N'-dichlorohexylcarbodiimide (2.5 equivalents) and Carboxylic acid (3) (2 equivalents), stirred at room temperature for 1 to 15 hours.

(24) In a mixture of dioxane (10 volumes) and phthalimide of Carboxylic acid (3) (2 equivalents), stirred for 2 to 8 hours at 10° to 50° C.

(25) In a mixture of methyl isobutyl ketone (10 volumes) and succinimide of Carboxylic acid (3) (1.5 equivalents), stirred for 2 to 9 hours at 0° to 40° C.

(26) In a mixture of carbonyldiimidazole (1.1 equivalents), tetrahydrofuran (10 volumes), dimethylacetamide (5 volumes), and Carboxylic acid (3) (1.1 equivalents), stirred for 1 to 5 hours at 0° C. to room temperature.

(27) In a mixture of dimethylformamide (5 volumes), dimethylaniline (1.3 equivalents) and the Vilsmeyer reagent made from Carboxylic acid (3) and dimethylformamide (1.1 equivalents), stirred at room temperature for 1 to 5 hours.

(28) In a mixture of dichloromethane (10 volumes), dimethylformamide (5 volumes), N,N-dicyclohexylcarbodiimide (1.1 equivalents), picoline (1.2 equivalents), and Carboxylic acid (3) (1.1 equivalents), heated for 2 hours to 24 hours.

In the above, volume is expressed by ml per gram of the starting Amine (2) and equivalent shows molar equivalent per 1 molar equivalent of the starting Amine (2), The product is isolated, if required after diluting with a solvent, (dichloromethane, etc.), adjusting pH, washing with water, drying, and concentrating, then purifying by crystallization, adsorption, etc., if required after chromatography over silica gel. Physicochemical constants of Amides are identified by comparing with those of the product from other route.

EXAMPLE 2 (DEESTERIFICATION)

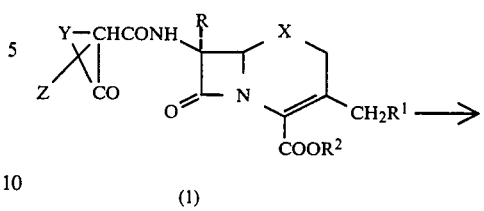

(1)

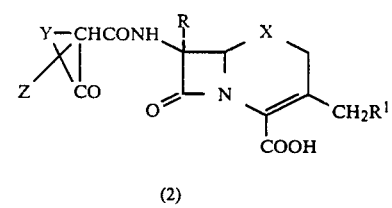

(2)

($R^2$ = $CHPh_2$ or $CH_2C_6H_4OCH_3$—P)

(1) A solution of the p-methoxybenzyl ester or diphenylmethyl ester (1) (1 part) in a mixture of dichloromethane (0.3 to 3 parts), trifluoroacetic acid (0.3 to 3 parts) and anisole (0.5 to 5 parts) is stirred at a temperature between −10° and 40° C. over 10 minutes to 3 hours period. The reaction mixture is concentrated in vacuum to remove the solvent and reagents. The residue is washed with benzene to give the corresponding free acid (2). Yield: 70 to 90%.

(2) To a solution of above starting material (1) (1 part) in a mixture of dichloromethane (5 to 9 parts) and anisole (2 to 8 parts) is added aluminum chloride. After stirring for 1 to 3 hours at −10° and 10° C., the mixture is washed with diluted hydrochloric acid and water, dried, and concentrated to give the corresponding free acid (2). Yield: 80 to 95%.

EXAMPLE 3 (SODIUM SALT, PREPARATION, USE)

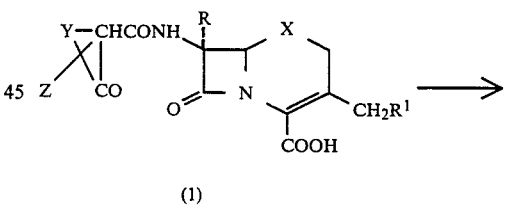

(1)

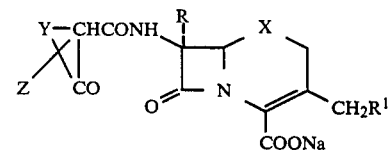

(2)

A solution of Carboxylic acid (1) (1 g) in aqueous 0.5% sodium hydrogen carbonate (5 ml) adjusted to pH 7 with hydrochloric acid is washed with ethyl acetate, desalted, and poured into 10 ml vials. This is lyophilized conventionally to give the corresponding sodium salt (2) as powder.

The sodium salt (1 g) produced under sterile condition is dissolved in sterile water (4 g) is injected twice a day intravenously to a patient suffering from Staphylococcus aureus infection for treating said disease. The sodium salt (2) is assayed for MIC by the standard method of Japan Society of Chemotherapy to give values less than 1 μg/ml against Streptococcus pyogenes C-203 and less than 0.1 μg/ml Escherichia coli JC-2.

EXAMPLE 4 (HETEROTHIO INTRODUCTION)

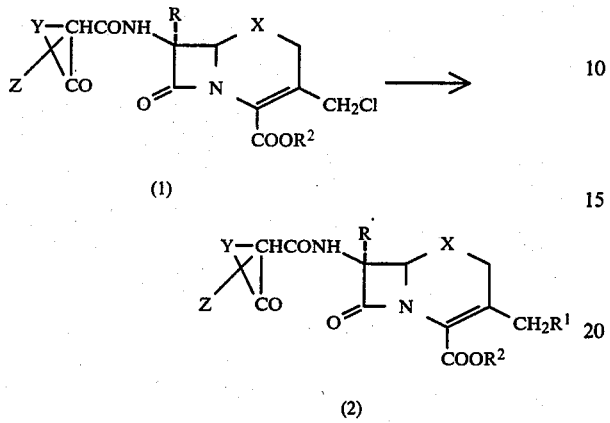

(1) A solution of 3-chloromethyl compound (1) (1 part), heterocyclic thiol sodium salt (1.2 equivalents), tetrabutylammonium bromide (trace amount) in dichloromethane (10 to 20 parts) and water (1 to 5 parts) is stirred for 30 minutes to 3 hours at room temperature. Organic layer is washed with water, dried, and concentrated to give the corresponding heterocyclic thio compound (2). Yield: 80 to 90%.

(2) A solution of 3-chloromethyl compound (1) (1 part) and heterocyclic thiol sodium salt (1.2 equivalents) in N,N-dimethylformamide (3 to 5 parts) is stirred for 30 minutes to 3 hours at 0° C. The solution is poured into water and extracted with ethyl acetate. The extract is washed with water, dried, and ceoncentrated to give the corresponding heterocyclic thio compound (2). Yield: 80 to 90%.

EXAMPLE 5 (PHARMACOLOGICALLY ACCEPTABLE ESTERS)

(1) To a solution of Carboxylic acid (1) potassium salt (1 millimole) in N,N-dimethylformamide (2 to 5 parts) is added iodomethyl pivalate (1 to 2 equivalents) under ice cooling. After 15 minutes to 2 hours' stirring, the mixture is diluted with ethyl acetate, washed with ice water and aqueous sodium hydrogen carbonate, dried, and concentrated in vacuum. The residue is recrystallized from ethyl acetate to give the pivaloyloxymethyl ester (2).

(2) The potassium salt of above section (1) is replaced by sodium salt to give the same products under same condition.

(3) Pivaloyloxymethyl ester (2) of above section (1) (250 mg), corn starch (150 mg), and magnesium stearate (5 mg) are mixed, granulated, and encapsulated in a conventional manner.

This capsule (1 to 3 capsules) is given orally to treat a patient suffering from infection caused by sensitive Escherichia coli JC-2.

(4) In place of iodomethyl pivalate of above (1), iodomethyl acetate or iodoethyl ethoxyformate is used under the same condition to give the corresponding acetoxymethyl ester (2) or ethoxycarbonyloxyethyl ester (2).

EXAMPLE 6 (METHOXYLATION)

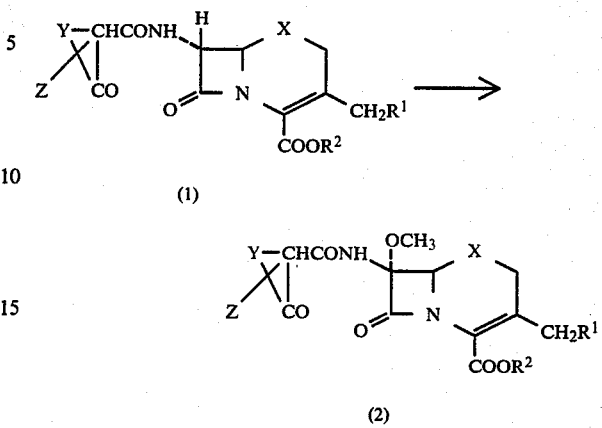

To a solution of 7α-amido-3-substituted methyl-1-dethia-1-oxa-3-cephem-4-carboxylic acid derivative (1) (1 part) in dichloromethane (10 parts) is added tert-butyl hypochlorite (1.1 equivalents). After standing for 3 hours at −20° C., a solution of lithium methoxide (1.2 equivalents) in methanol is added to the mixture and let react for 30 minutes. The reaction mixture is acidified with acetic acid and diluted with dichloromethane. This is washed with water, dried, and concentrated in vacuum to give the corresponding 7β-amido-7α-methoxy-3-substituted methyl-1-dethia-1-oxa-3-cephem-4-carboxylic acid derivative (2) in 40 to 85% yield.

EXAMPLE 7 (ALTERATION OF OTHER PART OF THE MOLECULE)

(1) Sulfoxide introduction

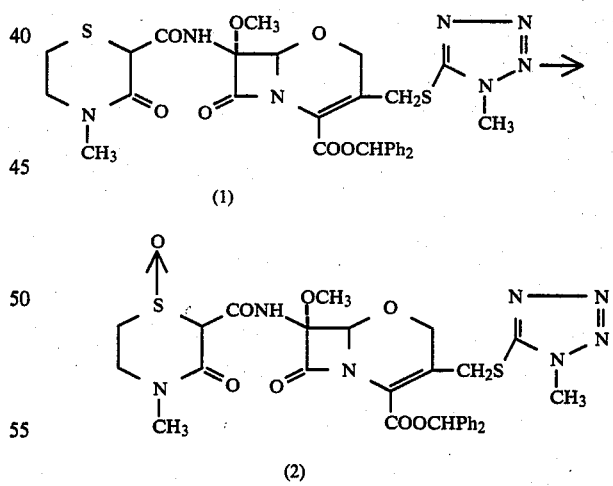

To a solution of 7β-(4-methyl-3-oxothiomorpholin-2-yl)carboxamido-7α-methoxy-3-(1-methyl-5-tetrazolyl)-thiomethyl-1-dethia-1-oxa-3-cephem-4-carboxylic acid diphenylmethyl ester (1) (283 mg) in dichloromethane (5 ml) is added m-chloroperbenzoic acid (113 mg). After 2 hours' stirring, the mixture is washed with aqueous 5% sodium hydrogen carbonate, dried, and concentrated to give the corresponding sulfoxide (165 mg).
Yield: 57%.

(2) Ether hydrolysis

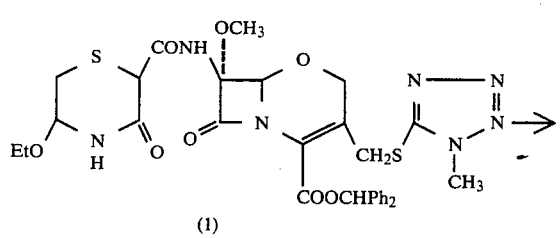

(1)

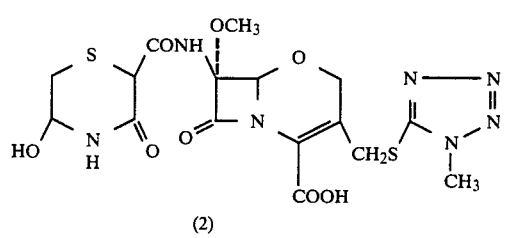

(2)

To a solution of 7β-(5-ethoxy-3-oxothiomorpholin-2-yl)carboxamido-7α-methoxy-3-(1-methyl-5-tetrazolyl)-thiomethyl-1-dethia-1-oxa-3-cephem-4-carboxylic acid diphenylmethyl ester (1) (137 mg) in dichloromethane (2.5 ml) are added trifluoroacetic acid (0.25 ml) and anisole (0.25 ml). After 25 minutes' stirring, the mixture is concentrated and chromatographed to give the corresponding 7β-(5-hydroxy-3-oxothiomorpholin-2-yl)carboxamido-7α-methoxy-3-(1-methyl-5-tetrazolyl)thiomethyl-1-dethia-1-oxa-3-cephem-4-carboxylic acid (2).

(3) Ketal hydrolysis

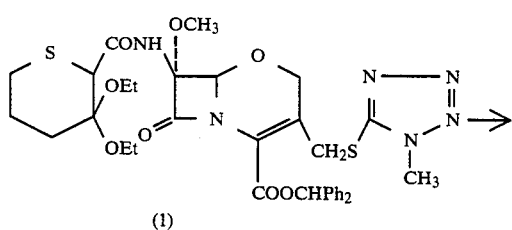

(1)

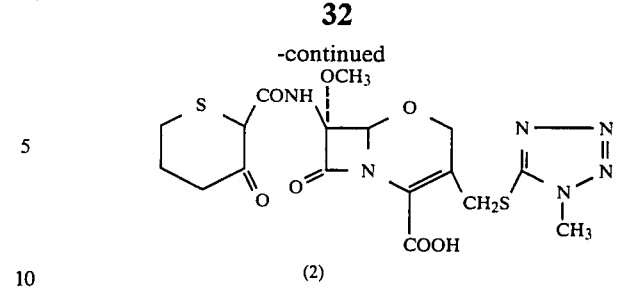

(2)

To a solution of 7β-(3,3-diethoxythiopyran-2-yl)carboxamido-7α-methoxy-3-(1-methyl-5-tetrazolyl)thiomethyl-1-dethia-1-oxa-3-cephem-4-carboxylic acid diphenylmethyl ester (247 mg) in acetone (4 ml) is added 1N-hydrochloric acid (0.4 ml). After standing at room temperature for 8 hours, the mixture is concentrated and extracted with ethyl acetate. The extract is washed with water, dried, and concentrated to give 7β-(3-oxothiopyran-2-yl)carboxamido-7α-methoxy-3-(1-methyl-5-tetrazolyl)thiomethyl-1-dethia-1-oxa-3-vcephem-4-carboxylic acid diphenylmethyl ester (201 mg).

(4) Ring closure at side chain

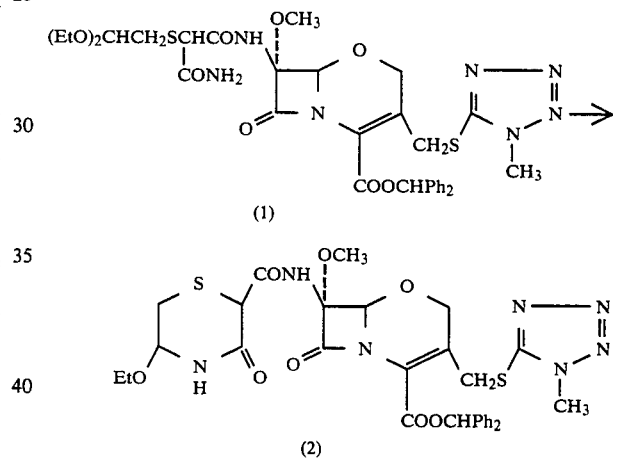

To a solution of 7β-(2-(2,2-diethoxyethyl)thio-2-carbamoyl-acetamido)-7α-methoxy-3-(1-methyl-5-tetrazolyl)thiomethyl-1-dethia-1-oxa-3-cephem-4-carboxylic acid diphenylmethyl ester (1) (200 mg) in ethyl acetate (8 ml) is added 20% perchloric acid (0.4 ml). After stirring at room temperature for 30 minutes, the mixture is neutralized with aqueous 5% sodium hydrogen carbonate. The organic layer is taken, washed with water, dried, concentrated, and chromatographed over silica gel to give 7β-(5-ethoxy-3-oxothiomorpholin-2-yl)carboxamido-7α-methoxy-3-(1-methyl-5-tetrazolyl)-thiomethyl-1-dethia-1-oxa-3-cephem-4-carboxylic acid diphenylmethyl ester (2) (130 mg). Yield: 70%.

Products of Examples 1 through 7 are listed in on Table 3 with their physical constants.

TABLE 3

A—NH—[structure with R, X, CH2R1, COOR2, lactam ring]

A: { Y—CHCO— / Z—CO }

| NO. | A | R | X | R¹ | R² | IR (cm⁻¹) | NMR (δ ppm) |
|---|---|---|---|---|---|---|---|
| 1 | CH₃N-[β-lactam]-CO— | CH₃O | O | STetCH₃ | CHPh₂ | CHCl₃: 3350,1785, 1750,1705. | CDCl₃: 2.77(s,3H),3.1~3.8(m,2H),3.57 (s,3H),3.72(s,3H),3.8~4.4(m, 3H),4.62(s,2H),5.03-5.08(2 × s, 1H),6.93(s,1H),7.1~7.7(m,10H). |
| 2 | CH₃N-[β-lactam]-CO— | CH₃O | O | STetCH₃ | H | KBr: 3300,1785, 1740,1700. | CDCl₃ + CD₃OD: 2.88(s,3H),3.3~4.3(m,2H),4.32(s, 2H),4.58(s,2H),5.05(s,1H). |
| 3 | HN-[lactam]-CO— | H | S | STetCH₃ | CHPh₂ | CHCl₃: 3440,1790, 1710. | CDCl₃: 2.1~2.6(m,2H),3.0~3.5(m,3H), 3.67(s,2H),3.73(s,3H),4.20,4.33 (ABq,J = 13Hz,2H),4.92(d,J = 5Hz, 1H),5.83(dd,J = 5;8Hz,1H),6.90 (s,1H),7.1~7.6(m,10H). |
| 4 | HN-[lactam]-CO— | H | S | STetCH₃ | H | CHCl₃: 3300,1780, 1700. | TLC: Rf(CH₃COOC₂H₅—CH₃COOH— H₂O(8:1:1)) = 0.17 |
| 5 | HN-[lactam]-CO— | CH₃O | O | STetCH₃ | CHPh₂ | CHCl₃: 3430,1790, 1710. | CDCl₃: 2.0~2.8(m,2H),3.0~3.5(m,3H), 3.57(s,3H),3.72(s,3H),4.23(s, 2H),4.60(s,2H),5.02,5.07(2 × s, 1H),6.83(s,1H),6.92(s,1H), 7.1~7.7(m,10H). |

TABLE 3-continued

| NO. | A | R | X | R¹ | R² | IR (cm⁻¹) | NMR (δ ppm) |
|---|---|---|---|---|---|---|---|
| 6 | CO—<br>（pyrrolidinone ring）<br>N—H | CH₃O | O | STetCH₃ | H | KBr:<br>3320,1785,<br>1705. | CDCl₃ + CD₃OD:<br>2.2–2.7(m,2H),3.2–3.7(m),3.95<br>(s,3H),4.33(s,2H),4.63(s,2H),<br>5.07;5.10(2 × s,1H). |
| 7 | CO—<br>（succinimide ring）<br>N—H | CH₃O | O | STetCH₃ | CHPh₂ | CHCl₃:<br>3390,1790,<br>1725. | CDCl₃:<br>2.4–3.3(m,2H),3.3–4.0(m,1H),<br>3.53(s,3H),3.70(s,3H),4.20(s,<br>2H),4.60(s,2H),5.03;5.07(2 × s,<br>1H),6.88(s,1H),7.0–7.7(m,10H),<br>9.38(brs,1H). |
| 8 | CO—<br>（succinimide ring）<br>N—H | CH₃O | O | STetCH₃ | H | KBr:<br>3280,1785,<br>1720. | CDCl₃:<br>2.6–3.4(m,2H),3.58(s,3H),<br>3.7(m),3.98(s,3H),4.33(s,2H),<br>4.63(s,2H),5.07,5.12(2 × s,1H). |
| 9 | CO—<br>（γ-butyrolactone ring） | CH₃O | O | STetCH₃ | CHPh₂ | CHCl₃:<br>3320,1790,<br>1760,1710. | CDCl₃:<br>2.20–3.13(m,2H),3.40–3.97(m,1H),<br>3.57(s,3H),3.78(s,3H),4.12–4.53<br>(m,2H),4.27(brs,2H),4.63(brs,2<br>H),5.03;5.08(2 × s,1H),6.90(s,1H),<br>7.13–7.75(m,10H). |
| 10 | CO—<br>（γ-butyrolactone ring） | CH₃O | O | STetCH₃ | H | Nujol:<br>3270,1780,<br>1700. | CDCl₃:<br>2.33–3.50(m,2H),3.40–3.77(m,1H),<br>3.58(s,3H),3.97(s,3H),4.1–4.5<br>(m,2H),4.33(brs,2H),4.63(brs,<br>2H),5.07;5.10(2 × s,1H). |

A: $\begin{pmatrix} Y-CHCO- \\ \diagdown \\ \diagup \\ Z-CO \end{pmatrix}$

Structural formula:

A—NH—CH(R)—[β-lactam ring with X, N, CH₂R¹, COOR²]

TABLE 3-continued

![Structure: A—NH-R on β-lactam with X, CH2R1, COOR2 substituents; A: Y—CHCO—/Z—CO bracket]

| NO. | A | R | X | R¹ | R² | IR (cm⁻¹) | NMR (δ ppm) |
|---|---|---|---|---|---|---|---|
| 11 | ![CO— with S-CH-C(=O)-N(CH3)-CH2 ring] | CH₃O | O | STetCH₃ | CHPh₂ | Nujol: 3250,1790, 1700,1665. | CDCl₃: 2.73(s,3H),3.53(s,3H),3.75(s,3H),4.25(brs,4H),4.57(brs,3H),4.97,5.00(2 × s,1H),6.82(s,1H), 7.07–7.67(m,10H). |
| 12 | ![CO— with S-CH-C(=O)-N(CH3)-CH2 ring] | CH₃O | O | STetCH₃ | H | Nujol: 3250,1785, 1700,1660. | CDCl₃—CD₃OD: 2.98(s,3H),3.57(s,3H),3.95(s,3H),4.32(brs,2H),4.60(brs,2H), 4.23–4.73(m,3H),5.03;5.07(2 × s, 1H). |
| 13 | ![CO— with S-CH-C(=O)-N(C2H5)-CH2 ring] | CH₃O | O | STetCH₃ | CHPh₂ | CHCl₃: 1790,1710, 1670. | CDCl₃: 1.10(t,J = 7Hz,3H),3.37(q,J = 7Hz, 2H),3.53(s,3H),3.70(s,3H),4.27 (s,4H),4.60(s,3H),5.00;5.02(2 × s, 1H),6.87(s,1H),7.2–7.7(m,10H), 8.42(s,1H). |
| 14 | ![CO— with S-CH-C(=O)-N(C2H5)-CH2 ring] | CH₃O | O | STetCH₃ | H | KBr: 3420,1787, 1707,1662. | CDCl₃: 1.18(t,J = 7Hz,3H),3.48(q,J = 7Hz, 2H),3.58(s,3H),3.98(s,3H),4.2–4.7(m,7H),5.07;5.10(2 × s,1H). |
| 15 | ![CO— with S-CH-C(=O)-N(n-C3H7)-CH2 ring] | CH₃O | O | STetCH₃ | CHPh₂ | CHCl₃: 3250,1790, 1710,1670. | CDCl₃: 0.85(t,J = 7Hz,3H),1.2–1.8(m,2H), 3.28(t,J = 7Hz,2H),3.55(s,3H), 3.67(s,3H),4.0–4.8(m,3H),4.23 (s,2H),4.60(s,2H),5.03(s,1H), 6.90(s,1H),7.0–7.7(m,10H),8.48 (s,1H). |

TABLE 3-continued structure: A-NH-[R on β-lactam ring]-X-N-CH₂R¹/COOR² with =C (CH₂R¹)(COOR²) substituent; A: Y-CHCO-/Z-CO cross structure

| NO. | A | R | X | R¹ | R² | IR (cm⁻¹) | NMR (δ ppm) |
|---|---|---|---|---|---|---|---|
| 16 | S-CH(CO-)-C(=O)-N(n-C₃H₇)- (thiazolidinone ring) | CH₃O | O | STetCH₃ | H | KBr: 3280,1785, 1705,1662. | CDCl₃ + CD₃OD: 0.92(t,J = 7.5Hz,3H),1.2–1.9(m, 2H),3.37(t,J = 7Hz,2H),3.57(s, 3H),4.2–4.8(m,3H),4.32(s,2H), 4.60(s,2H),5.07(s,1H). |
| 17 | S-CH(CO-)-C(=O)-N(CH₂CH₂O-tetrahydropyranyl)- | CH₃O | O | STetCH₃ | CHPh₂ | CHCl₃: 3250,1790 1705,1665. | CDCl₃: 1.2–2.0(m,6H),3.2–4.0(m,6H), 3.57(s,3H),3.77(s,3H),4.25(s, 2H),4.27–4.8(m,6H),5.00;5.03 (2 × s,1H),6.87(s,1H),7.2–7.7 (m,10H). |
| 18 | S-CH(CO-)-C(=O)-N(CH₂CH₂OH)- | CH₃O | O | STetCH₃ | CHPh₂ | CHCl₃: 1790,1710, 1670. | CDCl₃: 3.3–4.0(m,4H),3.53(s,3H),3.77 (s,3H),4.2–4.8(m,7H),5.05(s, 1H),6.88(s,1H),7.2–7.8(m,10H). |
| 19 | S-CH(CO-)-C(=O)-N(CH₂CH₂OH)- | CH₃O | O | STetCH₃ | H | KBr: 3440,1785, 1700,1665. | CDCl₃ + CD₃OD: 3.95(s,3H),4.2–4.8(m,7H),5.07 (s,1H). |

TABLE 3-continued $$A-NH-\underset{\underset{O}{\overset{R}{\bigsqcup}}}{\overset{X}{\bigsqcup}}-\underset{COOR^2}{\overset{CH_2R^1}{\bigsqcup}} \quad \left(A: \underset{Z}{\overset{Y-CHCO-}{\bigtimes}}_{CO}\right)$$

| NO. | A | R | X | R¹ | R² | IR (cm⁻¹) | NMR (δ ppm) |
|---|---|---|---|---|---|---|---|
| 20 | CO—<br>S⟨⟩N—CH₃<br>CH₃ O<br>CH₃ | CH₃O | O | STetCH₃ | CHPh₂ | CHCl₃:<br>3270,1790,<br>1715,1670. | CDCl₃:<br>1.4–1.7(m,3H),2.85(s,3H),3.57<br>(s,3H),3.75(s,3H),4.27(s,2H),<br>4.4–4.8(m,4H),5.07(s,1H),6.88<br>(s,1H),7.2–7.7(m,10H). |
| 21 | CO—<br>S⟨⟩N—CH₃<br>CH₃ O<br>CH₃ | CH₃O | O | STetCH₃ | POM | CHCl₃:<br>3250,1795,<br>1750,1710,<br>1670. | CDCl₃:<br>1.23(s,9H),1.57(d,J = 6Hz,3H),<br>2.90(s,3H),3.53(s,3H),3.88(s,<br>3H),4.27(s,2H),4.4–4.9(m,4H),<br>5.03(s,1H),5.85;5.98(ABq,J = 5Hz,<br>2H). |
| 22 | CO—<br>S⟨⟩N—CH₃<br>CH₃ O<br>CH₃ | CH₃O | O | STetCH₃ | H | KBr:<br>3430,1785,<br>1705,1663. | CDCl₃ + CD₃OD:<br>1.58;1.65(2 × d,J = 6Hz,3H),2.95<br>(s,3H),3.58(s,3H),4.32(s,2H),<br>4.4–4.8(m,4H),5.05;5.08(2 × s,<br>1H). |
| 23 | CO—<br>S⟨⟩N—CH₃<br>C₂H₅ O | CH₃O | O | STetCH₃ | CHPh₂ | CHCl₃:<br>3260,1790,<br>1710,1670. | CDCl₃:<br>0.93(t,J = 7Hz,3H),1.6–2.1(m,2H),<br>2.90(s,3H),3.58(s,3H),3.80(s,3H),<br>4.27(s,2H),4.4–4.8(m,4H),5.05(s,<br>1H),6.92(s,1H),7.2–7.8(m,10H). |
| 24 | CO—<br>S⟨⟩N—CH₃<br>C₂H₅ O | CH₃O | O | STetCH₃ | H | KBr:<br>3430,1786,<br>1708,1660. | CDCl₃ + CD₃OD:<br>0.97(t,J = 7Hz,3H),1.6–2.1(m,2H),<br>2.93(s,3H),3.55(s,3H),3.95(s,<br>3H),4.30(s,2H),4.4–4.8(m,4H),<br>5.05(s,1H). |

TABLE 3-continued $$A-NH\underset{O}{\overset{R}{\underset{|}{\bigsqcup}}}\underset{N}{\overset{X}{\bigsqcup}}\underset{COOR^2}{\overset{CH_2R^1}{=}}$$

$$\left(A: \underset{Z}{\overset{Y-CHCO-}{\underset{CO}{\bigtimes}}}\right)$$

| NO. | A | R | X | R¹ | R² | IR (cm⁻¹) | NMR (δ ppm) |
|---|---|---|---|---|---|---|---|
| 25 | ![structure: NCCH₂-N(CH₃)-CH₂-CH(S-)-CO- with CH₃ on S-bearing carbon] | CH₃O | O | STetCH₃ | CHPh₂ | CHCl₃: 1790,1705. | CDCl₃: 2.95(s,3H),2.90–3.15(m,2H),3.53 (s,3H),3.78(s,3H),4.25(s,2H), 4.62(s,2H),4.7–5.1(m,3H),6.88 (s,1H),7.25–7.65(m). |
| 26 | ![structure: NCCH₂-N(CH₃)-CH₂-CH(S-)-CO-] | CH₃O | O | STetCH₃ | H | KBr: 2255,1787, 1705,1680. | CD₃OD: 3.00(s,3H),3.57(s,3H),4.00(s, 3H),4.27(s,2H),4.63(s,2H),4.55– 5.15(m). |
| 27 | ![structure: Ph-CH(N(CH₃))-CH(S-)-CO-] | CH₃O | O | STetCH₃ | CHPh₂ | CHCl₃: 3280,1790, 1715,1670. | CDCl₃: 2.65:2.70(2×s,3H),3.60(s,2H), 3.72(s,3H),4.23(s,2H),4.60(s, 2H),4.82(s,1H),5.06(s,1H),5.40; 5.60(2×s,1H),6.90(s,1H),7.1– 7.7(m,15H),8.26;8.45(2×s,1H). |
| 28 | ![structure: Ph-CH(N(CH₃))-CH(S-)-CO-] | CH₃O | O | STetCH₃ | H | KBr: 3430,1787, 1710,1670. | CDCl₃ + CD₃OD: 2.73(s,3H),3.93(s,3H),4.33(s, 2H),4.62(s,2H),4.80(s,1H),5.08 (s,1H),5.50;5.73(2×s,1H),7.35 (s,5H). |
| 29 | ![structure: CH₃-CH(N(CH₂CH₂CH₃))-CH(S-)(CH₃)-CO-] | CH₃O | O | STetCH₃ | CHPh₂ | CHCl₃: 3260,1795. 1715,1670. | CDCl₃: 0.88(t,J = 7Hz,3H),1.2–1.9(m,5H), 2.7–3.5(m,2H),3.57(s,3H),3.75 (s,3H),4.23(s,2H),4.4–4.9(m, 4H),5.00;5.03(2×s,1H),6.87;6.89 (2×s,1H),7.1–7.7(m,10H). |

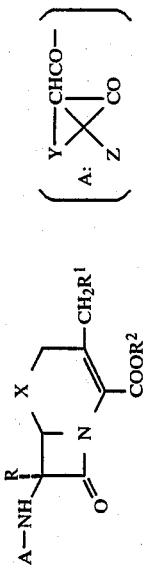

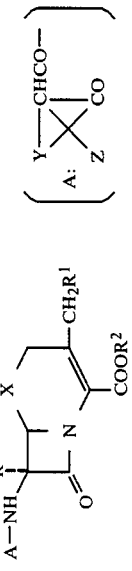

TABLE 3-continued

| NO. | A | R | X | R[1] | R[2] | IR (cm$^{-1}$) | NMR (δ ppm) |
|---|---|---|---|---|---|---|---|
| 41 | | CH$_3$O | O | STetCH$_3$ | CHPh$_2$ | CHCl$_3$: 3400,3300, 1787,1700, 1649,1510. | CDCl$_3$: 1.4–2.4(m,4H),3.0–3.5(m,3H), 3.52(s,3H),3.76(s,3H),4.13(s, 2H),4.60(s,2H),5.03(s,1H),6.89 (s,1H),6.89(brs,1H),7.1–7.7(m, 10H). |
| 42 | | CH$_3$O | O | STetCH$_3$ | H | KBr: 3300,1780, 1692,1637, 1520. | CD$_3$COCD$_3$: 1.5–2.4(m,4H),3.2–3.6(m,3H), 3.47(s,3H),3.97(s,3H),4.32(s, 2H),5.07(s,1H),6.53(brs,1H). |
| 43 | ![](piperidone-CO N-CH$_3$) | CH$_3$O | O | STetCH$_3$ | CHPh$_2$ | CHCl$_3$: 3270,1788, 1712,1697, 1625,1258. | CDCl$_3$: 1.78–2.5(m,4H),2.93;2.97(2 × s, 3H),3.23–3.35(m,3H),3.54;3.57 (2 × s,3H),3.81(s,3H),4.27(s,2H), 4.60(s,2H),4.99;5.02(2 × s,1H), 6.89(s,1H),7.28–7.65(m,10H), 8.88(b,1H). |
| 44 | ![](piperidone-CO N-CH$_3$) | CH$_3$O | O | STetCH$_3$ | H | Nujol: 3220,1781, 1693,1620. | CD$_3$SOCD$_3$: 1.63–2.06(m,4H),2.83(s,3H),3.20– 3.35(m,3H),3.41(s,3H),3.94(s, 3H),4.23(s,2H),4.53(s,2H),5.04; 5.07(2 × s,1H),8.94;9.06(2 × s, 1H). |
| 45 | | H | S | STetCH$_3$ | CHPh$_2$ | — | CDCl$_3$: 3.27(brs,4H),3.67(brs,2H),3.78 (s,3H),4.28(brs,2H),4.93(d,J = 4.5Hz,1H),5.13(s,3H),5.70(dd, J = 4.5,8Hz,1H),6.88(s,1H),7.3 (m,15H),8.05(d,J = 8Hz,1H). |

TABLE 3-continued

Structure:
A—NH—[core with R, X, CH₂R¹, COOR², N, O ring]

A: { Y—CHCO— / X / Z—CO }

| NO. | A | R | X | R¹ | R² | IR (cm⁻¹) | NMR (δ ppm) |
|---|---|---|---|---|---|---|---|
| 46 | [H-N-CO / N-H ring with C=O, CO—] | H | S | STetCH₃ | H | KBr 3230, 2650, 1770, 1700. | CD₃SOCD₃ + D₂O: 3.3–3.8(m,6H),3.93(s,3H),4.18 (s,2H),5.07(d,J = 4.5Hz,1H),5.10 (s,1H),5.67(d,J = 4.5Hz,1H). |
| 47 | [COOCH₂Ph-N / N-H ring with CO—, C=O] | CH₃O | O | STetCH₃ | CHPh₂ | CHCl₃: 3400, 1792, 1713, 1679. | CDCl₃: 1.42(s,9H),3.30–3.70(m,4H),3.50; 3.55(2 × s,3H),3.77(s,3H),4.22 (brs,2H),4.60(brs,2H),5.00(s, 1H),6.83(s,1H),7.23–7.60(m,10H), 8.0(brs,1H). |
| 48 | [COOCH₂Ph-N / N-H ring with CO—, C=O] | CH₃O | O | STetCH₃ | CHPh₂ | — | CDCl₃: 3.25–3.80(m,4H),3.43,3.47(2 × s, 3H),3.75(s,3H),4.22(brs,2H), 4.53(brs,2H),4.97(s,1H),5.12(s, 2H),6.85(s,1H),7.31–7.72(m,15H). |
| 49 | [H-N-CO / N-H ring with C=O, O] | H | S | STetCH₃ | CHPh₂ | — | CD₃SDCD: 3.75(brs,2H),3.85(brs,2H),3.87 (s,3H),4.28(brs,2H),4.53(brs, 1H),5.17(d,J = 5Hz,1H),5.77(dd, J = 5,10Hz,1H),6.90(s,1H),7.25; 7.65(m,10H),8.18(brs,1H). |

TABLE 3-continued

A-NH-[structure with CH₂R¹, COOR², N, O, R]

A: (Y-CHCO- / Z-CO / X)

| NO. | A | R | X | R¹ | R² | IR (cm⁻¹) | NMR (δ ppm) |
|---|---|---|---|---|---|---|---|
| 50 | [piperazinedione-CO structure with HN, NH] | H | S | STetCH₃ | H | KBr: 3440,3250, 1770,1710, 1688,1676, 1540. | CD₃SOCD₃: 3.70(brs,2H),3.4–4.1(m,2H),3.97 (s,3H),4.33(brs,2H),4.53(brs, 1H),5.10(d,J = 5Hz,1H),5.63(dd, J = 5;8Hz,1H),8.22(brs,1H),8.42 (brs,1H),9.27(d,J = 8Hz,1H). |
| 51 | [morpholinone-CO structure with O, NCH₃] | CH₃O | O | STet—CH₃ | CHPh₂ | CHCl₃: 3300,1790, 1720,1650. | CDCl₃: 2.95(s,3H),3.32–4.12(m,4H),3.55 (s,3H),3.75(s,3H),4.23(brs,2H), 4.62(brs,2H),4.73(s,1H),5.02; 5.03(2 × s,1H),6.87(s,1H),7.10– 7.73(m,10H). |
| 52 | [morpholinone-CO structure with O, NCH₃] | CH₃O | O | STet—CH₃ | H | Nujol: 3250,1785, 1710,1630. | CDCl₃ + CD₃OD: 3.07(s,3H),3.33–3.67(m,2H),3.58 (s,3H),3.97(s,3H),Ca.3.97(m, 2H),4.33(s,2H),4.65(s,2H),4.80 (s,1H),5.07,5.10(2 × s,1H). |
| 53 | [thiazinone-CO structure with S, NH] | CH₃O | O | [N–N thiadiazole-S-] | CHPh₂ | CHCl₃: 3380,1780, 1720,1705, 1655. | CDCl₃: 2.4–3.8(m,4H),3.53;3.57(2 × s,3H), 4.28(brs,2H),4.40(s,1H),4.60(brs, 2H),5.03(s,1H),6.90(s,1H),7.0– 7.6(m,10H),8.37(s,1H). |
| 54 | [thiazinone-CO structure with S, NH] | CH₃O | O | [N–N thiadiazole-S-] | H | Nujol: 1785,1700, 1660. | CDCl₃ + CD₃OD: 2.5–3.8(m,4H),3.53;3.57(2 × s, 3H),4.17(s,1H),4.40(brs,2H), 4.60(brs,1H),5.03(s,1H). |

TABLE 3-continued

| NO. | A | R | X | R¹ | R² | IR (cm⁻¹) | NMR (δ ppm) |
|---|---|---|---|---|---|---|---|
| 55 | (S-CO-, NH ring structure) | CH₃O | O | (thiadiazole-S-C(=CH₂)CH₃) | CHPh₂ | CHCl₃: 1785,1705, 1660. | CDCl₃: 2.5–3.9(m,4H),2.63(s,3H),3.52; 3.55(2 × s,3H),4.27(s,2H),4.37 (s,1H),4.58(s,2H),5.03(s,1H), 6.90(s,1H),7.0–7.7(m,10H),8.30 (br,1H). |
| 56 | (S-CO-, NH ring structure) | CH₃O | O | (thiadiazole-S-C(=CH₂)CH₃) | H | Nujol: 3300,1785, 1700,1660. | CDCl₃ + CD₃OD: 2.4–3.9(m,4H),2.77(s,3H),3.53; 3.57(2 × s,3H),4.33(brs,3H),4.60 (s,2H),5.03(s,1H). |
| 57 | (S-CO-, NH ring structure) | CH₃O | O | (thiadiazole-S-CH₂-t-BuOCONH) | CHPh₂ | CHCl₃: 3450,3400, 1785,1710, 1660. | CDCl₃: 1.48(s,9H),2.4–3.9(m,4H),3.52; 3.55(2 × s,3H),4.27–4.58(m,7H), 5.02(s,1H),5.62(br,1H),6.85(s, 1H),7.1–7.6(m,10H),8.23(br,1H). |
| 58 | (S-CO-, NH ring structure) | CH₃O | O | (thiadiazole-S-CH₂-CF₃COOHNH₂) | H | Nujol: 1780,1690, 1650. | CD₃SOCD₃: 2.5–3.7(m,4H),3.43;3.46(2 × s,3H), 4.30(brs,3H),4.57(brs,4H),5.07 (s,1H). |

TABLE 3

$$A-NH \begin{array}{c} R \\ | \\ \end{array} \begin{array}{c} X \\ | \\ N \end{array} \begin{array}{c} CH_2R^1 \\ | \\ COOR^2 \end{array} \quad \left( A: \begin{array}{c} Y-CHCO- \\ | \\ Z \end{array} \begin{array}{c} \\ CO \end{array} \right)$$

| NO. | A | R | X | R¹ | R² | IR (cm⁻¹) | NMR (δppm) |
|---|---|---|---|---|---|---|---|
| 59 | [thiazine-CO-] | CH₃O | O | [N=thiazole-CH₂CN] | CHPh₂ | CHCl₃: 1790,1720, 1710,1660. | CDCl₃: 2.4–3.9(m,4H),3.52;3.55(2 × s, 3H),4.08(s,2H),4.28(brs,3H), 4.60(brs,2H),5.03(s,1H),6.88 (s,1H),7.0–7.7(m,10H),8.33(br, 1H). |
| 60 | [thiazine-CO-] | CH₃O | O | [N=thiazole-CH₂CN] | H | Nujol: 1780,1690, 1650. | CDCl₃ + CD₃OD: 2.4–3.8(m,6H),3.53;3.57(2 × s, 3H),4.17(s,1H),4.33(brs,2H), 4.60(s,2H),5.05(s,1H). |
| 61 | [thiazine-CO-] | CH₃O | O | [N=thiazole-CO-CO-OC₂H₅] | CHPh₂ | CHCl₃: 3390,1780, 1710,1655. | CDCl₃: 1.43(t,J = 7Hz,3H),2.4–3.8(m, 4H),3.57;3.60(2 × s,3H),4.2– 4.8(m,7H),5.07(s,1H),6.93(s, 1H),7.1–7.6(m,10H),8.23(br, 1H). |
| 62 | [thiazine-CO-] | CH₃O | O | [N=thiazole-CO-CO-OC₂H₅] | H | KBr: 3340,1785, 1740,1710, 1645. | CD₃OD: 2.4–3.8(m,4H),3.55;3.57(2 × s, 3H),4.17–4.8(m,7H),5.03(s,1H). |
| 63 | [thiazine-CO-] | H | S | STet—CH₃ | CHPh₂ | CHCl₃: 3360,1785, 1685. | CDCl₃: 2.67–3.97(m,4H),3.80(s,2H),3.87 (s,3H),4.10;4.13(2 × s,1H),4.27 (brs,2H),5.20(d,J = 5Hz,1H), 5.80(dd,J = 5;9Hz,1H),6.90(s, 1H),7.17–7.73(m,10H). |

TABLE 3-continued $$A-NH \underset{O}{\overset{R}{\underset{\parallel}{\bigcap}}} \underset{N}{\overset{X}{\bigcap}} \underset{COOR^2}{\overset{CH_2R^1}{\bigcap}} \quad \left( A: \underset{Z}{\overset{Y-CHCO-}{\underset{CO}{\bigcap}}} \right)$$

| NO. | A | R | X | R[1] | R[2] | IR (cm$^{-1}$) | NMR (δppm) |
|---|---|---|---|---|---|---|---|
| 64 | ![S/N-H ring with CO-] | H | S | STet—CH$_3$ | H | Nujol: 3350,1775, 1680. | d$_6$-DMSO: 2.61-3.60(m,4H),3.70(s,2H),3.97 (s,3H),4.13(s,1H),4.32(s,2H), 5.10(d,J = 5Hz,1H),5.70(dd,J = 5; 8Hz,1H). |
| 65 | ![S/N-H ring with CO-] | H | O | STet—CH$_3$ | CHPh$_2$ | CHCl$_3$: 3400,1800, 1700,1660. | CDCl$_3$: 2.50-3.97(m,4H),3.80(s,3H),4.23 (brs,3H),4.60(brs,2H),5.03(d, J = 4Hz,1H),5.60(dd,J = 4;9Hz,1H), 6.85(s,1H),7.00-7.70(m,10H). |
| 66 | ![S/N-H ring with CO-] | H | O | STet—CH$_3$ | H | Nujol: 3300,1780, 1650,1610. | CD$_3$OD: 2.50-3.83(m,4H),4.00(s,3H),4.40 (brs,2H),4.66(brs,2H),5.10(d, J = 5Hz,1H),5.50(d,J = 5Hz,1H). |
| 67 | ![S/N-H ring with CO-] | CH$_3$O | O | STet—CH$_3$ | CHPh$_2$ | CHCl$_3$: 3360,1790, 1705,1655. | CDCl$_3$: 2.37-3.97(m,4H),3.55,3.57(2 × s, 3H),3.62(s,3H),4.28(brs,3H), 4.63(s,2H),5.05(s,1H),6.90(s, 1H),7.00-7.73(m,10H). |
| 68 | ![S/N-H ring with CO-] | CH$_3$O | O | STet—CH$_3$ | POM | CHCl$_3$: 3400,1795, 1755,1710, 1665. | CDCl$_3$: 1.25(s,9H),2.48-3.83(m,4H),3.55 (s,3H),3.93(s,3H),4.30(brs,3H), 4.65(s,2H),5.05(s,1H),5.88;5.98 (ABq,J = 5Hz,2H). |

TABLE 3-continued $$A-NH \begin{array}{c} R \\ | \\ \end{array} \begin{array}{c} X \\ | \\ N \end{array} \begin{array}{c} CH_2R^1 \\ | \\ COOR^2 \end{array} \quad \left( A: \begin{array}{c} Y-CHCO- \\ | \\ Z \end{array} \right)$$

| NO. | A | R | X | R$^1$ | R$^2$ | IR (cm$^{-1}$) | NMR (δppm) |
|---|---|---|---|---|---|---|---|
| 69 | S⌒CO— ⌡N-H O | CH$_3$O | O | STet—CH$_3$ | H | Nujol: 3250,1780, 1690,1620. | d$_6$-DMSO: 2.70-4.07(m,4H),3.77(s,3H),3.95 (s,3H),4.15(s,1H),4.25(brs,2H), 4.40(s,2H),5.10(s,1H). |
| 70 | S⌒CO— ⌡N-H O | CH$_3$O | O | STet—CH$_2$—CH$_3$ | CHPh$_2$ | CHCl$_3$: 3396,3220, 1790,1712, 1660. | CDCl$_3$: 1.45(t,J = 7Hz,3H),2.5-4.0(m,4H), 3.57(s,3H),4.17(q,J = 7Hz,2H), 4.25(s,1H),4.27(s,2H),4.63(s, 2H),5.05(s,1H),6.80(brs,1H), 6.90(s,1H),7.2-7.6(m,10H),8.18 (brs,1H). |
| 71 | S⌒CO— ⌡N-H O | CH$_3$O | O | STet—CH$_2$—CH$_3$ | H | Nujol: 3485,3300, 2590,1780, 1695,1645, 1514. | CD$_3$COCD$_3$ + CD$_3$OD: 1.47(t,J = 8Hz,3H),2.5-4.0(m,4H), 3.48;3.52(2 × s,3H),4.33(q,J = 8Hz, 2H),4.33(s,2H),4.63(s,2H),5.08 (s,1H). |
| 72 | S⌒CO— ⌡N-H O | CH$_3$O | O | STet—CH(CH$_3$)CH$_3$ | CHPh$_2$ | CHCl$_3$: 3390,1780, 1700,1660. | CDCl$_3$: 1.53(d,J = 7Hz,6H),2.4-3.7(m,5H), 3.57;3.60(2 × s,3H),4.30(brs,3H), 4.67(brs,2H),5.07(s,1H),6.90(s, 1H),7.1-7.7(m,10H),8.23(brs,1H). |
| 73 | S⌒CO— ⌡N-H O | CH$_3$O | O | STet—CH(CH$_3$)CH$_3$ | H | KBr: 3200,1785, 1700,1645. | CD$_3$COCD$_3$: 1.57(d,J = 7Hz,6H),2.4-3.8(m,5H), 3.50;3.53(2 × s,3H),4.38(s,3H), 4.67(s,2H),5.08(s,1H). |

TABLE 3-continued

A-NH-[structure with R, X, CH₂R¹, COOR², N, O] (A: Y—CHCO / Z—CO / X)

| NO. | A | R | X | R¹ | R² | IR (cm⁻¹) | NMR (δppm) |
|---|---|---|---|---|---|---|---|
| 74 | [S-CH-CO / NH-CO ring structure] | CH₃O | O | STet—CH₂ CH₂=CH | CHPh₂ | CHCl₃: 3390,1790, 1710,1690, 1660. | CDCl₃: 2.5–3.8(m,4H),3.52,3.55(2 × s, 3H),4.25(brs,3H),4.60(brs,2H), 4.73(d,J = 6Hz,2H),5.02(s,1H), 5.20–5.37(m,2H),5.55–6.07(m,1H), 6.87(s,1H),7.1–7.6(m,10H),8.17 (brs,1H). |
| 75 | [S-CH-CO / NH-CO ring structure] | CH₃O | O | STet—CH₂ CH₂=CH | H | Nujol: 1780,1690, 1640. | CDCl₃ + CD₃OD: 2.4–3.9(m,4H),3.53,3.57(2 × s,3H), 4.33(s,2H),4.60(s,2H),4.90(d, J = 6Hz,2H),5.07(s,1H),5.27–5.47 (m,2H),5.6–6.4(m,1H). |
| 76 | [S-CH-CO / NH-CO ring structure] | CH₃O | O | STet—CF₂ H | CHPh₂ | CHCl₃: 3390,1785, 1705,1660. | CDCl₃: 2.2–3.8(m,4H),3.50,3.53(2 × s,3H), 4.25(brs,3H),4.58(s,2H),5.00(s, 1H),6.88(s,1H),7.0–7.7(m,10H), 7.35(t,J = 57Hz,1H). |
| 77 | [S-CH-CO / NH-CO ring structure] | CH₃O | O | STet—CF₂ H | H | KBr 1780,1695, 1645. | CDCl₃ + CD₃OD: 2.4–3.9(m,4H),3.52,3.57(2 × s,3H), 4.17(s,1H),4.40(s,2H),4.60(s, 2H),5.03(s,1H),7.53(t,J = 56Hz,1H). |
| 78 | [S-CH-CO / NH-CO ring structure] | CH₃O | O | STet—CH₂ (CH₃)₂NCH₂ | CHPh₂ | CHCl₃: 3380,1785, 1700,1655. | CDCl₃: 2.17(s,6H),2.4–3.7(m,4H),2.67 (t,J = 7Hz,2H),3.52,3.53(2 × s, 3H),4.08–4.30(m,5H),4.58(brs, 2H),5.02(s,1H),6.88(s,1H),7.2– 7.6(m,10H),8.23(brs,1H). |

TABLE 3-continued $$A-NH\underset{O}{\overset{R}{\underset{|}{\bigsqcup}}}\underset{N}{\overset{X}{\bigsqcup}}\underset{COOR^2}{\overset{CH_2R^1}{\bigsqcup}} \quad \left\{ A: \underset{Z}{\overset{Y-CHCO}{\underset{|}{\times}}}\underset{CO}{\overset{}{\bigsqcup}} \right\}$$

| NO. | A | R | X | R¹ | R² | IR (cm⁻¹) | NMR (δppm) |
|---|---|---|---|---|---|---|---|
| 79 | S—CO— / NH—C(=O) | CH₃O | O | STet—CH₂—(CH₃)₂NCH₂·CF₃COOH | H | Nujol: 3200,1775, 1680,1660. | CDCl₃ + CD₃OD: 2.5–3.8(m,4H),3.00(s,6H),3.57 (s,3H),3.77(brs,2H),4.13–4.37 (m,3H),4.50–4.80(m,4H),5.07 (s,1H). |
| 80 | S—CO— / NH—C(=O) | CH₃O | O | STet—CH₂—HO—CH₂ | CHPh₂ | CHCl₃: 3380,1790, 1710,1660. | CDCl₃ + CD₃OD: 2.5–3.7(m,4H),3.70–4.03(m,2H), 4.03–4.40(m,5H),4.53(s,2H), 5.03(s,1H),6.87(s,1H),7.1–7.7 (m,10H). |
| 81 | S—CO— / NH—C(=O) | CH₃O | O | STet—CH₂—HOCH₂ | H | KBr: 3320,1780, 1693,1645. | CDCl₃ + CD₃OD: 3.53;3.55(2 × s,3H),3.90–4.43(m, 7H),4.53(s,2H),5.03(s,1H). |
| 82 | S—CO— / NH—C(=O) | CH₃O | O | STet—CH₂—CN | CHPh₂ | CHCl₃ 1790,1710, 1660. | CDCl₃ + CD₃OD: 2.5–4.0(m,4H),3.68;3.87(2 × s, 3H),4.27(brs,2H),5.05(s,1H), 5.25(s,2H),6.83(s,1H),7.3–7.7 (m,10H). |
| 83 | S—CO— / NH—C(=O) | CH₃O | O | STet—CH₂—CN | H | KBr 3430,3340, 1780,1690, 1640. | CDCl₃ + CD₃OD + CD₃SOCD₃ 2.5–3.8(m,4H),3.50(brs,3H), 4.30(s,2H),4.60(s,2H),5.05(s, 1H),5.62(s,2H). |

TABLE 3-continued $$A-NH\underset{\underset{O}{\overset{R}{\bigvee}}}{\overset{X}{\bigvee}}\underset{COOR^2}{\overset{CH_2R^1}{\bigvee}} \quad \left( A: \underset{Z}{\overset{Y-CHCO}{\underset{CO}{\bigvee}}} \right)$$

| NO. | A | R | X | R¹ | R² | IR (cm⁻¹) | NMR (δppm) |
|---|---|---|---|---|---|---|---|
| 84 | S-CH₂-CH₂-CH(CO-)-N(H)-C(=O) | CH₃O | O | STet—CH₂—Ph₂CHOCO | CHPh₂ | CHCl₃: 3380,1790, 1755,1710, 1660. | CDCl₃: 2.23–3.77(m,4H),3.52;3.53(2 × s, 3H),4.15(brs,2H),4.23(s,1H), 4.50(brs,2H),5.00(brs,3H),6.87 (s,2H),6.93–7.68(m,20H). |
| 85 | S-CH₂-CH₂-CH(CO-)-N(H)-C(=O) | CH₃O | O | STet—CH₂—HOOC | H | Nujol: 3250,1780, 1690,1635. | CDCl₃ + CD₃OD: 2.40–3.83(m,4H),3.60(s,3H),4.35 (s,2H),4.53(s,2H),5.10(s,1H), 5.13(s,2H). |
| 86 | CH₃O-C(=CH)-C(=O)-N(H)- | CH₃O | O | STet—CH₂—CH₃OCO | CHPh₂ | CHCl₃: 3325,1790, 1765,1715, 1665. | CDCl₃: 2.16–3.93(m,4H),3.47;3.50(2 × s, 3H),3.65;3.67(2 × s,3H),4.20(brs, 3H),4.50(brs,2H),4.88(brs,2H), 4.97(s,1H),6.80(s,1H),6.90–7.62 (m,10H). |
| 87 | S-CH₂-CH₂-CH(CO-)-N(H)-C(=O) | CH₃O | O | STet—CH₂—CH₃OCO | H | Nujol: 3300,1780, 1760,1690, 1660,1640. | CDCl₃ + CD₃OD: 2.48–3.98(m,4H),3.55;3.58(2 × s, 3H),3.82(s,3H),4.32(brs,2H), 4.58(brs,2H),5.08(s,1H),5.18 (brs,2H). |
| 88 | S-CH₂-CH₂-CH(CO-)-N(H)-C(=O) | CH₃O | O | STet—CH₂—H₂N—CO | CHPh₂ | CHCl₃: 1785,1700, 1660. | CDCl₃ + CD₃OD: 2.5–3.8(m,7H),4.1–4.7(m,5H), 4.95(s,2H),5.07(s,1H),6.90(s, 1H),7.2–7.7(m,10H). |

TABLE 3-continued $$A-NH\underset{\underset{O}{\overset{R}{\bigg|}}}{\overset{R}{\bigg|}}\underset{N}{\overset{X}{\bigcap}}\underset{COOR^2}{\overset{CH_2R^1}{\bigg|}} \quad \left(A: \underset{Z}{\overset{Y-CHCO-}{\bigg|}}\right)$$

| NO. | A | R | X | R¹ | R² | IR (cm⁻¹) | NMR (δppm) |
|---|---|---|---|---|---|---|---|
| 89 | ![S-CO-NH ring structure] | CH₃O | O | STet—CH₂—H₂NCO | H | KBr: 3330,1782, 1690,1645. | CDCl₃ + CD₃OD: 2.5–3.8(m,7H),4.53(s,2H),5.07 (s,3H). |
| 90 | ![S-CO-NH ring structure] | CH₃O | O | STet—CHF—H₂N—CO | CHPh₂ | CHCl₃: 3470,3380, 1785,1720, 1655. | CDCl₃ + CD₃OD: 2.35–3.88(m,4H),3.55(s,3H), 4.27(brs,2H),4.50(brs,2H),5.03 (s,1H),6.62(d,J = 48Hz,1H),7.08– 7.62(m,10H). |
| 91 | ![S-CO-NH ring structure] | CH₃O | O | STet—CHF—H₂NCO | H | Nujol: 3270,1780, 1710,1640. | CDCl₃ + CD₃OD: 2.35–3.92(m,4H),3.53;3.57(2 × s, 3H),4.39(brs,2H),4.60(brs,2H), 5.07(s,1H),6.83(d,J = 47Hz,1H). |
| 92 | ![S-CO-NH ring structure] | CH₃O | O | STet—CH₂—PMBONHCO | CHPh₂ | CHCl₃: 3380,3260, 1790,1710, 1660,1605. | CDCl₃: 2.4–3.7(m,4H),3.53;3.57(2 × s, 3H),3.74(s,3H),4.00–4.30(m,3H), 4.39(brs,2H),4.76(brs,4H),4.99; 5.01(2 × s,1H),6.89(s,1H),6.80– 7.73(m,14H). |
| 93 | ![S-CO-NH ring structure] | CH₃O | O | STet—CH₂—HONHCO | H | Nujol: 3210,1780, 1685,1640. | CD₃OD: 2.5–3.7(m,4H),3.54;3.57(2 × s, 3H),4.27(s,2H),4.57(s,2H),5.03 (s,2H),5.07(s,1H). |

TABLE 3-continued

A-NH-R (structure with CH₂R¹, COOR², X, N, O ring)

A: [Y—CHCO / X / Z—CO]

| NO. | A | R | X | R¹ | R² | IR (cm⁻¹) | NMR (δppm) |
|---|---|---|---|---|---|---|---|
| 94 | S-CO-/NH ring with O | CH₃O | O | STet—CH₂—CH₃ONHCO | CHPh₂ | CHCl₃: 3380,3230, 1790,1710, 1660. | CDCl₃: 2.3–3.9(m,4H),3.57;3.59(2 × s, 3H),3.72(s,3H),4.13–4.40(m, 3H),4.53(brs,2H),4.98(brs,2H), 5.07(s,1H),6.89(s,1H),7.20–7.70(m,10H). |
| 95 | S-CO-/NH ring with O | CH₃O | O | STet—CH₂—CH₃ONHCO | H | Nujol: 3225,1785, 1695,1640. | CD₃COCD₃: 2.5–3.9(m,4H),3.50;3.53(2 × s, 3H),3.76;3.78(2 × s,3H),4.14(brs, 2H),4.33(brs,2H),4.61(brs,2H), 5.10(s,1H). |
| 96 | S-CO-/NH ring with O | CH₃O | O | STet—L—(cyclic NH-C=O) | CHPh₂ | CHCl₃: 1790,1725, 1705,1660. | CDCl₃ + CD₃OD: 2.4–3.8(m,8H),3.57;3.60(2 × s, 3H),4.23(brs,2H),4.57(brs,2H), 5.07(s,1H),4.9–5.3(m,1H),6.87 (s,1H),7.2–7.6(m,10H). |
| 97 | S-CO-/NH ring with O | CH₃O | O | STet—L—(cyclic NH-C=O) | H | KBr 3400,1780, 1708,1645. | CDCl₃ + CD₃OD: 2.5–3.8(m,8H),3.52;3.55(2 × s, 3H),4.18(s,1H),4.27(brs,2H), 4.55(brs,2H),5.05(s,3H),5.0–5.5(m,1H). |
| 98 | S-CO-/NH ring with O | CH₃O | O | STet—DL—(cyclic NH-C=O) | CHPh₂ | CHCl₃: 1790,1720, 1660. | CDCl₃ + CD₃OD: 2.35–3.80(m,8H),3.55;3.58(2 × s, 3H),4.23(brs,2H),4.55(brs,2H), 5.07(s,1H),4.9–5.3(m,1H),6.88 (s,1H),7.2–7.7(m,10H). |

TABLE 3-continued $$\text{A NH} \underset{O}{\overset{R}{\underset{N}{\bigvee}}} \overset{X}{\underset{COOR^2}{\bigvee}} \overset{CH_2R^1}{\underset{COOR^2}{\bigvee}} \left( A: \underset{Z}{\overset{Y-CHCO}{\bigvee}} \underset{CO}{\bigvee} \right)$$

| NO. | A | R | X | R¹ | R² | IR (cm⁻¹) | NMR (δppm) |
|---|---|---|---|---|---|---|---|
| 99 | S-CO-, NH ring with CO- | CH₃O | O | STet-CH₂ (DL) piperidinone | H | KBr: 3440,3320, 1785,1710, 1645. | CDCl₃ + CD₃OD: 2.5–3.8(m,8H),3.52,3.57(2 × s, 3H),4.18(s,1H),4.33(brs,2H), 4.55(brs,2H),5.07(s,1H),5.1–5.5(m,1H). |
| 100 | S-CO-, NH ring with CO- | CH₃O | O | STet-CH₂ (L) piperidinone | CHPh₂ | CHCl₃: 1790,1690. | CDCl₃ + CD₃OD: 1.8–4.0(m,10H),3.57,3.60(2 × s, 3H),4.23(brs,2H),4.57(brs,2H), 5.08(s,1H),4.8–5.1(m,1H),6.88 (s,1H),7.2–7.6(m,10H). |
| 101 | S-CO-, NH ring with CO- | CH₃O | O | STet-CH₂ (L) piperidinone | H | KBr: 3440,3330, 1785,1670. | CDCl₃ + CD₃OD: 1.8–3.9(m,10H),3.52,3.55(2 × s, 3H),4.28(brs,2H),4.57(s,2H), 5.07(s,1H),4.9–5.3(m,1H). |
| 102 | S-CO-, NH ring with CO- | CH₃O | O | STet-CH₂ NCCH₂ | CHPh₂ | CHCl₃: 2260,1790, 1710,1660, 1400. | CDCl₃: 2.4–4.0(m,4H),2.88(t,J = 6Hz,2H), 3.52,3.53(2 × s,3H),4.23(brs,3H), 4.33(t,J = 6Hz,2H),4.55(brs,2H), 5.00(s,1H),6.70(brs,1H),6.82(s, 1H),7.2–7.6(m,10H),8.13(brs,1H). |
| 103 | S-CO-, NH ring with CO- | CH₃O | O | STet-CH₂ NCCH₂ | H | KBr: 3430,3320, 2250,1780, 1693,1640. | CDCl₃ + CD₃OD: 2.4–4.0(m,4H),3.17(t,J = 6Hz,2H), 3.57,3.58(2 × s,3H),4.33(brs,1H), 4.63(t,J = 6Hz,2H),5.08(s,1H). |

TABLE 3-continued

![structure: A-NH-R on β-lactam with X, CH2R1, COOR2; A: (Y-CHCO / Z-CO) X]

| NO. | A | R | X | R¹ | R² | IR (cm⁻¹) | NMR (δppm) |
|---|---|---|---|---|---|---|---|
| 104 | S-CO- / NH-C(=O) ring | CH₃O | O | STet—CH₂ H₂NCOCH₂ | CHPh₂ | CHCl₃: 3400,1785, 1700,1685, 1660. | CDCl₃ + CD₃OD: 2.62–3.81(m,6H),3.57;3.60(2 × s, 3H),4.25(brs,3H),4.30–4.53(m, 2H),4.58(brs,2H),5.08(s,1H), 6.90(s,1H),7.13–7.56(m,10H). |
| 105 | S-CO- / NH-C(=O) ring | CH₃O | O | STet—CH₂ H₂NCOCH₂ | H | Nujol: 3300,1780, 1660. | CDCl₃ + CD₃OD: 2.50–3.90(m,6H),3.57(s,3H), 4.28(brs,3H),4.40–4.45(m,2H), 4.52(brs,2H), 5.05(s,1H). |
| 106 | S-CO- / NH-C(=O) ring | CH₃O | O | STet—CH₂ CH₂ H₂NSO₂ | CHPh₂ | Nujol: 1780,1690, 1650. | CDCl₃ + CD₃OD: 2.4–4.0(m,6H),3.55;3.58(2 × s, 3H),4.23(brs,2H),4.53(brs,2H), 4.62(t,J = 7Hz,2H),5.05(s,1H), 6.83(s,1H),7.2–7.6(m,10H). |
| 107 | S-CO- / NH-C(=O) ring | CH₃O | O | STet—CH₂ CH₂ H₂NSO₂ | H | KBr: 3460,3320, 1780,1690, 1643. | CDCl₃ + CD₃OD: 2.4–4.0(m,4H),3.53;3.57(2 × s, 3H),3.70(t,J = 7Hz,2H),4.17(s, 1H),4.30(brs,2H),4.53(brs,2H), 4.77(t,J = 7Hz,2H),5.07(s,1H). |
| 108 | S-CO- / NH-C(=O) ring | CH₃O | O | 2-pyridyl-S— | CHPh₂ | CHCl₃: 1780,1720, 1660. | CDCl₃: 2.4–3.8(m,4H),3.53;3.57(2 × s, 3H),4.13;4.40(ABq,J = 14Hz,2H), 4.40(s,1H),4.53(brs,2H),5.00 (s,1H),6.92(s,1H),7.2–8.3(m, 14H). |

TABLE 3-continued
| NO. | A | R | X | R¹ | R² | IR (cm⁻¹) | NMR (δppm) |
|---|---|---|---|---|---|---|---|
| 109 |  | CH₃O | O | 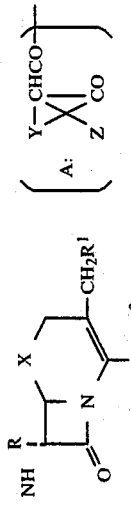·CF₃COOH | H | KBr: 3400,1780, 1685,1650. | CD₃OD: 2.5–3.8(m,4H),3.53(s,3H),4.20 (s,1H),4.20,4.40(ABq,J = 14Hz, 2H),4.57(s,2H),6.8–8.4(m,4H). |
| 110 | 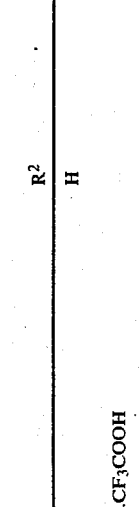 | CH₃O | O |  | CHPh₂ | CHCl₃ 3250,1780, 1705,1650. | ND |
| 111 | 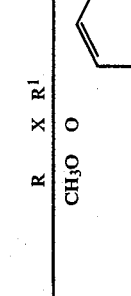 | CH₃O | O |  | H | Nujol: 3250,1780, 1680,1640. | ND |
| 112 | 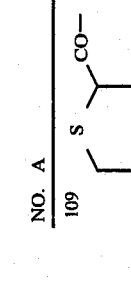 | CH₃O | O |  | CHPh₂ | CHCl₃: 3300,1790, 1710,1660, 1600. | CDCl₃: 2.22–3.97(m,4H),3.53(s,3H),4.25 (brs,3H),4.60(brs,2H),5.02(s, 1H),6.92(s,1H),7.03;7.95(ABq, J = 9Hz,2H),6.78-7.72(m,10H). |
| 113 |  | CH₃O | O | —S <br> (triazolopyridazine) | H | Nujol: 3300,1780, 1700,1650. | CDCl₃ + CD₃OD: 2.43–4.17(m,4H),3.53;3.56(2 × s, 3H),4.35(brs,2H),4.48(s,1H), 4.65(brs,2H),5.07(s,1H),7.42; 8.25(ABq,J = 9Hz,2H). |

TABLE 3-continued

| NO. | A | R | X | R¹ | R² | IR (cm⁻¹) | NMR (δppm) |
|---|---|---|---|---|---|---|---|
| 114 | ![structure with S, CH₃, N-H, CO] | CH₃O | O | ![aminotriazolopyridazine-S-] | CHPh₂ | CHCl₃: 1790,1730, 1700,1660. 1620. | CDCl₃ + CD₃OD: 2.5–3.8(m,4H),3.55;3.58(2 × s, 3H),4.15;4.35(ABq,J = 8Hz,2H), 4.63(brs,2H),5.07(s,1H),6.23 (s,1H),6.93(s,1H),7.2–7.6(m, 10H). |
| 115 | ![structure with S, CH₃, N-H, CO] | CH₃O | O | ![aminotriazolopyridazine-S-] | H | KBr: 3400,3320, 1780,1695, 1630,1570. | CD₃OD: 2.5–3.8(m,4H),3.53;3.55(2 × s, 3H),4.1–4.6(m,3H),4.65(s,2H), 5.05(s,1H),6.35(s,1H). |
| 116 | ![structure with S, CH₃, N-H, CO] | CH₃O | O | STet—CH₃ | CHPh₂ | CHCl₃: 3370,1785, 1705,1645. | CDCl₃: 1.20–1.35(m,3H),2.32–3.02(m,2H), 3.57;3.60(2 × s,3H),3.85(s,3H), 4.20(s,1H),4.30(s,2H),4.63(s, 2H),5.07(s,1H),6.63;6.70(2 × s, 1H),6.93(s,1H),7.2–7.6(m,10H), 8.1–8.3(m,1H). |
| 117 | ![structure with S, CH₃, N-H, CO] | CH₃O | O | STet—CH₃ | POM | CHCl₃: 3370,2950, 1790,1750, 1700,1650. | CDCl₃: 1.23(s,9H),1.20–1.40(m,3H),2.33– 3.03(m,2H),3.55;3.58(2 × s,3H), 3.88(brs,1H),3.97(s,3H),4.33(s, 2H),4.67(s,2H),5.10(s,1H),5.94; 6.03(ABq,J = 6Hz,2H),6.6–6.8(m, 1H),8.07–8.30(m,1H). |

TABLE 3

$$\text{A-NH}\underset{\underset{O}{\parallel}}{\overset{R}{\underset{|}{C}}}\text{-}\overset{X}{\underset{N}{C}}\text{-}\underset{COOR^2}{\overset{CH_2R^1}{C=}}$$

$$\left(A: \underset{Z}{\overset{Y}{\diagdown}}\underset{CO^-}{\overset{CHCO-}{\diagup}}\right)$$

| NO. | A | R | X | R¹ | R² | IR (cm⁻¹) | NMR (δppm) |
|---|---|---|---|---|---|---|---|
| 118 | ![structure: S-CH(CH3)-CH2 with N-H, CO- and C=O] | CH₃O | O | STet—CH₂<br>\|<br>CH₃ | H | CHCl₃:<br>3440,3300,<br>1787,1703,<br>1642. | CD₃OD:<br>1.20–1.37(m,3H),2.3–3.2(m,2H),<br>3.52;3.55(2 × s,3H),3.98(s,3H),<br>3.8–4.2(m,2H),4.25(s,2H),4.60<br>(s,2H),5.07(s,1H). |
| 119 | ![same structure] | CH₃O | O | STet—CH₂<br>\|<br>HOCH₂ | CHPh₂ | CHCl₃:<br>1785,1705,<br>1650. | CDCl₃ + CD₃OD:<br>1.16–1.36(m,3H),2.3–3.3(m,2H),<br>3.5–4.2(m,1H),3.56;3.59(2 × s,<br>3H),3.92(t,J = 5Hz,2H),4.25(brs,<br>2H),4.28(t,J = 5Hz,2H),4.55(d,<br>J = 3Hz,2H),5.05(s,1H),6.90(s,<br>1H),7.25–7.65(m,10H). |
| 120 | ![same structure] | CH₃O | O | STet—CH₂<br>\|<br>HOCH₂ | H | KBr:<br>3440,3310,<br>1780,1697,<br>1640,1515. | CD₃OD:<br>1.24;1.31(2 × d,J = 6Hz,3H),2.3–<br>3.3(m,2H),3.53;3.55(2 × s,3H),<br>3.6–4.2(m,1H),3.92(t,J = 6Hz,<br>2H),4.09(s,1H),4.27(s,2H),4.42<br>(t,J = 6Hz,2H),4.58(s,2H),5.05<br>(s,1H). |
| 121 | ![same structure] | CH₃O | O | STet—CH₂<br>\|<br>NCCH₂ | CHPh₂ | CHCl₃:<br>1790,1720,<br>1660. | CDCl₃ + CD₃OD:<br>1.20–1.35(m,3H),2.3–3.3(m,2H),<br>3.5–4.0(m,1H),2.97(t,J = 7Hz,2H),<br>3.56;3.60(2 × s,3H),4.26(brs,2H),<br>4.43(t,J = 7Hz,2H),4.60(brs,2H),<br>5.07(s,1H),6.88(s,1H),7.25–7.65<br>(m,10H). |
| 122 | ![structure with H₃C] | CH₃O | O | STet—CH₂<br>\|<br>NCCH₂ | H | KBr:<br>3480,3300,<br>2250,1780,<br>1695,1640,<br>1512. | CD₃OD:<br>1.25;1.32(2 × d,J = 6Hz,3H),2.3–<br>3.2(m,2H),3.15(t,J = 7Hz,2H),<br>3.53;3.55(2 × s,3H),3.6–4.05(m,<br>1H),4.10(s,1H),4.28(s,2H),<br>4.60(s,2H),4.62(t,J = 7Hz,2H),<br>5.05(s,1H). |

TABLE 3-continued

| NO. | A | R | X | R$^1$ | R$^2$ | IR (cm$^{-1}$) | NMR (δppm) |
|---|---|---|---|---|---|---|---|
| 123 | (structure: Cl-CH=... S, CO—, N-H ring) | CH$_3$O | O | STet—CH$_3$ | CHPh$_2$ | CHCl$_3$: 3380,1790, 1730. | CDCl$_3$: 3.57(s,3H),3.79(s,3H),4.23(s,2H),4.48;4.81(ABq,J = 16Hz,2H), 4.60(s,3H),5.02;5.07(2 × s,1H), 5.29(s,2H),6.19;6.24(2 × s,1H), 6.91(s,1H),7.20–7.69(m,10H). |
| 124 | (structure: ClCH=... S, CO—, N-H ring) | CH$_3$O | O | STet—CH$_3$ | H | Nujol: 3250,1780, 1690. | CDCl$_3$ + CD$_3$OD + D$_2$O 3.63(s,3H),3.97(s,3H),3.89–4.40(m,2H),4.30(brs,2H),4.61(s,2H),5.06;5.09(2 × s,1H), 6.13;6.19(2 × s,1H). |
| 125 | (structure: HO-CH-... S, CO—, N-H ring) | CH$_3$O | O | STet—CH$_3$ | CHPh$_2$ | CHCl$_3$: 3270,1785, 1700,1650. | CDCl$_3$ + CD$_3$OD: 2.5–3.3(m,2H),3.53;3.57(2 × s, 3H),3.80(s,3H),4.23(s,2H), 4.60(s,2H),5.03(s,1H),5.12(brs,1H),6.85(s,1H),7.2–7.6(m,10H). |
| 126 | (structure: HO-CH-... S, CO—, N-H ring) | CH$_3$O | O | STet—CH$_3$ | H | KBr: 3430,3310, 1785,1700, 1660. | CD$_3$OD: 2.3–3.2(m,2H),3.58;3.60(2 × s, 3H),4.03(s,3H),4.17(brs,1H), 4.30(s,2H),4.65(s,2H),5.12(s,1H). |
| 127 | (structure: C$_2$H$_5$O-CH-... S, CO—, N-H ring) | CH$_3$O | O | STet—CH$_3$ | CHPh$_2$ | CHCl$_3$: 3470,3330, 1790,1720, 1690. | CDCl$_3$ + CD$_3$OD: 1.10–1.42(m,3H), 2.6–3.27(m,2H), 3.33–3.97(m,2H),3.57;3.60(2 × s, 3H),3.83(s,3H),4.27(s,2H),4.62(s,2H),4.87(brs,1H),5.08(s,1H), 6.88(s,1H),7.20–7.65(m,10H). |

TABLE 3-continued $$A-NH-\underset{R}{\overset{R}{\underset{\|}{C}}}-\underset{N}{\overset{X}{\underset{\|}{C}}}-\underset{COOR^2}{\overset{CH_2R^1}{\underset{\|}{C}}}$$

$$\left( A: \begin{array}{c} Y-CHCO- \\ \times \\ Z-CO \end{array} \right)$$

| NO. | A | R | X | R¹ | R² | IR (cm⁻¹) | NMR (δppm) |
|---|---|---|---|---|---|---|---|
| 128 | (structure with S, CO, NH, C₂H₅O) | CH₃O | O | STet—CH₃ | H | KBr: 3440,3360, 1786,1703, 1656. | CD₃OD: 1.03–1.33(m,3H), 2.3–3.2(m,2H), 3.55(brs,3H),3.97(s,3H),4.25 (s,2H),4.60(s,2H),5.08(s,1H). |
| 129 | (structure with S, CO, N—CH₃) | H | S | (pyridinium) | H | KBr: 3430,1770, 1670,1615. | D₂O(TMS ext. ref.) 3.10–3.70(m,2H), 3.47(s,3H),4.1- 4.3(m,2H),3.93,4.20(ABq,2H, 19Hz),4.73(s,1H),5.56–5.70(m, 1H),5.82,6.02(ABq,2H,16Hz), 6.10(d,1H,5Hz),8.57(t,2H,7Hz), 9.07(t,1H,7Hz),9.45(d,2H,7Hz). |
| 130 | (structure with S, CO, N—CH₃) | H | O | H | CHPh₂ | CHCl₃: 3330,1790, 1720,1685, 1635. | CDCl₃: 2.03(s,3H),2.47–3.78(m,4H),3.02 (s,3H),4.22(brs,1H),4.32(brs, 2H),5.05(d,J = 4Hz,1H),5.65(dd, J = 4,7Hz,1H),6.88(s,1H),7.12– 7.68(m,10H). |
| 131 | (structure with S, CO, N—CH₃) | H | O | H | H | Nujol: 3220,1785, 1715,1620. | CDCl₃ + CD₃OD: 2.07(s,3H),2.50–4.03(m,4H), 3.07(s,3H),4.22(s,1H),4.40 (brs,2H),5.13(d,J = 4Hz,1H), 5.60(d,J = 4Hz,1H). |
| 132 | (structure with S, CO, N—CH₃) | CH₃O | O | OCONH₂ | CHPh₂ | CHCl₃: 3550,3430, 1790,1735, 1640. | CDCl₃: 2.6–3.3(m,2H),3.00(s,3H),3.3– 3.8(m,2H),3.55,3.57(2 × s,3H), 4.28(s,1H),4.50(s,2H),4.8–5.2 (m,6H),6.92(s,1H),7.1–7.6(m, 10H). |

TABLE 3-continued

A—NH—[structure with R, X, CH₂R¹, COOR², N, O]

A: [Y—CHCO— / Z—CO bracket structure]

| NO. | A | R | X | R¹ | R² | IR (cm⁻¹) | NMR (δppm) |
|---|---|---|---|---|---|---|---|
| 137 | [S-CO-N(CH₃) ring structure] | CH₃O | O | [imidazole with O₂N, N-CH₃, S-] | H | KBr: 3430,1780, 1720,1687, 1625,1530, 1500. | CDCl₃ + CD₃OD + CD₃SOCD₃: 2.5–4.0(m,4H),3.00(s,3H),3.48; 3.52(2 × s,3H),3.73(s,3H),3.93 (s,2H),4.57(s,2H),4.97;5.00 (2 × s,1H),7.75(s,1H). |
| 138 | [S-CO-N(CH₃) ring structure] | CH₃O | O | [imidazole with vinyl, N-CH₃, S-] | CHPh₂ | CHCl₃: 3320,1790, 1720,1630. | CDCl₃: 2.20–3.77(m,4H),2.82(s,3H), 3.42(s,3H),3.53;3.57(2 × s,3H), 4.12(brs,2H),4.30(s,1H),4.57 (brs,2H),5.02(s,1H),6.83(s, 1H),7.10–7.70(m,10H),8.00(s, 1H),8.40(brs,1H). |
| 139 | [S-CO-N(CH₃) ring structure] | CH₃O | O | [imidazole with vinyl, N-CH₃, S-] | H | Nujol: 3300,1770, 1790,1630. | CDCl₃ + CD₃OD: 3.03(s,3H),3.48(brs,3H),3.68 (brs,3H),4.30(brs,2H),4.55(s, 2H),5.03(brs,1H),8.42(s,1H). |
| 140 | [S-CO-N(CH₃) ring structure] | CH₃O | O | [imidazole with CF₃, N-CH₃, S-] | CHPh₂ | CHCl₃: 3370,1785, 1708,1628. | CDCl₃: 3.02(s,3H),3.58(s,3H),4.03(s, 1H),4.07(s,2H),4.60(s,2H), 5.03(s,1H),6.82(s,1H),7.2–7.7 (m,10H). |
| 141 | [S-CO-N(CH₃) ring structure] | CH₃O | O | [imidazole with CF₃, N-CH₃, S-] | H | KBr: 3370,2550, 1783,1708, 1696,1625. | CD₃COCD₃: 3.00(s,3H),3.52;3.54(2 × s,3H), 2.7–3.9(m,4H),3.85(s,3H),4.32 (s,3H),4.72(s,2H),5.12(s,1H). |

TABLE 3-continued $$A-NH \underset{\substack{R \\ \phantom{X}}}{\overset{\phantom{X}}{\underset{\phantom{X}}{\bigvee}}} \text{...} \underset{COOR^2}{\overset{CH_2R^1}{\diagdown}}$$

$$A: \left\{ \begin{array}{c} Y-CHCO- \\ \diagup\phantom{xx}\diagdown \\ Z-CO \end{array} \right\}$$

| NO. | A | R | X | R¹ | R² | IR (cm⁻¹) | NMR (δppm) |
|---|---|---|---|---|---|---|---|
| 142 | S-CH₂-CH₂-N(CH₃)-CO-CH(CO-) with ring | CH₃O | O | -N=C(S-)-N(CH₃)-CH=N (methylimidazole-thio) | CHPh₂ | CHCl₃: 1790,1710, 1630. | CDCl₃—CD₃OD: 2.55–3.80(m,4H),3.03(s,3H), 3.55;3.57(2 × s,3H),3.60(s,3H), 3.90(s,3H),3.96;4.16(ABq,2H, 13Hz),4.50(s,2H),4.55(s,1H), 5.06(s,1H),5.30(s,2H),6.82(s, 1H),7.2–7.6(m,10H). |
| 143 | S-CH₂-CH₂-N(CH₃)-CO-CH(CO-) | CH₃O | O | -N=C(S-)-N(CH₃)-CH=N | H | KBr: 3430,1780, 1690,1625. | CDCl₃—CD₃OD: 2.6–3.8(m,4H),3.02(s,3H),3.53; 3.55(2 × s,3H),3.74(s,3H),3.99 (s,3H),4.06(s,2H),4.18(s,1H), 4.56(t,2H),5.06(s,1H). |
| 144 | S-CH₂-CH₂-N(CH₃)-CO-CH(CO-) | CH₃O | O | -S-C₆H₄-Cl (p-chlorophenylthio via methylimidazole linker) | CHPh₂ | CHCl₃: | 2.5–3.4(m,2H),3.00;3.02(2 × s, 3H),3.45–3.70(m,2H),3.46(s, 3H),3.55;3.58(2 × s,3H),4.09 (s,2H),4.13(s,2H),4.25(s,1H), 4.54(bs,2H),5.02(s,1H),6.86 (s,1H),7.2–7.65(m,14H),8.10 (bs,1H). |
| 145 | S-CH₂-CH₂-N(CH₃)-CO-CH(CO-) | CH₃O | O | -S-C₆H₄-Cl | H | KBr: 1780,1692, 1625. | CD₃OD: 2.5–3.4(m,2H),3.01(s,3H),3.5– 3.8(m,2H),3.53;3.55(2 × s,3H), 3.68(s,3H),4.05(s,2H),4.19(s, 1H),4.30(s,2H),4.52(s,2H), 5.05(s,1H),7.34(s,4H). |

TABLE 3-continued $$A-NH \overset{R}{\underset{}{\diagdown}} \overset{X}{\underset{O}{\diagup}} N \overset{CH_2R^1}{\underset{COOR^2}{\diagdown}} \quad \left( A: \overset{Y-CHCO-}{\underset{Z}{\diagdown}} \right)$$

| NO. | A | R | X | R¹ | R² | IR (cm⁻¹) | NMR (δppm) |
|---|---|---|---|---|---|---|---|
| 146 | S-CO- / N-CH₃ (thiomorpholinone with CO) | CH₃O | O | N—N / S / N-CH₃ (methylthiadiazole) | CHPh₂ | CHCl₃: 1785,1705, 1630. | CDCl₃: 2.5–3.5(m,2H),3.02;3.03(2 × s, 3H),3.50(s,3H),3.57;3.60(2 × s, 3H),3.5–3.80(m,2H),4.15(s, 2H),4.25(s,2H),4.29(s,1H), 4.56(bs,2H),5.04(s,1H),6.89 (s,1H),7.1–7.7(m,12H),8.26 (s,1H),8.4–8.5(m,2H). |
| 147 | S-CO- / N-CH₃ | CH₃O | O | N—N / S / N-CH₃ | H | KBr: CF₃COOH 3430,1780, 1685,1625, 1195,1125. | CD₃OD: CF₃COOH 2.6–3.5(m,2H),3.02(s,3H), 3.51;3.53(2 × s,3H),3.74;3.76 (2 × s,3H),3.5–3.8(m,2H),3.9– 4.3(m,3H),4.5–4.66(m,2H), 4.74(s,2H),4.98;5.00(2 × s,1H), 7.89;8.49(ABq,2H,6Hz). |
| 148 | S-CO- / N-CH₃ | CH₃O | O | N—N / S (thiadiazole) | CHPh₂ | CHCl₃: 3300,1785, 1710,1625. | CDCl₃: 2.47–3.80(m,4H),2.98(s,3H), 3.53;3.57(2 × s,3H),4.33(s,2H), 4.43(s,1H),4.60(s,2H),5.03(s, 1H),6.90(s,1H),7.07–7.73(m, 10H). |
| 149 | S-CO- / N-CH₃ | CH₃O | O | N—N / S | Na | CHCl₃: 3200,1765, 1685,1610. | CDCl₃ + CD₃OD: 2.48–3.93(m,4H),3.05(s,3H), 3.52(s,3H),4.2–4.8(m,4H),5.00; 5.02(2 × s,1H),9.22(s,1H). |

TABLE 3-continued

![Structure: A-NH-R on beta-lactam with CH2R1, COOR2, X substituents]

A: {Y-CHCO- / Z-CO-cycle}

| NO. | A | R | X | R¹ | R² | IR (cm⁻¹) | NMR (δppm) |
|---|---|---|---|---|---|---|---|
| 150 | S-CO- / N-CH₃ ring (thiazine-one) | CH₃O | O | -S-thiadiazole-CH₃ | CHPh₂ | CHCl₃: 1790,1720, 1650. | CDCl₃: 2.4–3.9(m,4H),2.63(s,3H),2.97 (s,3H),3.52;3.53(2 × s,3H),4.28 (s,2H),4.40(s,1H),4.57(s,2H), 5.00(s,1H),6.88(s,1H),7.1–7.7 (m,10H),8.20(br,1H). |
| 151 | S-CO- / N-CH₃ ring | CH₃O | O | -S-thiadiazole-CH₃ | H | CHCl₃: 3300,1775, 1700,1625, 1605. | CDCl₃: 2.4–3.8(m,4H),2.73(s,3H),3.07 (s,3H),3.55;3.58(2 × s,3H),4.17; 4.50(ABq,J = 14Hz,2H),4.40(s, 1H),4.57(brs,2H),5.03(s,1H), 8.03(br,1H). |
| 152 | S-CO- / N-CH₃ ring | CH₃O | O | -S-thiadiazole-CH₂NH₂·CF₃COOH | H | Nujol: 1775,1675, 1620. | CDCl₃ + CD₃OD: 2.4–3.9(m,4H),3.52;3.53(2 × s,3H), 4.37(brs,3H),4.62(brs,4H),5.03 (s,1H). |
| 153 | S-CO- / N-CH₃ ring | CH₃O | O | -S-thiadiazole-CH₂NHCO-t-Bu | CHPh₂ | CHCl₃: 3440,1780, 1705,1690, 1615. | CDCl₃: 1.40(s,9H),2.4–3.8(m,4H),2.97 (s,3H),3.52;3.55(2 × s,3H),4.2– 4.6(m,7H),5.03(s,1H),5.65(br, 1H),6.90(s,1H),7.1–7.6(m,10H), 8.25(br,1H). |
| 154 | S-CO- / N-CH₃ ring | CH₃O | O | -S-thiadiazole-CH₂CN | H | Nujol: 1775,1690, 1620. | CDCl₃ + CD₃OD: 2.5–3.9(m,6H),3.05(s,3H),3.57; 3.60(2 × s,3H),4.40(brs,3H), 4.62(brs,2H),5.03(s,1H). |

TABLE 3-continued $$\text{A-NH} \overset{R}{\underset{}{\rule{0pt}{1em}}} \overset{X}{\underset{\underset{O}{\parallel}}{\rule{0pt}{1em}}} \overset{\underset{}{\rule{0pt}{1em}}}{\underset{N}{\rule{0pt}{1em}}} \overset{CH_2R^1}{\underset{COOR^2}{\rule{0pt}{1em}}} \quad \left( A: \overset{Y\text{—CHCO—}}{\underset{Z\quad CO}{\rule{0pt}{1em}\times\rule{0pt}{1em}}} \right)$$

| NO. | A | R | X | R$^1$ | R$^2$ | IR (cm$^{-1}$) | NMR (δppm) |
|---|---|---|---|---|---|---|---|
| 155 | (structure with S, CO, N-CH$_3$, O) | CH$_3$O | O | (thiadiazole-CH$_2$CN) | CHPh$_2$ | CHCl$_3$: 1785,1710, 1690,1615. | CDCl$_3$: 2.5–3.9(m,4H),3.00(s,3H),3.53; 3.57(2 × s,3H), 4.07(s,2H),4.27 (s,2H),4.40(s,1H),4.57(s,2H), 5.00(s,1H),6.83(s,1H),7.0–7.7 (m,10H),8.10(br,1H). |
| 156 | (structure with S, CO, N-CH$_3$, O) | CH$_3$O | O | (thiadiazole-CO-OC$_2$H$_5$) | H | CHCl$_3$: 3300,1775, 1710,1620, 1600. | CD$_3$COCD$_3$: 1.40(t,J = 7Hz,3H),2.4–3.9(m, 4H),3.00(s,3H),3.48;3.50(2 × s, 3H),4.30(s,1H),4.47(q,J = 7Hz, 2H),4.50(brs,2H),4.67(brs,2H), 5.13(s,1H),8.33(br,1H). |
| 157 | (structure with S, CO, N-CH$_3$, O) | CH$_3$O | O | (thiadiazole-CO-OC$_2$H$_5$) | CHPh$_2$ | CHCl$_3$: 1785,1730, 1720,1700, 1625. | CDCl$_3$: 1.40(t,J = 7Hz,3H),2.4–3.9(m, 4H),3.00(s,3H),3.55;3.58(2 × s, 3H),4.25–4.7(m,7H),5.05(s,1H), 6.95(s,1H),7.2–7.7(m,10H),8.12 (br,1H). |
| 158 | (structure with S, CO, N-CH$_3$, O) | CH$_3$O | O | (thiadiazole-CH$_2$-S-C(=N-N=)N-CH$_3$) | CHPh$_2$ | CHCl$_3$: 1790,1720, 1630. | CDCl$_3$: 2.5–3.4(m,2H),3.03(s,3H), 3.55;3.58(2 × s,3H),3.5–3.75 (m,2H),3.90(s,3H),4.25(s,1H), 4.26;4.43(ABq,2H,13Hz),4.58 (s,2H),4.85(s,2H),5.03(s,1H), 6.92(s,1H),7.25–7.60(m,10H), 8.06;8.13(2 × s,1H). |

TABLE 3-continued $$A-NH \begin{array}{c} R \\ | \\ \end{array} \underset{O}{\overset{X}{\diagup}} \underset{N}{\diagdown} \underset{COOR^2}{\overset{CH_2R^1}{\diagup}} \quad \left( A: \underset{Z}{\overset{Y-CHCO-}{\underset{CO}{\times}}} \right)$$

| NO. | A | R | X | R[1] | R[2] | IR (cm$^{-1}$) | NMR (δppm) |
|---|---|---|---|---|---|---|---|
| 159 | S—CH₂—CH₂—N(CH₃)—CH(CO—) | CH₃O | O | —S—(tetrazole-N(CH₃))— (thiadiazole-S-CH₂) | H | KBr: 3440,1780, 1695,1625. | CDCl₃: 2.5–3.4(m,2H),3.03(s,3H), 3.55;3.57(2 × s,3H),3.5–3.8(m, 2H),3.96(s,3H),4.20(s,1H), 4.30;4.43(ABq,2H,14Hz),4.58 (s,2H),4.92(s,2H),5.02;5.05 (2 × s,1H). |
| 160 | S—CH₂—CH₂—N(CH₃)—CH(CO—) | CH₃O | O | —S—(thiadiazole)-S-CH₂—(4-Cl-C₆H₄) | CHPh₂ | CHCl₃: 1790,1710, 1630. | CDCl₃: 2.5–3.4(m,2H),3.03(s,3H),3.5– 3.8(m,2H),3.56;3.58(2 × s,3H), 4.25(s,1H),4.23;4.43(ABq,2H, 15Hz),4.35(s,2H),4.57(s,2H), 5.01;5.03(2 × s,1H),6.92(s,1H), 7.1–7.65(m,14H),8.02;8.10 (2 × bs,1H). |
| 161 | S—CH₂—CH₂—N(CH₃)—CH(CO—) | CH₃O | O | —S—(thiadiazole)-S-CH₂—(4-Cl-C₆H₄) | H | KBr: 3430,1783, 1700,1626. | CD₃OD: 2.5–3.4(m,2H),3.00(s,3H),3.5– 3.8(m,2H),3.53;3.56(2 × s,3H), 4.18(s,1H),4.25;4.42(ABq,2H, 12Hz),4.50(s,2H),4.54(s,2H), 5.00;5.02(2 × s,1H),7.35(s,4H). |
| 162 | S—CH₂—CH₂—N(CH₃)—CH(CO—) | CH₃O | O | STet—CH₃ | CH₃ | Nujol: 3320,1768, 1717,1698, 1637. | d₆-DMSO: 2.50–3.80(m,4H),2.89(s,3H), 3.40;3.41(2 × s,3H),3.76(s,3H), 3.93(s,3H),4.20(s,1H),4.24 (s,2H),4.56(s,2H),5.10(s,1H), 9.17(s,1H). |

TABLE 3-continued

Structure: A—NH—[R, β-lactam with X, CH2R¹, COOR²]

A: Y—CHCO— / Z—CO (cyclic)

| NO. | A | R | X | R¹ | R² | IR (cm⁻¹) | NMR (δppm) |
|---|---|---|---|---|---|---|---|
| 163 | S-CO-CH(...)-N(CH3)-C(=O) ring | CH$_3$O | O | STet—CH$_3$ | CH$_2$C(=O)Ph | CHCl$_3$: 1783,1720, 1700,1666. | CDCl$_3$: 2.58–3.71(m,4H),3.01;3.03 (2 × s,3H),3.52;3.56(2 × s,3H), 3.91(s,3H),4.28(s,1H),4.30; 4.45(ABq,2H,14Hz),4.65(bs, 2H),5.09(s,1H),5.56(s,2H), 7.33–8.01(m,5H). |
| 164 | " | CH$_3$O | O | STet—CH$_3$ | CH$_2$-C$_6$H$_4$-NO$_2$ | CHCl$_3$: 1782,1713, 1698,1623, 1345,1256. | CDCl$_3$: 2.64–3.72(m,4H),3.01–3.03 (2 × s,3H),3.53;3.55(2 × s,3H), 3.91(s,3H),4.24(s,2H),4.37 (s,1H),4.63(s,2H),5.03(s, 1H),5.30;5.48(ABq,2H,16.5Hz), 7.67;8.24(ABq,4H,9.0Hz). |
| 165 | " | CH$_3$O | O | STet—CH$_3$ | CHPh$_2$ | CHCl$_3$: 3250,1790, 1710,1630. | CDCl$_3$: 2.47–3.90(m,4H),3.00(s,3H), 3.55;3.58(2 × s,3H),3.80(s, 3H),4.27(s,3H),4.62(s,2H), 5.03(s,1H),6.88(s,1H),7.10– 7.75(m,10H). |
| 166 | " | CH$_3$O | O | STet—CH$_3$ | POM | CHCl$_3$: 3275,1790, 1750,1700, 1625. | CDCl$_3$: 1.25(s,9H),3.03;3.07(2 × s,3H), 3.57;3.58(2 × s,3H),2.50–4.03(m, 4H),3.95(s,3H),4.27(s,3H),4.32 (brs,2H),4.67(brs,2H),5.07(s, 1H),5.93;6.05(ABq,J = 6Hz,2H). |
| 167 | " | CH$_3$O | O | STet—CH$_3$ | AOM | CHCl$_3$: 3300,1790, 1730,1700, 1670,1630. | CDCl$_3$: 2.17(s,3H),2.47–3.88(m,4H), 3.03(s,3H),3.55;3.58(2 × s,3H), 3.95(s,3H),4.28(brs,3H),4.65 (s,2H),5.05(s,1H),5.90;6.00 (ABq,J = 6Hz,2H). |

TABLE 3-continued

| NO. | A | R | X | R$^1$ | R$^2$ | IR (cm$^{-1}$) | NMR (δppm) |
|---|---|---|---|---|---|---|---|
| 168 | S–CO–/N–CH$_3$ (ring with C=O) | CH$_3$O | O | STet—CH$_3$ | BAK | CHCl$_3$: 3300,1790, 1760,1700, 1625. | CDCl$_3$: 1.33(t,J = 7Hz,3H),1.63(d,J = 6Hz, 3H),2.27–3.83(m,4H),3.02;3.03 2 × s,3H),3.57(s,3H),3.92(s,3H), 4.27(q,J = 7Hz,2H),4.30(brs,3H), 5.03(s,1H),6.93(q,J = 6Hz,1H). |
| 169 | S–CO–/N–CH$_3$ | CH$_3$O | O | STet—CH$_3$ | Ftdyl | CHCl$_3$: 3300,1795, 1735,1700, 1630. | CDCl$_3$: 2.47–3.82(m,4H),3.02,3.05(2 × s, 3H),3.43;3.47(2 × s,3H),3.92; 3.97(2 × s,3H),4.03–4.50(m,3H); 4.65(brs,2H),5.00;5.03(2 × s,1H), 7.52;7.43(2 × s,1H),7.57–8.23(m,4H). |
| 170 | S–CO–/N–CH$_3$ | CH$_3$O | O | STet—CH$_3$ | H | Nujol: 3220,1780, 1690,1620. | CDCl$_3$ + CD$_3$OD: 2.48–3.93(m,4H),3.03(s,3H), 3.57;3.58(2 × s,3H),3.97(s,3H), 4.20(s,1H),4.32(s,2H),4.62(s, 2H),5.07(s,1H). |
| 171 | S–CO–/N–CH$_3$ | CH$_3$O | O | STet—CH$_2$–CH$_3$ | CHPh$_2$ | CHCl$_3$: 3500,1781, 1702,1627. | CDCl$_3$: 1.43(t,J = 7Hz,3H),2.4–3.8(m,4H), 3.00(s,3H),3.55;3.58(2 × s,3H), 4.17(q,J = 7Hz,2H),4.28(s,3H), 4.63(s,2H),5.03(s,1H),6.92(s, 1H),7.2–7.6(m,10H),8.17(brs,1H). |

TABLE 3-continued

Structure: A—NH—CHR—[β-lactam with X, N]—C(COOR²)=CH-CH₂R¹

A: Y—CHCO—, Z—CO (cyclic)

| NO. | A | R | X | R¹ | R² | IR (cm⁻¹) | NMR (δppm) |
|---|---|---|---|---|---|---|---|
| 172 | S-CO-... N-CH₃ (thiazine-dione) | CH₃O | O | STet—CH₂—CH₃ | H | Nujol: 3480,3265, 2600,1784, 1699,1625, 1497. | CD₃COCD₃: 1.47(t,J = 7Hz,3H),2.5–4.0(m,4H), 2.97(s,3H),3.47,3.50(2 × s,3H), 4.27(s,1H),4.33(s,2H),4.35(q, J = 7Hz,2H),4.65(s,2H),5.07(s,1H),5.10(brs,2H). |
| 173 | S-CO-... N-CH₃ | CH₃O | O | STet—CH(CH₃)₂ | CHPh₂ | CHCl₃: 1785,1700, 1625. | CDCl₃: 1.53(d,J = 7Hz,6H),2.5–3.8(m,5H), 3.03(s,3H),3.57,3.60(2 × s,3H), 4.25-4.47(m,3H),4.67(brs,2H), 5.03(s,1H),6.93(s,1H),7.2–7.7(m,10H),8.07(brs,1H). |
| 174 | S-CO-... N-CH₃ | CH₃O | O | STet—CH(CH₃)₂ | H | KBr: 3340,1780, 1705,1615. | CD₃COCD₃: 1.55(d,J = 7Hz,6H),2.5–3.8(m,5H), 3.00(s,3H),3.50,3.53(2 × s,3H), 4.38(brs,3H),4.68(s,2H),5.10(s,1H). |

TABLE 3-continued $$\text{A NH} \underset{R}{\overset{X}{\underset{}{\bigvee}}} \underset{O}{\overset{}{\underset{N}{\bigvee}}} \underset{COOR^2}{\overset{CH_2R^1}{\bigvee}} \quad \left( A: \underset{Z}{\overset{Y-CHCO-}{\underset{}{\bigvee}}} \underset{CO}{\overset{}{\bigvee}} \right)$$

| NO. | A | R | X | R$^1$ | R$^2$ | IR (cm$^{-1}$) | NMR (δppm) |
|---|---|---|---|---|---|---|---|
| 180 | S-CO-, N-CH$_3$ (with C=O) | CH$_3$O | O | STet—CF$_2$—H | H | KBr: 1785, 1695, 1625. | CDCl$_3$ + CD$_3$OD: 2.4–3.8(m,7H),3.03(s,3H),4.20 (s,1H),4.43(s,2H),4.62(s,2H), 5.07(s,1H),7.62(t,J = 57Hz,1H). |
| 176 | S-CO-, N-CH$_3$ | CH$_3$O | O | STet—CH$_2$ H$_2$NCONH | CHPh$_2$ | CHCl$_3$: 3380,1785, 1700,1625. | CD$_3$COCD$_3$: 2.50–3.78(m,4H),2.93;2.95(2 × s, 3H),3.53;3.56(2 × s,3H),4.20; 4.37(ABq,J = 14Hz,2H),4.33(s, 1H),4.62(s,2H),5.12(s,3H), 6.94(s,1H),7.10–7.77(m,10H). |
| 182 | S-CO-, N-CH$_3$ | CH$_3$O | O | STet—CH$_2$ H$_2$NCONH | H | Nujol: 3150,1760, 1680,1600. | D$_2$O(Na—Salt): 3.17–4.37(m,4H),3.49(s,3H), 4.01;4.02(2 × s,3H),4.57;4.78 (ABq,J = 14Hz,2H),4.99(s,2H), 5.51;5.52(2 × s,1H),5.76(s,2H). |
| 183 | S-CO-, N-CH$_3$ | CH$_3$O | O | STet—CH$_2$ (CH$_3$)$_2$NCH$_2$ | CHPh$_2$ | CHCl$_3$: 1780,1700, 1620. | CDCl$_3$: 1.87(s,6H),2.4–3.7(m,4H),2.67 (t,J = 7Hz,2H),3.00(s,3H),3.55; 3.58(2 × s,3H),4.12–4.30(m,5H), 4.60(brs,2H),5.00(s,1H),6.87 (s,1H),7.1–7.6(m,10H),8.10(br, 1H). |

TABLE 3-continued

| NO. | A | R | X | R¹ | R² | IR (cm⁻¹) | NMR (δppm) |
|---|---|---|---|---|---|---|---|
| 184 | S-CO-/N-CH₃ (thiazinone) | CH₃O | O | STet—CH₂ (CH₃)₂NCH₂ CF₃COOH | H | Nujol: 1780,1700, 1670,1620. | CDCl₃ + CD₃OD: 2.5–3.8(m,4H),2.98(s,6H),3.03 (s,3H),3.53(s,3H),3.70(brs,2H), 4.0–4.3(m,3H),4.50–4.80(m,4H). |
| 185 | S-CO-/N-CH₃ | CH₃O | O | STet—CH₂ CN | CHPh₂ | CHCl₃: 1790,1710, 1630,1450. | CDCl₃: 2.4–4.0(m,4H),2.98(s,3H),3.52; 3.57(2 × s,3H),4.23(brs,3H), 4.55(s,2H),4.98;5.02(2 × s,1H), 5.08(s,2H),6.87(s,1H),7.2–7.6 (m,10H),8.10(brs,1H). |
| 186 | S-CO-/N-CH₃ | CH₃O | O | STet—CH₂ CN | H | KBr: 3440,1783, 1695,1625, 1500. | CDCl₃ + CD₃OD: 2.4–3.9(m,4H),3.05(s,3H),3.57 (brs,3H),4.18(brs,1H),4.30(s, 2H),4.60(brs,2H),5.07(s,1H), 5.45(s,2H). |
| 187 | S-CO-/N-CH₃ | CH₃O | O | STet—CH₂ Ph₂CHOCO | CHPh₂ | CHCl₃: 3250,1790, 1750,1710, 1630. | CDCl₃: 2.30–3.80(m,4H),2.97(s,3H), 3.53;3.57(2 × s,3H),4.17(brs,2H), 4.27(s,1H),4.50(brs,2H),5.00 (s,1H),5.03(brs,2H),6.90(s,2H), 7.00–7.75(m,20H). |
| 188 | S-CO-/N-CH₃ | CH₃O | O | STet—CH₂ HOCO | H | Nujol: 3200,1780, 1730,1700, 1610. | CDCl₃ + CD₃OD: 2.55–4.00(m,4H),3.05(s,3H), 3.58(s,3H),4.33(s,2H),4.55(s, 2H),5.08(s,1H),5.10(s,2H). |

TABLE 3-continued $$A-NH-\overset{R}{\underset{O}{\overline{\bigsqcup}}}\overset{X}{\underset{COOR^2}{\bigvee}}\overset{CH_2R^1}{\underset{COOR^2}{\bigvee}} \quad \left\{ A: \underset{Z}{\overset{Y-CHCO-}{\underset{CO}{\bigvee}}} \right\}$$

| NO. | A | R | X | R[1] | R[2] | IR (cm$^{-1}$) | NMR (δppm) |
|---|---|---|---|---|---|---|---|
| 189 | ![S-CO / N-CH3 structure] | CH$_3$O | O | STet—CH$_2$—CH$_3$OCO | CHPh$_2$ | CHCl$_3$: 3350,1790, 1760,1710, 1630. | CDCl$_3$: 2.4–3.87(m,4H),2.97(s,3H),3.52; 3.55(2 × s,3H),3.73(s,3H),4.23 (brs,3H),4.53(brs,2H),4.93(brs, 2H),5.00(s,1H),6.83(s,1H),7.08– 7.63(m,10H). |
| 190 | ![same] | CH$_3$O | O | STet—CH$_2$—CH$_3$OCO | H | Nujol: 3280,1785, 1755,1700, 1625. | CDCl$_3$ + CD$_3$OD: 2.48–3.99(m,4H),3.05(s,3H), 3.55;3.57(2 × s,3H),3.83(s,3H), 4.32(brs,2H),4.58(brs,2H), 5.08(s,1H),5.18(brs,2H). |
| 191 | ![same] | CH$_3$O | O | STet—CH$_2$—H$_2$N—CO | CHPh$_2$ | CHCl$_3$: 1785,1700, 1630. | CDCl$_3$ + CD$_3$OD + D$_2$O: 2.5–3.8(m,4H),2.95(s,3H),3.53; 3.55(2 × s,3H),4.17(s,2H),4.50 (s,2H),4.63(s,1H),4.93(s,2H), 5.03(s,1H),6.87(s,1H),7.1–7.3 (m,10H). |
| 192 | ![same] | CH$_3$O | O | STet—CH$_2$—H$_2$NCO | H | KBr: 3420,1780, 1687,1623. | CDCl$_3$ + CD$_3$OD: 2.5–3.9(m,4H),3.03(s,3H),3.53; 3.55(2 × s,3H),4.20(s,2H),4.27 (s,2H),4.53(s,2H),5.05(s,3H). |

TABLE 3-continued $$\text{ANH}\overset{R}{\underset{\underset{O}{\parallel}}{\diagup}}\overset{X}{\underset{N}{\diagdown}}\overset{CH_2R^1}{\underset{COOR^2}{\diagdown}} \quad \left( A: Z\overset{Y-CHCO-}{\underset{CO}{\diagup}} \right)$$

| NO. | A | R | X | R¹ | R² | IR (cm⁻¹) | NMR (δppm) |
|---|---|---|---|---|---|---|---|
| 193 | ![S ring with CO-, N-CH₃, O] | CH₃O | O | CH₃<br>STet—CH<br>\|<br>H₂N—CO | CHPh₂ | CHCl₃:<br>3320,1790,<br>1700,1630. | CDCl₃ + CD₃OD:<br>1.82(d,J = 7Hz,3H),2.3–3.8(m,<br>11H),4.20(s,3H),4.48(s,2H),<br>4.8–5.2(m,2H),6.82(s,1H),7.1–<br>7.7(m,10H). |
| 194 | ![S ring with CO-, N-CH₃, O] | CH₃O | O | CH₃<br>STet—CH<br>\|<br>H₂NCO | H | KBr:<br>3300,1795,<br>1695,1625. | CDCl₃ + CD₃OD:<br>1.92(d,J = 8Hz,3H),2.5–3.2(m,<br>5H),3.2–3.8(m,2H),4.25(s,3H),<br>4.52(s,2H),4.9–5.4(m,2H). |
| 195 | ![S ring with CO-, N-CH₃, O] | CH₃O | O | STet—CHF<br>\|<br>H₂N—CO | CHPh₂ | CHCl₃:<br>3475,3400,<br>1790,1730,<br>1630. | CDCl₃:<br>2.38–3.92(m,4H),2.93(s,3H),<br>3.50,3.53(2 × s,3H),4.25(brs,<br>2H),4.48(brs,2H),5.02(s,1H),<br>6.60(d,J = 48Hz,1H),6.70(s,1H),<br>6.78–7.68(m,10H). |
| 196 | ![S ring with CO-, N-CH₃, O] | CH₃O | O | STet—CHF<br>\|<br>H₂NCO | H | Nujol:<br>3250,1775,<br>1700,1615. | CDCl₃ + CD₃OD:<br>2.27–3.88(m,4H),3.03(s,3H),<br>3.53,3.57(2 × s,3H),3.88–4.07<br>(m,2H),4.58(brs,2H),5.07(s,<br>1H),6.83(d,J = 47Hz,1H). |

TABLE 3-continued

| NO. | A | R | X | R¹ | R² | IR (cm⁻¹) | NMR (δppm) |
|---|---|---|---|---|---|---|---|
| 197 | S-CO-/N-CH₃ (with C=O) | CH₃O | O | STet—CH₂ / PMBONHCO | CHPh₂ | CHCl₃: 3340,3200, 1790,1705, 1670,1625. | CDCl₃: 2.5–3.9(m,4H),2.96,2.97(2 × s, 3H),3.54,3.57(2 × s,3H),3.76 (s,3H),4.03;4.23(ABq,J = 14Hz, 2H),4.19(s,1H),4.47(brs,2H), 4.77(s,2H),4.83(s,2H),4.98; 5.01(2 × s,1H),6.98(s,1H),6.80–7.67(m,14H). |
| 198 | S-CO-/N-CH₃ | CH₃O | O | STet—CH₂ / HONHCO | H | Nujol: 3200,1780, 1690,1620. | CDCl₃ + CD₃OD: 2.3–3.9(m,4H),3.04(s,3H),3.55; 3.57(2 × s,3H),4.21(brs,2H), 4.54(brs,2H),4.97(brs,2H), 5.06(s,1H). |
| 199 | S-CO-/N-CH₃ | CH₃O | O | STet—CH₂ / CH₃ONHCO | CHPh₂ | CHCl₃: 3340,3200, 1785,1705, 1625. | CDCl₃: 2.43–3.7(m,4H),2.99;3.01(2 × s, 3H),3.56;3.58(2 × s,3H),3.67(s, 3H),4.05;4.26(ABq,J = 13Hz,2H), 4.27(s,1H),4.47(brs,2H),4.93 (brs,2H),5.01;5.04(2 × s,1H), 6.89(s,1H),7.13–7.66(m,10H), 8.14(brs,1H). |
| 200 | S-CO-/N-CH₃ | CH₃O | O | STet—CH₂ / CH₃ONHCO | H | Nujol: 3220,1785, 1700,1625. | CDCl₃ + CD₃OD: 2.5–3.9(m,4H),3.04(s,3H),3.56; 3.58(2 × s,3H),3.77(s,3H),4.19 (brs,2H),4.56(brs,2H),4.97 (brs,2H),5.06(s,1H). |

TABLE 3-continued

| NO. | A | R | X | R¹ | R² | IR (cm⁻¹) | NMR (δppm) |
|---|---|---|---|---|---|---|---|
| 201 | (S, CO—, N–CH₃, =O ring) | CH₃O | O | STet—CH₂-(morpholinone with NCO, HN, =O) | CHPh₂ | — | CD₃COCD₃: 2.5–4.5(m,1H),2.97(s,3H),3.55, 3.58(2 × s,3H),4.25(s,2H),4.62 (s,2H),5.12(s,1H),5.48(s,2H), 6.92(s,1H),7.22–7.8(m,10H), 8.46(brs,1H). |
| 202 | (S, CO—, N–CH₃, =O ring) | CH₃O | O | STet—CH₂-(morpholinone with NCO, HN, =O) | H | Nujol: 3280,1787, 1670,1640. | CD₃SOCD₃: 2.88(s,3H),3.45;3.47(2 × s,3H), 3.91(brs,1H),4.15(brs,2H), 4.22(brs,2H),4.48(brs,2H), 5.02(s,1H),5.50(s,2H),8.05(brs, 1H),9.08(s,1H). |
| 203 | (S, CO—, N–CH₃, =O ring) | CH₃O | O | STet—CH₂-(piperazinedione with N-C₂H₅, =O, =O) | CHPh₂ | CHCl₃: 3300,1790, 1700,1645. | CDCl₃ + CD₃OD: 0.97–1.48(m,3H),3.02(brs,3H), 2.32–4.02(m,10H),3.55;3.58(2 × s, 3H),4.22(brs,3H),4.58(brs,2H), 4.92(brs,2H),5.07(s,1H),6.85 (s,1H),7.12–7.68(m,10H). |

TABLE 3-continued

Structure:

A—NH—[R on C]—(ring with X, N, C=O)—CH=C(CH₂R¹)(COOR²)

A: { Y—CHCO— / Z—CO }

| NO. | A | R | X | R¹ | R² | IR (cm⁻¹) | NMR (δppm) |
|---|---|---|---|---|---|---|---|
| 204 | S-ring with CO—, N—CH₃, C=O | CH₃O | O | STet—CH₂—CO—N(ring with two C=O and N—C₂H₅) | H | Nujol: 3280, 1785, 1735, 1690, 1630. | CDCl₃ + CD₃OD: 1.08–1.50(m,3H),2.17–4.55(m,13H),3.05(s,3H),3.55,3.58(2×s,3H),4.58(brs,2H),5.05(s,1H),5.08(brs,2H). |
| 205 | S-ring with CO—, N—CH₃, C=O | CH₃O | O | STet—DL—(ring with C=O, NH) | CHPh₂ | CHCl₃: 1790, 1725, 1700, 1630. | CDCl₃: 2.4–3.8(m,8H),3.00(s,3H),3.53,3.57(2×s,3H),4.25(brs,3H),4.52(brs,2H),5.03(s,1H),4.86–5.26(m,1H),6.90(s,1H),7.16–7.66(m,10H),8.13(brs,1H). |
| 206 | S-ring with CO—, N—CH₃, C=O | CH₃O | O | STet—DL—(ring with C=O, NH) | H | KBr: 3320, 1785, 1715, 1627. | CDCl₃ + CD₃OD: 2.4–4.0(m,8H),3.02(s,3H),3.53,3.55(2×s,3H),4.17(s,1H),4.33(brs,2H),4.57(brs,2H),5.05(s,1H),5.27(t,J=9Hz,1H). |
| 207 | S-ring with CO—, N—CH₃, C=O | CH₃O | O | STet—DL—(ring with C=O, NH) | CHPh₂ | CHCl₃: 1790, 1690, 1635. | CDCl₃ + CD₃OD: 1.8–3.8(m,10H),3.00(s,3H),3.53,3.57(2×s,3H),4.20(brs,3H),4.55(brs,2H),4.8–5.2(m,1H),5.03–5.07(2×s,1H),6.87(s,1H),7.2–7.6(m,10H). |

TABLE 3-continued $$\text{ANH} \underset{O}{\overset{R}{\underset{\|}{\bigsqcup}}} \underset{\text{CH}_2\text{R}^1}{\overset{X}{\underset{\text{COOR}^2}{\bigsqcup}}} \quad \left( \text{A:} \underset{Z}{\overset{Y-\text{CHCO}-}{\underset{\text{CO}}{\bigsqcup}}} \right)$$

| NO. | A | R | X | R¹ | R² | IR (cm⁻¹) | NMR (δppm) |
|---|---|---|---|---|---|---|---|
| 208 | S-CO-/N-CH₃ pyrrolidinone | CH₃O | O | STet—CH₂ / L (piperidinone with NH) | H | KBr: 3420,3340, 1785,1675, 1630 | CDCl₃ + CD₃OD: 1.8–3.9(m,10H),3.02(s,3H),3.52; 3.55(2 × s,3H),4.17(s,1H),4.27 (brs,2H),4.57(brs,2H),5.03; 5.05(2 × s,1H),4.9–5.3(m,1H). |
| 209 | S-CO-/N-CH₃ | CH₃O | O | STet—CH₂ / NC—CH₂ | CHPh₂ | CHCl₃: 1790,1710, 1630,1400 | CDCl₃: 2.4–3.9(m,4H),2.92(t,J = 6Hz,2H), 3.00(s,3H),3.53;3.57(2 × s,3H), 4.23(brs,3H),4.37(t,J = 6Hz,2H), 4.57(s,2H),5.00(s,1H),6.83(s, 1H),7.2–7.6(m,10H),8.03(brs,1H). |
| 210 | S-CO-/N-CH₃ | CH₃O | O | STet—CH₂ / NCCH₂ | H | KBr: 3420,2250, 1782,1695, 1625,1500 | CDCl₃ + CD₃OD: 2.4–4.0(m,4H),3.03(s,3H),3.15 (t,J = 6Hz,2H),3.53;3.57(2 × s, 3H),4.18(s,1H),4.30(s,2H), 4.60(t,J = 6Hz,2H),5.05(s,1H). |
| 211 | S-CO-/N-CH₃ | CH₃O | O | STet—CH₂ / H₂NCOCH₂ | CHPh₂ | CHCl₃: 3350,1790, 1700,1690, 1630 | CDCl₃ + CD₃OD: 2.43–3.85(m,6H),2.97(s,3H), 3.55;3.57(2 × s,3H),4.22(brs,3H), 4.30–4.42(m,2H),4.55(brs,2H), 5.05(s,1H),6.85(s,1H),7.10– 7.70(m,10H). |
| 212 | S-CO-/N-CH₃ | CH₃O | O | STet—CH₂ / H₂NCOCH₂ | H | Nujol: 3300,1780, 1670,1620 | CDCl₃ + CD₃OD: 2.50–3.87(m,6H),2.92(m,2H), 3.03(s,3H),3.57(s,3H),4.22– 4.42(m,2H),4.33(brs,2H),4.57 (brs,3H),5.07(s,1H). |

TABLE 3-continued $$\text{ANH}\underset{\underset{O}{\parallel}}{\overset{R}{\underset{|}{C}}}\hspace{-2pt}\underset{N}{\overset{X}{\diagup}}\hspace{-2pt}\overset{CH_2R^1}{\underset{COOR^2}{\diagdown}}$$

$$\left( A: \underset{Z}{\overset{Y-CHCO-}{\diagdown\hspace{-2pt}/}}\underset{CO}{\overset{}{\diagdown}} \right)$$

| NO. | A | R | X | R¹ | R² | IR (cm⁻¹) | NMR (δppm) |
|---|---|---|---|---|---|---|---|
| 213 | ![structure with S, CO-, N-CH₃, O] | CH₃O | O | STet—CH₂<br>NCON—CH₂<br>H₂  H | CHPh₂ | CHCl₃:<br>3500,3385,<br>1785,1710,<br>1668,1628,<br>1256. | CDCl₃:<br>2.51–3.75(m,6H),2.94,2.99(2 × s,<br>3H),3.60(s,3H),4.13–4.85(m,<br>7H),4.98,5.03(2 × s,1H),5.95(t,<br>1H,6Hz),6.93(s,1H),7.29–7.61<br>(m,10H),8.37,8.96(2 × s,1H). |
| 214 | ![structure with S, CO-, N-CH₃, O] | CH₃O | O | STet—CH₂<br>NCONCH₂<br>H₂  H | H | Nujol:<br>3350,1780,<br>1685,1625. | d₆-DMSO + CD₃OD:<br>2.90(s,3H),3.40,3.44(2 × s,3H),<br>3.62(t,2H,7Hz),4.18–4.37(m,<br>5H),4.56(s,2H),5.05,5.07(2 × s,<br>1H),9.15(s,1H). |
| 215 | ![structure with S, CO-, N-CH₃, O] | CH₃O | O | STet—CH₂<br>CH₂<br>H₂N—SO₂ | CHPh₂ | CHCl₃:<br>1785,1700,<br>1630. | CDCl₃:<br>2.4–4.0(m,6H),2.95(s,3H),3.53;<br>3.58(2 × s,3H),4.28(brs,3H),<br>4.53(brs,4H),5.03;5.07(2 × s,<br>1H),5.70(brs,2H),6.90(s,1H),<br>7.2–7.7(m,10H),8.13(brs,1H). |
| 216 | ![structure with S, CO-, N-CH₃, O] | CH₃O | O | STet—CH₂<br>CH₂<br>H₂NSO₂ | H | KBr:<br>3480,3300,<br>1780,1690,<br>1623,1500. | CDCl₃ + CD₃OD:<br>2.4–4.0(m,4H),3.03(s,3H),3.53;<br>3.57(s,3H),3.68(t,J = 7Hz,2H),<br>4.17(s,1H),4.28(brs,2H),4.57<br>(brs,2H),4.75(t,J = 7Hz,2H),<br>5.05(s,1H). |

TABLE 3-continued $$\text{A NH} \overset{R}{\underset{O}{\diagup}} \overset{X}{\underset{N}{\diagdown}} \overset{CH_2R^1}{\underset{COOR^2}{=}} \quad \left\{ A: \overset{Y-CHCO-}{\underset{Z}{\diagdown}} \overset{}{\underset{CO}{\diagdown}} \right\}$$

| NO. | A | R | X | R[1] | R[2] | IR (cm$^{-1}$) | NMR (δppm) |
|---|---|---|---|---|---|---|---|
| 217 | S-CO- attached to N-CH₃ piperidinone | CH₃O | O | 2-pyridyl-S- | CHPh₂ | CHCl₃: 1775,1700, 1620. | CDCl₃: 2.4–3.8(m,4H),3.00(s,3H),3.53; 3.57(2 × s,3H),4.27(brs,2H), 4.40(brs,1H),4.53(brs,2H),5.00 (s,1H),6.93(s,1H),7.1–8.3(m, 14H). |
| 218 | -CO- N-CH₃ amide | CH₃O | O | 2-pyridyl-S- CF₃COOH | H | KBr: 3400,1780, 1680,1625. | CD₃OD: 2.5–3.8(m,4H),3.00(s,3H),3.53 (s,3H),4.23(ABq, J = 14Hz,2H), 4.33(s,1H),4.53(s,2H),5.00(s, 1H),6.9–8.5(m,4H). |
| 219 | S-CO- attached to N-CH₃ piperidinone | CH₃O | O | (2-hydroxy-3-oxo-1-methyl-pyridazinyl)-S- | CHPh₂ | CHCl₃: 3200,1790, 1760,1715, 1630,1600. | ND. |
| 220 | S-CO- attached to N-CH₃ piperidinone | CH₃O | O | (2-hydroxy-3-oxo-1-methyl-pyridazinyl)-S- | H | Nujol: 3250,1775, 1680,1620. | D₂O(Na—Salt): 3.45(brs,3H),3.98(brs,3H), 4.05(brs,3H),5.58(s,1H). |
| 221 | S-CO- attached to N-CH₃ piperidinone | CH₃O | O | triazolopyridinyl-S- | CHPh₂ | CHCl₃: 3380,1785, 1710,1630. | CDCl₃: 2.40–3.87(m,4H),2.97(s,1H),3.53; 3.57(2 × s,3H),4.02–4.62(m,2H), 4.33(brs,1H),4.62(brs,2H),5.05 (s,1H),6.92(s,1H),7.10;8.00(ABq, J = 9Hz,2H),6.83–7.68(m,10H). |

TABLE 3-continued $$A-NH-\overset{R}{\underset{\phantom{O}}{\overset{\phantom{O}}{\bigsqcup}}}\overset{X}{\underset{O}{\bigsqcup}}\overset{CH_2R^1}{\underset{COOR^2}{\bigsqcup}} \quad \left( A: Z\overset{Y-CHCO-}{\underset{CO}{\bigsqcup}} \right)$$

| NO. | A | R | X | R¹ | R² | IR (cm⁻¹) | NMR (δppm) |
|-----|---|---|---|----|----|-----------|------------|
| 222 | S−CO− / −N−CH₃ (with C=O) | CH₃O | O | triazolopyridazine-S- (with CH=CH) | H | Nujol: 3275,1780, 1700,1625. | CDCl₃ + CD₃OD: 2.30–3.90(m,4H),3.03(brs,3H), 3.58(brs,3H),4.15–4.73(m,3H), 4.65(s,2H),5.07(s,1H),7.42; 8.25(ABq,J = 9Hz,2H). |
| 223 | S−CO− / −N−CH₃ (with C=O) | CH₃O | O | NH₂-triazolopyridazine-S- | CHPh₂ | CHCl₃: 1790,1720, 1630. | CDCl₃: 2.4–3.8(m,4H),2.97(brs,3H), 3.53;3.57(2 × s,3H),4.23(brs, 1H),4.33(brs,2H),4.60(brs,2H), 5.05(s,1H),6.17(s,1H),6.30 (brs,2H),6.93(s,1H),7.2–7.6 (m),8.27(brs,1H). |
| 224 | S−CO− / −N−CH₃ (with C=O) | CH₃O | O | NH₂-triazolopyridazine-S- | H | KBr: 3420,3350, 1690,1625, 1570. | CD₃OD: 2.5–3.9(m,4H),3.53;3.55(2 × s, 3H),4.05–4.60(m,3H),4.65(s, 2H),5.03;5.05(2 × s,1H),6.35 (s,1H). |
| 225 | S−CO− / −N−CH₃ (with C=O) | CH₃O | O | pyridinium | ⊖ | KBr: 3420,1775, 1680,1620. | CD₃OD + D₂O: 2.8–4.2(m,4H),3.00(s,3H),3.56 (s,3H),4.40(brs,2H),5.3;6.0 (ABq,J = 16Hz,2H),8.1–9.5(m, 5H). |

TABLE 3-continued $$A\text{NH}\underset{O}{\overset{R}{\underset{\displaystyle N}{\bigsqcup}}}\overset{X}{\underset{\displaystyle COOR^2}{\bigvee}}CH_2R^1 \qquad \left( A: \underset{\displaystyle Z}{\overset{Y-CHCO-}{\underset{\displaystyle CO}{\bigvee}}} \right)$$

| NO. | A | R | X | R¹ | R² | IR (cm⁻¹) | NMR (δppm) |
|---|---|---|---|---|---|---|---|
| 226 | ![S-CO-CH(C=O)N(C2H5)-] structure | $CH_3O$ | O | STet—$CH_3$ | $CHPh_2$ | $CHCl_3$: 3300,1790, 1705,1625. | $CDCl_3$: 0.93–1.43(m,3H),2.48–3.97(m, 6H),3.55;3.58(2 × s,3H),3.82(s, 3H),4.25(brs,3H),4.61(brs,2H), 5.03(s,1H),6.83(s,1H),6.98– 7.68(m,10H). |
| 227 | ![same structure] | $CH_3O$ | O | STet—$CH_3$ | POM | $CHCl_3$: 3300,1795, 1750,1730, 1700,1630. | $CDCl_3$: 0.90–1.40(m,3H),1.23(s,9H), 2.40–3.77(m,6H),3.50;3.53(2 × s, 3H),3.90(s,3H),4.22(s,1H), 4.27(s,2H),4.60(s,2H),5.02(s, 1H),5.88;5.95(ABq,J = 6Hz,2H). |
| 228 | ![same structure] | $CH_3O$ | O | STet—$CH_3$ | K | Nujol: 3300,1770, 1680,1600. | $CDCl_3$ + $CD_3OD$: 0.83–1.57(m,6H),2.50–4.17(m, 6H),3.48(s,3H),3.90(s,3H), 4.40(brs,2H),4.63(brs,2H), 5.07(s,1H). |
| 229 | ![S-CO-CH(C=O)N(CH2CH2CH3)-] structure | $CH_3O$ | O | STet—$CH_3$ | $CHPh_2$ | $CHCl_3$: 3300,1785, 1705,1625. | $CDCl_3$: 0.68–1.08(m,3H),1.33–1.82(m, 2H),2.50–3.87(m,6H),3.53; 3.57(2 × s,3H),3.77(s,3H),4.25 (brs,3H),4.60(bs,2H),5.02(s, 1H),6.88(s,1H),7.10–7.67(m, 10H). |
| 230 | ![same structure] | $CH_3O$ | O | STet—$CH_3$ | POM | $CHCl_3$: 3300,1790, 1750,1730, 1700,1625. | $CDCl_3$: 0.70–1.07(m,3H),1.23(s,9H), 1.40–1.83(m,2H),2.50–3.95(m, 6H),3.52;3.55(2 × s,3H),3.95(s, 3H),4.30(brs,3H),4.63(bs,2H), 5.03(s,1H),5.20;6.00(ABq,J = 6Hz,2H). |

TABLE 3

$$A-NH-\underset{R}{\overset{}{C}}-\underset{}{\overset{X}{C}}-N-\underset{COOR^2}{\overset{CH_2R^1}{C}}=O \quad \left( A: \underset{Z}{\overset{Y-CHCO}{\underset{CO}{X}}} \right)$$

| NO. | A | R | X | R¹ | R² | IR (cm⁻¹) | NMR (δppm) |
|---|---|---|---|---|---|---|---|
| 231 | S-CO-<br>N-CH₂CH₂CH₃<br>(with C=O) | CH₃O | O | STet—CH₃ | K | Nujol:<br>3175,1765,<br>1680,1605. | CDCl₃ + CD₃OD:<br>0.90(t,J = 6Hz,3H),1.23–1.83<br>(m,2H),2.50–4.07(m,6H),3.47<br>(s,3H),3.97(s,3H),4.37(s,3H),<br>4.73(s,2H),5.00(s,1H). |
| 232 | S-CO-<br>N-CH(CH₃)₂<br>(with C=O) | CH₃O | O | STet—CH₃ | CHPh₂ | CHCl₃:<br>3360,1790,<br>1715,1630. | CDCl₃:<br>1.15(d,J = 6Hz,6H),2.68–3.70(m,<br>4H),3.60(s,3H),3.83(s,3H),<br>4.27(brs,3H),4.63(brs,2H),<br>4.47–5.20(m,1H),5.07(s,1H),<br>6.90(s,1H),7.10–7.70(m,10H). |
| 233 | S-CO-<br>N-CH(CH₃)₂<br>(with C=O) | CH₃O | O | STet—CH₃ | POM | CDCl₃:<br>3300,1790,<br>1750,1730,<br>1700,1630. | CDCl₃:<br>1.15(d,J = 7Hz,6H),1.20(s,9H),<br>2.50–3.72(m,4H),3.50:3.53(2 × s,<br>3H),3.93(s,3H),4.27(brs,3H),<br>4.62(s,2H),4.47–5.17(m,1H),<br>5.03(s,1H),5.83;5.97(ABq,<br>J = 6Hz). |
| 234 | S-CO-<br>N-CH(CH₃)₂<br>(with C=O) | CH₃O | O | STet—CH₃ | K | Nujol:<br>3300,1770,<br>1680,1600. | CDCl₃ + CD₃OD:<br>1.13(d,J = 7Hz,6H),2.53–3.73(m,<br>4H),3.43(s,3H),3.93(s,3H),<br>4.37(brs,2H),4.58(brs,2H),5.00<br>(s,1H),4.17–5.07(m,2H). |

TABLE 3-continued

| NO. | A | R | X | R¹ | R² | IR (cm⁻¹) | NMR (δppm) |
|---|---|---|---|---|---|---|---|
| 235 | S with tetrahydropyran, CO—N—CH₂CH₂O ring | CH₃O | O | STet—CH₃ | CHPh₂ | CHCl₃: 3300,1785, 1700,1620. | CDCl₃: 1.23–1.95(m,6H),3.60,3.62(2 × s, 3H),3.82(s,3H),2.50–4.05(m, 10H),4.30(brs,3H),4.63(brs, 3H),5.07(s,1H),6.93(s,1H), 7.15–7.73(m,10H). |
| 236 | S, CO—N—CH₂CH₂OH ring | CH₃O | O | STet—CH₃ | CHPh₂ | CHCl₃: 3350,1785, 1710,1625. | CDCl₃: 2.43–4.00(m,8H),3.55,3.57(2 × s, 3H),3.77(s,3H),4.27(s,1H), 4.30(s,2H),4.62(brs,2H),5.05 (s,1H),6.95(s,1H),7.13–7.75 (m,10H). |
| 237 | S, CO—N—CH₂CH₂OH ring | CH₃O | O | STet—CH₃ | H | Nujol: 3250,1780, 1690,1615. | CDCl₃ + CD₃OD: 2.50–4.10(m,8H),3.58(s,3H), 3.97(s,3H),4.32(s,2H),4.62 (s,2H),5.08(s,1H). |
| 238 | S, CO—N—CH₂CH₂Cl ring | CH₃O | O | STet—CH₃ | CHPh₂ | CHCl₃: 3350,1785, 1710,1630. | CDCl₃: 2.50–4.03(m,4H),3.60(s,3H), 3.73(brs,4H),3.83(s,3H),4.30 (brs,3H),5.08(s,1H),6.92(s, 1H),7.15–7.73(m,10H). |
| 239 | S, CO—N—CH₂CH₂Cl ring | CH₃O | O | STet—CH₃ | H | Nujol: 3250,1780, 1700,1625. | CDCl₃ + CD₃OD: 2.53–4.03(m,4H),3.60(s,3H), 3.77(brs,4H),3.98(s,3H),4.33 (brs,2H),4.65(brs,2H),5.10 (s,1H). |

TABLE 3-continued

| NO. | A | R | X | R¹ | R² | IR (cm⁻¹) | NMR (δppm) |
|---|---|---|---|---|---|---|---|
| 240 | S–CO–  N–CH₂OCH₃ (O) | CH₃O | O | STet—CH₃ | CHPh₂ | CHCl₃: 3325,1785, 1705,1640. | CDCl₃: 2.50–4.00(m,4H),3.28;3.32(2 × s, 3H),3.55;3.58(2 × s,3H),3.78(s, 3H),4.25(s,2H),4.33(s,1H), 4.62(s,2H),4.73–5.00(m,2H), 5.08(s,1H),6.92(s,1H),7.10–7.72 (m,10H). |
| 241 | S–CO–  N–CH₂OCH₃ (O) | CH₃O | O | STet—CH₃ | H | Nujol: 3250,1785, 1695,1635. | CDCl₃ + CD₃OD: 2.57–4.07(m,4H),3.35(s,3H), 3.57;3.58(2 × s,3H),3.97(s,3H), 4.32(brs,3H),4.63(s,2H),4.77–5.03 (m,2H),5.10(s,1H). |
| 242 | S–CO–  N–CH₂Ph (O) | CH₃O | O | STet—CH₃ | CHPh₂ | CHCl₃: 3350,1790, 1715,1635. | CDCl₃: 2.30–3.80(m,4H),3.50;3.53(2 × s, 3H),3.68(s,3H),4.20(brs,2H), 4.53(brs,2H),4.10–4.77(m,3H), 5.00(s,1H),6.83(s,1H),7.00–7.68 (m,15H). |
| 243 | S–CO–  N–CH₂Ph (O) | CH₃O | O | STet—CH₃ | POM | CHCl₃: 3300,1790, 1750,1730, 1700,1630. | CDCl₃: 1.23(s,9H),1.42–3.73(m,4H), 3.52;3.53(2 × s,3H),3.88(s,3H), 4.28(brs,2H),4.60(brs,2H), 4.13–4.83(m,3H),5.87,6.02 (ABq,J = 6Hz,2H),7.27(s,5H). |

TABLE 3-continued $$A-NH-\underset{\underset{O}{\|}}{\overset{R}{C}}\text{(structure with X, CH}_2R^1\text{, COOR}^2\text{)} \quad \left(A: \begin{array}{c} Y-CHCO-\\ X\\ Z-CO \end{array}\right)$$

| NO. | A | R | X | R¹ | R² | IR (cm⁻¹) | NMR (δppm) |
|---|---|---|---|---|---|---|---|
| 244 | S-CH(CO-)-C(=O)-N(CH₂PH)-CH₂-CH₂ ring | CH₃O | O | STet—CH₃ | K | Nujol: 3350,1770, 1690,1610. | CDCl₃ + CD₃OD: 2.5–4.8(m,5H), 3.47(s,3H),3.93(s,3H),4.38 (brs,2H),4.60(brs,2H),4.67 (brs,2H),5.03(s,1H),7.25 (s,5H). |
| 245 | S-CH(CO-)-C(=O)-N(COCH₃)-CH₂-CH₂ ring | CH₃O | O | STet—CH₃ | CHPh₂ | CHCl₃: 3350,1790, 1715. | CDCl₃:2.55(s,3H),2.63–3.90(m,3H), 3.57;3.60(2 × s,3H),3.78(s,3H), 4.10–4.97(m,1H),4.23(brs,2H), 4.33(s,1H),4.63(brs,2H),5.05; 5.10(2 × s,1H),6.90(s,1H), 7.13–7.77(m,10H). |
| 246 | S-CH(CO-)-C(=O)-N(COCH₃)-CH₂-CH₂ ring | CH₃O | O | STet—CH₃ | H | Nujol: 3280,1780, 1700. | CDCl₃ + CD₃OD: 2.58(s,3H),2.78–4.15(m,3H), 3.58(s,3H),3.98(s,3H),4.15–4.90 (m,1H),4.33(brs,2H),4.65 (brs,2H),5.10;5.13(2 × s,1H). |
| 247 | S-CH(CO-)-C(=O)-N(COCH₂CN)-CH₂-CH₂ ring | CH₃O | O | STet—CH₃ | CHPh₂ | CHCl₃: 3350,1790, 1720. | CDCl₃: 2.50–3.17(m,2H),3.33–3.92(m, 1H),3.58;3.62(2 × s,3H),3.78 (s,3H),4.17(s,2H),4.20(s,2H), 4.37(s,1H),4.33–4.93(m,1H), 4.67(brs,2H),5.07;5.13(2 × s, 1H),6.93(s,1H),7.13–7.73(m, 10H). |

TABLE 3-continued $$A-NH-\underset{R}{\underset{|}{\overset{R}{\cdot}}}\underset{O}{\overset{X}{\underset{N}{\diagup}}}\underset{COOR^2}{\overset{CH_2R^1}{\diagdown}} \quad \left\{ A: \underset{Z}{\overset{Y-CHCO-}{\underset{CO}{\diagdown}}} \right\}$$

| NO. | A | R | X | R¹ | R² | IR (cm⁻¹) | NMR (δppm) |
|---|---|---|---|---|---|---|---|
| 248 | ![S-CO ring with N-COCH₂CN] | CH₃O | O | STet—CH₃ | H | Nujol: 3300,1785, 1705. | CDCl₃ + CD₃OD: 2.55–3.28(m,2H),3.58(s,3H), 4.00(s,3H),4.28(s,2H),4.37 (s,2H),4.63(brs,2H),5.08; 5.13(2 × s,1H),3.3–4.8(m,3H). |
| 249 | ![S-CO ring with N-CONH₂] | CH₃O | O | STet—CH₃ | CHPh₂ | CHCl₃: 3500,3320, 1790,1725. | CDCl₃: 2.72–4.97(m,4H),3.57;3.61(2 × s, 3H),3.79(s,3H),4.24(brs,2H), 4.35(s,1H),4.54(brs,2H),5.06; 5.11(2 × s,1H),6.91(s,1H),7.13–7.65 (m,10H). |
| 250 | ![S-CO ring with N-CONH₂] | CH₃O | O | STet—CH₃ | H | Nujol: 3400,3280, 1780,1705. | CD₃SOCD₃: 2.78–4.82(m,5H),3.47(s,3H), 3.96(s,3H),4.23(s,2H),4.58 (s,2H),5.08;5.13(2 × s,1H). |
| 251 | ![S-CO ring with N-CH₂CN] | CH₃O | O | STet—CH₃ | CHPh₂ | CHCl₃: 3350,1785, 1705. | CDCl₃: 2.50–3.90(m,4H),3.53;3.57(2 × s, 3H),3.76(s,3H),4.00–4.46(m, 3H),4.23(s,2H),4.52(s,2H), 5.34(s,1H),6.89(s,1H),7.10–7.67 (m,10H). |
| 252 | ![S-CO ring with N-CH₂CN] | CH₃O | O | STet—CH₃ | H | Nujol: 3260,1780, 1690,1630. | CDCl₃ + CD₃OD: 2.60–3.90(m,4H),3.54;3.58(2 × s, 3H),3.96(s,3H),4.15–4.77 (m,3H),4.31(s,2H),4.61(s,2H), 5.04;5.06(2 × s,1H). |

TABLE 3-continued $$A-NH \underset{R}{\overset{X}{\diagdown}} \underset{O}{\overset{}{\diagdown}} N \underset{COOR^2}{\overset{CH_2R^1}{\diagdown}} \quad \left( A: \underset{Z}{\overset{Y-CHCO}{\diagdown}} \underset{CO}{\overset{}{\diagdown}} \right)$$

| NO. | A | R | X | R¹ | R² | IR (cm⁻¹) | NMR (δppm) |
|---|---|---|---|---|---|---|---|
| 253 | S–CO–CH(–)–C(=O)–N(CH₂COO–t-C₄H₉)–CH₂CH₂– (thiazolidinone ring) | CH₃O | O | STet—CH₃ | CHPh₂ | CHCl₃: 3250,1795, 1720,1640. | CDCl₃: 1.45(s,9H),2.50–4.17(m,6H), 3.57(brs,3H),3.78(s,3H),4.27 (brs,3H),4.62(brs,2H),5.05 (s,1H),6.90(s,1H),7.17–7.73 (m,10H). |
| 254 | S–CO–CH(–)–C(=O)–N(CH₂COOH)–CH₂CH₂– | CH₃O | O | STet—CH₃ | H | Nujol: 3300,1795, 1710,1630. | CDCl₃ + CD₃OD: 2.50–4.17(m,6H),3.55;3.57(2 × s, 3H),3.98(s,3H),4.32(brs,3H), 4.62(s,2H),5.07(s,1H). |
| 255 | S–CO–CH(–)–C(=O)–N(CH₂CONH₂)–CH₂CH₂– | CH₃O | O | STet—CH₃ | CHPh₂ | CHCl₃: 3470,3330. | CDCl₃: 2.42–3.94(m,4H),3.53;3.55(2 × s, 3H),3.79(s,3H),4.10–4.78 (m,3H),4.22(brs,2H),4.63(brs, 2H),5.04,5.06(2 × s,1H),6.90 (s,1H),7.18–7.67(m,10H). |
| 256 | S–CO–CH(–)–C(=O)–N(CH₂CONH₂)–CH₂CH₂– | CH₃O | O | STet—CH₃ | H | Nujol: 3250,1780, 1665,1625. | CD₃SOCD₃: 2.63–4.65(m,7H),3.41;3.45(2 × s, 3H),3.95(s,3H),4.23(brs, 2H),4.56(brs,2H),5.08;5.11 (2 × s,1H). |

TABLE 3-continued $$A-NH-\underset{\underset{O}{\overset{R}{|}}}{\overset{}{\underset{}{\bigg|}}}\overset{X}{\underset{N}{\bigg|}}\overset{CH_2R^1}{\underset{COOR^2}{\bigg|}} \quad \left\{ A: \overset{Y-CHCO}{\underset{Z}{\overset{}{\underset{CO}{\bigg|}}}} \right\}$$

| NO. | A | R | X | R$^1$ | R$^2$ | IR (cm$^{-1}$) | NMR (δppm) |
|---|---|---|---|---|---|---|---|
| 257 | ![structure with S, CO—, N—CH₃, CH₃] | CH$_3$O | O | STet—CH$_3$ | H | CHCl$_3$: 1785, 1710, 1620. | CDCl$_3$: 1.32–1.50(m,3H), 2.2–3.2(m,2H), 3.00(s,3H), 3.57; 3.60(2 × s,3H), 3.85(s,3H), 3.37–3.90(m,1H), 4.10(brs,1H), 4.30(s,2H), 4.63 (s,2H), 5.05(s,1H), 6.93(s,1H), 7.2–7.7(m,10H), 7.92(brs,1H). |
| 258 | ![structure with S, CO—, N—CH₃, CH₃] | CH$_3$O | O | STet—CH$_3$ | POM | CHCl$_3$: 1790, 1750, 1700, 1620. | CDCl$_3$: 1.30(s,9H), 1.37–1.53(m,3H), 2.2–3.3(m,2H), 3.00(s,3H), 3.53; 3.57(2 × s,3H), 3.4–3.9(m,1H), 3.93(s,3H), 4.07(brs,1H), 4.30 (s,2H), 4.65(s,2H), 5.05(s,1H), 5.90, 5.99(ABq,J = 6Hz,2H), 7.77 (brs,1H). |
| 259 | ![structure with S, CO—, N—CH₃, CH₃] | CH$_3$O | O | STet—CH$_3$ | H | KBr: 3440, 1788, 1706, 1622. | CD$_3$OD: 1.32–1.50(m,3H), 2.3–3.2(m,2H), 2.97(s,3H), 3.53; 3.55(2 × s,3H), 3.4–4.1(m,2H), 3.97(s,3H), 4.25 (s,2H), 4.60(s,2H), 5.05(s,1H). |
| 260 | ![structure with S, CO—, N—CH₃, NC] | CH$_3$O | O | STet—CH$_3$ | CHPh$_2$ | CHCl$_3$: 2240, 1790, 1710, 1640. | CDCl$_3$: 2.4–3.4(m,4H), 3.00(s,3H), 3.4–4.4 (m,4H), 3.55; 3.60(2 × s,3H), 3.78(s,3H), 4.65(s,2H), 5.07(s, 1H), 6.97(s,1H), 7.1–7.7(m,10H). |

TABLE 3-continued $$A-NH\underset{R}{\overset{}{\underset{}{\bigg|}}}\underset{O}{\overset{X}{\underset{N}{\bigg|}}}\underset{COOR^2}{\overset{CH_2R^1}{\bigg|}} \quad \left(A: \underset{Z}{\overset{Y-CHCO-}{\underset{CO}{\bigg|}}}\right)$$

| NO. | A | R | X | R¹ | R² | IR (cm⁻¹) | NMR (δppm) |
|---|---|---|---|---|---|---|---|
| 261 | (structure with NC, S, CO, N-CH₃) | CH₃O | O | STet—CH₃ | H | KBr: 3440,2260, 1632. | CDCl₃ + CD₃OD: 2.5–3.2(m,4H),3.08(s,3H),3.8–4.4 (m,7H),4.63(s,2H),5.08 (s,1H). |
| 262 | (structure with CH₃, S, CO, N-CH₃) | CH₃O | O | STet—CH₃ | CHPh₂ | CHCl₃: 3300,1790, 1710,1630. | CDCl₃: 1.17–1.31(m,3H),2.82(s,3H), 3.53;3.57(2 × s,3H),3.77(s,3H), 3.13–3.90(m,3H),4.27(brs,3H), 4.62(s,2H),5.03(s,1H),6.73 (s,1H),7.07–7.73(m,10H). |
| 263 | (structure with CH₃, S, CO, N-CH₃) | CH₃O | O | STet—CH₃ | POM | CHCl₃: 3300,1790, 1750,1700, 1625. | CDCl₃: 1.18–1.38(m,3H),1.23(s,9H), 3.03(brs,3H),3.38–3.65(m,3H), 3.53;3.55(2 × s,3H),3.92(s,3H), 4.17(s,1H),4.28(s,2H),4.62(s, 2H),5.02(s,1H),5.87;5.92(ABq, J = 5Hz,2H). |
| 264 | (structure with CH₃, S, CO, N-CH₃) | CH₃O | O | STet—CH₃ | H | Nujol: 3200,1780, 1690,1620. | CDCl₃ + CD₃OD: 1.25(d,J = 6Hz,3H),3.02(s,3H), 3.55(s,3H),3.93(s,3H),3.18–3.83 (m,3H),4.17(s,1H),4.28(s, 2H),4.60(s,2H),5.03(s,1H). |
| 265 | (structure with Ph, S, CO, N-CH₃) | CH₃O | O | STet—CH₃ | CHPh₂ | CHCl₃: 3300,1790, 1705,1630. | CDCl₃: 2.93;2.98(2 × s,3H),3.60(brs, 3H),3.72(brs,3H),3.20–4.97 (m,4H),4.23(brs,2H),4.60(brs, 2H),5.08;5.12(2 × s,1H),6.90(s, 1H),7.00–7.73(m,15H). |

TABLE 3-continued

| NO. | A | R | X | R¹ | R² | IR (cm⁻¹) | NMR (δppm) |
|---|---|---|---|---|---|---|---|
| 266 | Ph-CH(S)-CH2-N(CH3)-C(=O)-CH-CO- | CH₃O | O | STet—CH₃ | H | Nujol: 3250,1785, 1695,1620. | CDCl₃ + CD₃OD: 3.05(brs,3H),3.60(s,3H),3.95 (s,3H),4.02–4.80(m,4H),4.33 (brs,2H),4.62(brs,2H),5.12 (s,1H),7.37(s,5H). |
| 267 | CH₂=C(S)-CH2-N(CH3)-C(=O)-CH-CO- | CH₃O | O | STet—CH₃ | CHPh₂ | CHCl₃: 3380,1795, 1720,1670. | CDCl₃: 2.98;3.00(2 × s,3H),3.53(s,3H), 3.73(s,3H),3.78–4.45(m,2H), 4.22(s,2H),4.47(s,1H),4.58 (brs,2H),4.95–5.22(m,2H), 5.02(s,1H),6.88(s,1H),7.12–7.75 (m,10H). |
| 268 | CH₃-C(S)=CH-N(CH3)-C(=O)-CH-CO- | CH₃O | O | STet—CH₃ | H | Nujol: 3200,1780, 1700,1640. | CDCl₃ + CD₃OD: 3.07(s,3H),3.57(brs,3H),3.83–4.43 (m,3H),3.97(brs,3H),4.32 (brs,2H),4.62(brs,2H),5.08 (brs,1H),5.02–5.33(m,2H). |
| 269 | Cl-CH=C(S)-CH2-N(CH3)-C(=O)-CH-CO- | CH₃O | O | STet—CH₃ | CHPh₂ | CHCl₃: 3370,1790, 1710,1670. | CDCl₃: 3.00;3.02(2 × 3H),3.57(s,3H), 3.78(s,3H),4.07–4.77(m,3H), 4.23(brs,2H),4.62(brs,2H), 5.05(s,1H),6.07;6.13(2 × s,1H), 6.90(s,1H),7.17–7.72(m,10H). |

TABLE 3-continued $$A-NH\underset{O}{\overset{R}{\underset{\|}{\bigsqcup}}}\underset{COOR^2}{\overset{X}{\underset{\|}{\diagdown}}}\overset{CH_2R^1}{\underset{\|}{\diagup}}\quad\left(A:\overset{Y-CHCO}{\underset{Z}{\overset{|}{\diagdown}}}\underset{CO}{\overset{|}{\diagup}}\right)$$

| NO. | A | R | X | R¹ | R² | IR (cm⁻¹) | NMR (δppm) |
|---|---|---|---|---|---|---|---|
| 270 | ClCH=... S, CO—, N—CH₃, O | CH₃O | O | STet—CH₃ | H | Nujol: 3200,1780, 1700,1650. | CDCl₃ + CD₃OD: 3.07;3.10(2 × 3H),3.57(s,3H), 3.77–4.80(m,3H),4.30(brs,2H), 4.60(brs,2H),5.07(s,1H),6.13; 6.18(2 × 2,1H). |
| 271 | O=S, CO—, N—CH₃, O | CH₃O | O | STet—CH₃ | CHPh₂ | CHCl₃: 3380,1790, 1710,1650. | CDCl₃: 2.67–3.90(m,4H),3.10(s,3H), 3.57;3.62(2 × s,3H),3.67(s,3H), 4.30(s,2H),4.65(brs,2H),5.07 (s,1H),6.93(s,1H),7.03–7.73 (m,10H). |
| 272 | O=S, CO—, N—CH₃, O | CH₃O | O | STet—CH₃ | K | Nujol: 3350,1780, 1700,1610. | CDCl₃ + CD₃OD: 2.67–4.08(m,4H),3.08(s,3H), 3.58(s,3H),3.95(s,3H),4.35 (brs,3H),4.63(s,2H),5.08(s, 1H). |
| 273 | S, CO—, O, O | CH₃O | O | STet—CH₃ | CHPh₂ | CHCl₃: 3350,1790, 1725. | CDCl₃: 2.80–3.17(m,2H),3.53;3.57(2 × s, 3H),3.77(s,3H),4.22(s,2H), 4.32–4.68(m,2H),4.43(s,1H), 4.60(brs,2H),5.03;5.07(2 × s, 1H),6.87(s,1H),7.08–7.68(m, 10H). |

TABLE 3-continued $$A-NH\underset{\underset{O}{\overset{R}{\rightarrow}}}{\overset{X}{\underset{}{\bigg\vert}}}\underset{COOR^2}{\overset{CH_2R^1}{\bigg\vert}}\quad\left(A:\underset{Z}{\overset{Y-CHCO}{\underset{CO}{\bigg\vert}}}\right)$$

| NO. | A | R | X | R¹ | R² | IR (cm⁻¹) | NMR (δppm) |
|---|---|---|---|---|---|---|---|
| 274 | S-CO- / O (6-membered S,O ring with CO) | CH₃O | O | STet—CH₃ | H | Nujol: 3280,1780, 1730. | CDCl₃ + CD₃OD: 2.95–3.28(m,2H),3.58;3.61(2 × s, 3H),3.98(s,3H),4.48(s,2H), 4.57–4.82(m,2H),4.65(brs,2H), 5.10;5.12(2 × s,1H). |
| 275 | CO- / 7-membered N—H lactam ring | CH₃O | O | STet—CH₃ | CHPh₂ | CHCl₃: 3410,1788, 1715,1690, 1650,1500. | CDCl₃: 1.3–2.5(m,6H),2.9–3.4(m,3H), 3.57(s,3H),3.78(s,3H),4.27(s, 2H),4.62(s,2H),5.07(s,1H), 6.63(brs,1H),6.90(s,1H),7.1–7.7 (m,10H). |
| 276 | CO- / 7-membered N—H lactam ring | CH₃O | O | STet—CH₃ | H | KBr: 3400,1780, 1692,1636, 1515. | CD₃OD: 1.5–2.4(m,6H),3.1–3.5(m,3H), 3.52(s,3H),3.95(s,3H),4.24(s, 2H),4.62(s,2H),5.07(s,1H). |
| 277 | S / CO- / 7-membered S,NH ring | CH₃O | O | STet—CH₃ | CHPh₂ | CHCl₃: 3410,1790, 1705,1670. | CDCl₃: 1.5–2.2(m,2H),2.6–3.5(m,4H), 3.57(s,3H),3.77(s,3H),4.1–4.5 (m,3H),4.63(s,2H),5.05;5.10 (2 × s,1H),6.67(brs,1H),6.93(s, 1H),7.1–7.7(m,10H). |
| 278 | S / CO- / 7-membered S,NH ring | CH₃O | O | STet—CH₃ | H | KBr: 3370,1782, 1700,1650. | CDCl₃ + CD₃OD + D₂O: 1.7–2.2(m,2H),2.8–3.5(m,4H), 3.57(s,3H),3.97(s,3H),4.32(s, 3H),4.63(s,2H),5.07;5.12(2 × s, 1H). |

TABLE 3-continued

| NO. | A | R | X | R¹ | R² | IR (cm⁻¹) | NMR (δppm) |
|---|---|---|---|---|---|---|---|
| 279 | ![S-containing ring with CO and N-CH₃] | CH₃O | O | STet—CH₃ | CHPh₂ | CHCl₃: 1790,1700, 1645. | CDCl₃: 1.6–2.1(m,2H),2.6–3.7(m,4H), 2.97(s,3H),3.60(s,3H),3.78 (s,3H),4.27(s,2H),4.47,4.50 (2 × s,1H),4.62(s,1H),5.03, 5.07(2 × s,1H),6.92(s,1H),7.1–7.7 (m,10H). |
| 280 | ![S-containing ring with CO and N-CH₃] | CH₃O | O | STet—CH₃ | H | KBr: 3420,1780, 1700,1630. | CDCl₃ + CD₃OD: 1.8–2.2(m,2H),2.8–3.2(m,2H), 3.02(s,3H),3.3–3.7(m,2H), 3.57(s,3H),3.93(s,3H),4.32 (s,2H),4.50(s,1H),4.62(s, 2H),5.05,5.08(2 × s,1H). |
| 281 | ![S-containing ring with CO and N-CH₃] | CH₃O | O | ![heterocycle with 4-Cl-phenyl-S] | CHPh₂ | — | CDCl₃: 2.5–3.4(m,2H),3.00;3.02(2 × s, 3H),3.45–3.70(m,2H),3.46(s, 3H),3.55;3.58(2 × s,3H),4.09 (s,2H),4.13(s,2H),4.25(s, 1H),4.54(bs,2H),5.02(s,1H), 6.86(s,1H),7.2–7.65(m,14H), 8.10(bs,1H). |
| 282 | ![S-containing ring with CO and N-CH₃] | CH₃O | O | ![heterocycle with 4-Cl-phenyl-S] | H | KBr: 1780,1692, 1625. | CD₃OD: 2.5–3.4(m,2H),3.01(s,3H), 3.5–3.8(m,2H),3.53;3.55(2 × s, 3H),3.68(s,3H),4.05(s,2H), 4.19(s,1H),4.30(s,2H), (s,2H),5.05(s,1H),7.34(s, 4H). |

TABLE 3-continued $$A-NH-\underset{\underset{O}{\|}}{\overset{R}{\underset{|}{C}}}-\underset{N}{\overset{X}{\diagup}}\overset{CH_2R^1}{\diagdown}COOR^2 \quad \left( A: \begin{array}{c} Y-CHCO- \\ | \\ Z \end{array} \right)$$

| NO. | A | R | X | R¹ | R² | IR (cm⁻¹) | NMR (δppm) |
|---|---|---|---|---|---|---|---|
| 283 | S-CO-, N-CH₃ ring with C=O | CH₃O | O | 4-Cl-C₆H₄-S-CH₂-C(=N-N=)-S- (thiadiazole) | CHPh₂ | CHCl₃: 1790,1710, 1630. | CDCl₃: 2.5–3.4(m,2H),3.02(s,3H), 3.5–3.8(m,2H),3.56;3.58(2 × s, 3H),4.25(s,1H),4.23;4.43 (ABq,15Hz,2H),4.35(s,2H), 4.57(s,2H),5.01;5.03(2 × s, 1H),6.92(s,1H),7.1–7.65(m, 14H),8.02;8.10(bs,1H). |
| 284 | S-CO-, N-CH₃ ring with C=O | CH₃O | O | 4-Cl-C₆H₄-S-CH₂-C(=N-N=)-S- (thiadiazole) | H | KBr: 3430,1783, 1700,1626. | CD₃OD: 2.5–3.8(m,2H),3.00(s,3H), 3.5–3.8(m,2H),3.53;3.56(2 × s, 3H),4.18(s,1H),4.25;4.42 (ABq,12Hz,2H),4.50(s,2H), 4.53(s,2H),5.00;5.02(2 × s, 1H),7.35(s,4H). |
| 285 | S-CO-, N-CH₃ ring with C=O | H | S | pyridinium-CH₂- | ⊖ | KBr: 3430,1770, 1670,1615. | D₂O: 3.10–3.7(m,2H),3.47(s,3H), 4.1–4.3(m,2H),3.93;4.20(ABq, 19Hz,2H),4.73(s,1H),5.82; 6.02(ABq,16Hz,2H),5.56–5.70 (m,1H),6.10(d,5Hz,1H),8.57 (t,7Hz,2H),9.07(t,7Hz,1H), 9.45(d,7Hz,2H). |
| 286 | S-CO-, N-CH₃ ring with C=O | CH₃O | O | N-CH₃ tetrazole-S-CH₂-C(=N-N=)-S- | CHPh₂ | CHCl₃: 1790,1720, 1630. | CDCl₃: 2.5–3.4(m,2H),3.03(s,3H), 3.55;3.58(2 × s,3H),3.5–3.75 (m,2H),3.90(s,3H),4.25(s, 1H),4.26;4.43(ABq,13Hz,2H), 4.58(s,2H),4.85(s,2H),5.03 (s,1H),6.92(s,1H),7.25–7.60 (m,10H),8.06;8.13(2 × s, 1H). |

TABLE 3-continued

| NO. | A | R | X | R¹ | R² | IR (cm⁻¹) | NMR (δppm) |
|---|---|---|---|---|---|---|---|
| 287 | | CH₃O | O | | H | KBr: 3440,1780, 1695,1625. | CD₃OD—CDCl₃ 2.5–3.4(m,2H),3.03(s,3H), 3.55,3.57(2 × s,3H),3.5–3.8 (m,2H),3.96(s,3H),4.20(s, 1H),4.30;4.43(ABq,14Hz,2H), 4.58(s,2H),4.92(s,2H),5.02; 5.05(2 × s,1H) |
| 288 | | CH₃O | O | | CHPh₂ | CHCl₃: 1785,1705, 1630. | CDCl₃: 2.5–3.5(m,2H),3.02;3.03(2 × s, 3H),3.50(s,3H),3.57;3.60 (2 × s,3H),3.5–3.8(m,2H),4.15 (s,2H),4.25(s,2H),4.29(s, 1H),4.56(bs,2H),5.04(s,1H), 6.89(s,1H),7.1–7.7(m,12H), 8.26(s,1H),8.4–8.5(m,2H). |
| 289 | | CH₃O | O | .CF₃COOH | H | KBr: 3430,1780, 1685,1625, 1195,1125. | CD₃OD: 2.6–3.5(m,2H),3.02(s,3H), 3.51;3.53(2 × s,3H),3.74;3.76 (2 × s,3H),3.5–3.8(m,2H),3.9–4.3 (m,3H),4.5–4.66(m,2H), 4.74(s,2H),4.98;5.00(2 × s,1H), 7.89(d,6Hz,2H),8.49(d,6Hz, 2H). |
| 290 | | CH₃O | O | | CHPh₂ | CHCl₃: 1790,1710, 1630. | CDCl₃—CD₃OD: 2.55–3.80(m,4H),3.03(s,3H), 3.55;3.57(2 × 3H),3.60(s,3H), 3.90(s,3H),3.96;4.16(ABq,13 Hz,2H),4.50(s,2H),4.55(s, 1H),5.06(s,1H),5.30(s,2H), 6.82(s,1H),7.2–7.6(m,10H). |
| 291 | | CH₃O | O | | H | KBr: 3430,1780, 1690,1625. | CD₃OD.CDCl₃: 2.6–3.8(m,4H),3.02(s,3H), 3.53;3.55(2 × s,3H),3.74(s,3H), 3.99(s,3H),4.06(s,2H),4.18 (s,1H),4.56(s,2H),5.06(s, 1H). |

We claim:

1. 7β-(Oxo saturated heterocyclic carbonamino)-3-cephem-4-carboxylic acid compound of the following formula:

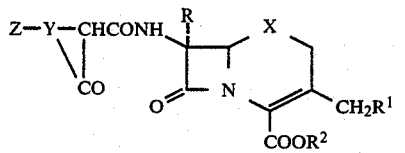

wherein R is hydrogen or methoxy;
R¹ is hydrogen or a nucleophilic group having 1 to 8 carbon atoms excluding any protective group and is 4 to 6C heterocyclicammonio or its anion, 1 to 3C alkanoyloxy, carbamoyloxy optionally N-protected, halo, 4 to 8 C heterocyclic thio or heterocyclic sulfoxido;
R² is hydrogen, light metal, or a carboxy protecting group;
X is oxygen;
Y is alkylene containing one or more hetero atom; and
Z is hydrogen or a substituent having up to 8 carbon atoms and being selected from the group consisting alkyl, aralkyl, alkylidene, aryl, alkanoyl, carbamoyl, hydroxy, alkoxy, oxo and sulfoxide, which may be unsubstituted or further substituted by carboxy, carbamoyl, cyano, hydroxy which is protected or unprotected, or halogen.

2. 7β-(Oxo saturated heterocyclic carbonamino)-3-cephem-4-carboxylic acid compound of the following formula:

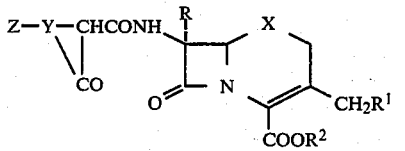

wherein
R is hydrogen or methoxy;
R¹ is hydrogen or nucleophilic group having 1 to 8 carbon atoms excluding any protective group and is 4 to 6 C heterocyclicammonio or its anion, 1 to 3 C alkanoyloxy, carbamoyloxy optionally N-protected, halo, 4 to 8 C heterocyclic thio or heterocyclic sulfoxido;
R² is hydrogen, light metal, or a carboxy protecting group;
X is oxygen;
Y is alkylene containing one or more hetero atom; and
Z is hydrogen or a substituent which is alkyl, alkenyl, cyano, carboxy, protected carboxy, carboxyalkyl, hydroxyaminocarbonylalkyl, carbamoylalkyl, cyanoalkyl, aminoalkyl, ureidoalkyl, dialkylaminoalkyl, hydroxyalkyl, alkoxyalkyl, alkylthioalkyl, arylthioalkyl, haloalkyl, sulfamoylalkyl, alkoxysulfonylalkyl, alkylsulfonylalkyl, nitro, amino, alkoxy, acyloxy, aryloxy, oxo or halogen.

3. The compound as claimed in claim 1 wherein R is methoxy and X is oxygen.

4. The compound as claimed in claim 1 wherein R¹ is 1-methyltetrazol-5-ylthio, 1-carboxymethyltetrazol-5-ylthio, 1-carbamoylmethyltetrazol-5-ylthio, 1-cyanoethyltetrazol-5-ylthio, or 1-(2-hydroxyethyl)tetrazol-5-ylthio, thiadiazol-2-ylthio, or 2-methylthiadiazol-5-ylthio.

5. The compound as claimed in claim 1 wherein R² is hydrogen, sodium or potassium.

6. The compound as claimed in claim 1 wherein wherein Y is —NHCH₂CH₂CH₂—, —NHCH₂CH₂S—, or —NHCH₂S—.

7. The compound as claimed in claim 1 wherein Z is hydrogen or methyl.

8. The compound as claimed in claim 1 that is 7β-(3-oxo-tetrahydro-1,4-thiazin-2-yl)carboxamido-7α-methoxy-3-(1-methyltetrazol-5-yl)thiomethyl-1-dethia-1-oxa-3-cephem-4-carboxylic acid or its sodium salt.

9. The compound as claimed in claim 1 that is 7β-(3-oxo-tetrahydro-1,4-thiazin-2-yl)carboxamido-7α-methoxy-3-(1-(2-hydroxyethyl)tetrazol-5-yl)thiomethyl-1-dethia-1-oxa-3-cephem-4-carboxylic acid or its sodium salt.

10. The compound as claimed in claim 1 that is 7β-(3-oxo-tetrahydro-1,4-thiazin-2-yl)carboxamido-7α-methoxy-3-(1-cyanoethyltetrazol-5-yl)thiomethyl-1-dethia-1-oxa-3-cephem-4-carboxylic acid or its sodium salt.

11. The compound as claimed in claim 1 that is 7β-(3-oxo-tetrahydro-1,4-thiazin-2-yl)carboxamido-7α-methoxy-3-(1-carboxymethyltetrazol-5-yl)thiomethyl-1dethia-1-oxa-3-cephem-4-carboxylic acid or its sodium salt.

12. The compound as claimed in claim 1 that is 7β-(3-oxo-tetrahydro-1,4-thiazin-2-yl)carboxamido-7α-methoxy-3-(1-carbamoylmethyltetrazol-5-yl)thiomethyl-1-dethia-1-oxa-3-cephem-4-carboxylic acid or its sodium salt.

13. The compound according to claim 1 which is 7β-[4-methyl-3-oxo-2,3,5,6-tetrahydro-1,4-thiazin-2-yl]carbon-amino-7α-methoxy-3-[1-(2hydroxyethyl-1H-tetrazol-5-yl)thiomethyl-1-dethia-1-oxa-3-cephem-4-carboxylic acid.

14. The pharmaceutical composition containing a 7β-(oxo saturated heterocyclic carboxamido)-3-cephem-4-carboxylic acid derivative as claimed in claim 1 as an active ingredient and a conventional carrier.

* * * * *